United States Patent
Olson et al.

(10) Patent No.: US 7,022,323 B2
(45) Date of Patent: Apr. 4, 2006

(54) USES OF DC-SIGN AND DC-SIGNR FOR INHIBITING HEPATITIS C VIRUS INFECTION

(75) Inventors: William C. Olson, Ossining, NY (US); Paul J. Maddon, Scarsdale, NY (US)

(73) Assignee: Progenics Pharmaceuticals, Inc., Tarrytown, NY (US)

( * ) Notice: Subject to any disclaimer, the term of this patent is extended or adjusted under 35 U.S.C. 154(b) by 67 days.

(21) Appl. No.: 10/184,150

(22) Filed: Jun. 26, 2002

(65) Prior Publication Data

US 2003/0134297 A1 Jul. 17, 2003

Related U.S. Application Data

(60) Provisional application No. 60/300,971, filed on Jun. 26, 2001.

(51) Int. Cl.
  *A61K 39/00* (2006.01)
  *A61K 39/395* (2006.01)
  *C07K 16/00* (2006.01)
  *C07K 16/28* (2006.01)
  *C12P 21/08* (2006.01)

(52) U.S. Cl. .............. 424/141.1; 424/130.1; 424/133.1; 424/143.1; 530/387.1; 530/387.3; 530/388.1; 530/388.22

(58) Field of Classification Search ........ 530/300, 530/350, 387.1, 387.3, 387.9, 388.1, 388.15, 530/388.22, 388.85, 389.1; 424/130.1, 133.1, 424/135.1, 139.1, 141.1, 142.1, 143.1, 172.1; 435/4, 5, 7.1, 7.2; 514/2
See application file for complete search history.

(56) References Cited

U.S. PATENT DOCUMENTS

| | | | |
|---|---|---|---|
| 5,595,868 | A | 1/1997 | Habets et al. |
| 5,679,342 | A | 10/1997 | Houghton et al. |
| 6,391,567 | B1 | 5/2002 | Littman et al. |

FOREIGN PATENT DOCUMENTS

| | | |
|---|---|---|
| EP | 1046651 | 10/2000 |
| WO | 9208734 | 5/1992 |
| WO | 0063251 | 10/2000 |
| WO | 0250119 | 6/2002 |
| WO | 03000024 | 1/2003 |

OTHER PUBLICATIONS

Rudikoff et al., Proceedings of the National Academy of Sciences, USA, vol. 79, pp. 1979-1983 (Mar. 1982).*
Poljak et al., Philosophical Transactions of the Royal Society of London, Series B: Biological Sciences, vol. 272, pp. 43-51 (Nov. 1975).*
Bartosch et al, Journal of Biological Chemistry, vol. 278 No. 43, pp. 41624-41630 (Oct. 2003).*
Daugherty et al., Nucleic Acids Research, vol. 19 No. 9, pp. 2471-2476 (May 1991).*
Walker et al., Antiviral Chemistry & Chemotherapy, vol. 14 No. 1, pp. 1-21 (Jan. 2003).*
U.S. Appl. No. 60/300,971, filed Jun. 26, 2001, Olson et al.
U.S. Appl. No. 09/891,894, filed Jun. 26, 2001, Olson et al.
U.S. Appl. No. 10/328,997, filed Dec. 24, 2002, Olson et al.
Mitchell, D.A., Fadden, A.J. and Drickamer, K. (2001) A novel mechanism of carbohydrate recognition by the C-type lectins DC-SIGN and DC-SIGNR. Subunit organization and binding to multivalent ligands. J. Biol. Chem. 276: 28939-28945.

(Continued)

*Primary Examiner*—James C. Housel
*Assistant Examiner*—Zachariah Lucas
(74) *Attorney, Agent, or Firm*—John P. White, Esq.; Cooper & Dunham LLP

(57) ABSTRACT

This invention provides a method of inhibiting HCV infection of a cell susceptible to HCV infection which comprises contacting the cell with an amount of a compound effective to inhibit binding of an HCV envelope glycoprotein to a DC-SIGN protein present on the surface of the cell, so as to thereby inhibit HCV infection of the cell susceptible to HCV infection. This invention provides a method of inhibiting HCV infection of a cell susceptible to HCV infection which comprises contacting the cell with an amount of a compound effective to inhibit binding of an HCV envelope glycoprotein to a DC-SIGNR protein present on the surface of the cell, so as to thereby inhibit HCV infection of the cell susceptible to HCV infection. Compounds of the present invention inhibit HCV infection of cells susceptible to HCV infection. The compounds of the present invention preferably have specificity for preventing or inhibiting infection by HCV and do not inhibit infection by other viruses, such as HIV, that may utilize DC-SIGN or DC-SIGNR for infection. Moreover the compounds of the present invention preferably do not interfere or inhibit members of the immunoglobulin superfamily, in particular, the compounds do not interfere with ICAM-2 or ICAM-3 or with ICAM-2-ilke, or ICAM-3-like molecules.

23 Claims, 6 Drawing Sheets

OTHER PUBLICATIONS

Geijtenbeek, T.B.H. et al. (2000) Identification of DC-SIGN, a novel dendritic cell-specific ICAM-3 receptor that supports primary immune responses. Cell 100: 575-585.

Nguyen, D.G. and Hildreth, J.E.K. (2003) Involvement of macrophage mannose receptor in the binding and transmission of HIV by macrophages. European Journal of Immunology 33:483-493; and.

Pohlmann, S. et al. (2003) Hepatitis C virus glycoproteins interact with DC-SIGN and DC-SIGNR. Journal of Virology 77: 4070-4080.

Auffermann-Gretzinger, S., E.B. Keeffe, and S. Levy. 2001. Impaired dendritic cell maturation in patients with chronic, but not resolved, hepatitis C virus infection. Blood 97: 3171-3176.

Bain, C., A. Fatmi, F. Zoulim, J.P. Zarski, C. Trepo, and G. Inchauspe. 2001. Impaired allostimulatory function of dendritic cells in chronic hepatitis C infection. Gastroenterology 120: 512-524.

Baribaud, F., S. Pohlmann, T. Sparwasser, M.T. Kimata, Y.K. Choi, et al. 2001. Functional and antigenic characterization of human, rhesus macaque, pigtailed macaque, and murine DC-SIGN. J. Virol. 75: 10281-10289.

Bashirova, A.A., T.B. Geijtenbeek, G.C. van Duijnhoven, S.J. van Vliet, J.B. Eilering, et al. 2001. A dendritic cell-specific intercellular adhesion molecule 3-grabbing nonintegrin (dc-sign)-related protein is highly expressed on human liver sinusoidal endothelial cells and promotes HIV-1 infection. J. Exp. Med. 193: 671-678.

Carloni, G., S. Iacovacci, M. Sargiacomo, G. Ravagnan, A. Ponzetto, C. Peschle, and M. Battaglia. 1993. Suspectibility of human liver cell cultures to hepatitis C virus infection. Arch. Virol. Suppl. 8:31-39.

Cocquerel, L., C. Wychowski, F. Minner, F. Penin, and J. Dubuisson. 2000. Charged residues in the transmembrane domains of hepatitis C virus glycoproteins play a major role in the processing, subcellular localization, and assembly of these envelope proteins. J. Virol. 74: 3623-3633.

Cocquerel, L., J.C. Meunier, A. Pillez, C. Wychowski, and J. Dubuisson. 1998. A retention signal necessary and sufficient for endoplasmic reticulum localization maps to the transmembrane domain of hepatitis C virus glycoprotein E2. J. Virol. 72: 2183-2191.

Cocquerel, L., S. Duvet, J.C. Meunier, A. Pillez, R. Cacan, C. Wychowski, and J. Dubuisson. 1999. The transmembrane domain of hepatitis C virus glycoprotein E1 is a signal for static retention in the endoplasmic reticulum. J. Virol. 73: 2641-2649.

Deleersnyder, V., A. Pillez, C. Wychowski, K. Blight, J. Xu, Y.S. Hahn, C.M. Rice, and J. Dubuisson. 1997. Formation of native hepatitis C virus glycoprotein complexes. J. Virol. 71: 697-704.

Dubisson, J. 2000. Folding, assembly and subcellular localization of hepatitis C virus glycoproteins. Curr. Top. Microbiol. Immunol. 242: 135-148.

Flint M, and J.A. McKeating. 2000. The role of the hepatitis C virus glycoproteins in infection. Rev. Med. Virol. 10: 101-117.

Flint, M., J. Dubuisson, C. Maidens, R. Harrop, G.R. Guile, P. Borrow, and J.A. McKeating. 2000. Functional characterization of intracellular and secreted forms of a truncated hepatitis C virus E2 glycoprotein. J. Virol. 74: 702-709.

Flint, M., J.M. Thomas, C.M. Maidens, C. Shotton, S. Levy, W.S. Barclay, and J.A. McKeating. 1999. Functional analysis of cell surface-expressed hapatitis C virus E2 glycoprotein. J. Virol. 73: 6782-6790.

Geijtenbeek, T.B., D.S. Kwon, R. Torensma, S.J. van Vliet, G.C. van Duijnhoven, J. Middel, J.L. Cornelissen, H.S. Nottet, V.N. KewalRamani, D.R. Littman, C.G. Figdor, and Y. van Kooyk. 2000. DC-SIGN, a dendritic cell-specific HIV-1-binding protein that enhances trans-infection of T cells. Cell 100: 587-597.

Geijtenbeek, T.B., Y. van Kooyk, S.J. van Vliet, M.H. Renes, R.A. Raymakers, and C.G. Figdor. 1999. High frequency of adhesion defects in B-lineage acute lymphoblastic leukemia. Blood 94: 754-764.

Iacovacci, S., L. Bertolini, A. Manzin, M.B. Valli, M. Battaglia, A. Ponzetto, M. Clementi, and G. Carloni. 1997. Quantitation of hepatitis C virus RNA production in two human bone marrow-derived B-cell lines infected in vitro. Res. Virol. 148: 147-151.

Jameson, B., F. Baribaud, S. Pohlmann, D. Ghavimi, F. Mortari, R.W. Doms, and A. Iwasaki. 2002 Expression of DC-SIGN by dendritic cells of intestinal and genital mucosae in humans and rhesus macaques. J. Virol. 76: 1866-1875.

Jones, I.M., C. Chan-Fook, W.R. Jiang, and B.E. Clarke. 2000. Receptors for hepatitis C virus. J. Virol. 74: 10860-10861.

Kanto, T., N. Hayashi, T. Takehara, T. Tatsumi, N. Kuzushita, A. Ito, Y. Sasaki, A. Kasahara, and M. Hori. 1999. Impaired allostimulatory capacity of peripheral blood dendritic cells recovered from hepatitis C virus-infected inviduals, J. Immunol. 162: 5584-5591.

Lagging, L.M., K. Meyer, R.J. Owens, and R. Ray. 1998. Functional role of hepatitis C virus chimeric glycoproteins in the infectivity of pseudotyped virus. J. Virol. 72: 3539-3546.

Lanford, R.E., C. Sureau, J.R. Jacob, R. White, and T.R. Fuerst. 1994. Demonstration of in vitro infection of chimpanzee hepatocytes with hepatitis C virus using strand-specific RT/PCR. Virology 202: 606-614.

Lohmann, V., F. Korner, J. Koch, U. Herian, L. Theilmann, and R. Bartenschlager. 1999. Replication of subgenomic hepatitis C virus RNAs in a hepatoma cell line. Science 285: 110-113.

Matsuura, Y., T. Suzuki, R. Suzuki, M. Sato, H. Aizaki, I. Saito, and T. Miyamura. 1994. Processing of E1 and E2 glycoproteins of hepatitis C virus expressed in mammalian and insect cells. Virology 205: 141-150.

Mellor, J., G. Haydon, C. Blair, W. Livingstone, and P. Simmonds. 1998. Low level or absent in vivo replication of hepatitis C virus and hepatitis G virus/GB virus C in peripheral blood mononuclear cells. J. Gen. Virol. 79 (Pt 4): 705-714.

Meola, A., A. Sbardellati, E.B. Bruni, M. Cerretani, M. Pezzanera, A. Ceccacci, A. Vitelli, S. Levy, A. Nicosia, C. Traboni, J. McKeating, and E. Scarselli. 2000. Binding of hepatitis C virus E2 glycoprotein to CD81 does not correlate with species permissiveness to infection. J. Virol. 74: 5933-5938.

Navas, M.C,, A. Fuchs, E. Schvoerer, A. Bohbot, A.M. Aubertin, and F. Stoll-Keller F. 2002. Dendritic cell suspectibility to hepatitis C virus genotype 1 infection. J. Med. Virol. 67: 152-61.

Op De Beeck, A., R. Montserret, S. Duvet, L. Cocquerel, R. Cacan, B. Barberot, M. Le Maire, F. Penin, and J. Dubuisson. 2000. The transmembrane domains of hepatitis C virus envelope qlycoproteins E1 and E2 play a major role in heterodimerization. J. Biol. Chem. 275: 31428-31437.

Pohlmann, S., E.J. Soilleux, F. Baribaud, G.J. Leslie, L.S. Morris, J. Trowsdale, B. Lee, N. Coleman, and R.W. Doms. 2001. DC-SIGNR, a DC-SIGN homologue expressed in endothelial cells, binds to human and simian immunodeficiency viruses and activates infection in trans. Proc. Natl. Acad. Sci. U.S.A. 98: 2670-2675.

Soilleux, E.J., R. Barten, and J. Trowsdale. 2000. DC-SIGN; a related gene, DC-SIGNR; and CD23 form a cluster on 19p13. 165: 2937-2942.

Takikawa, S., K. Ishii, H. Aizaki, T. Suzuki, H. Asakura, Y. Matsuura, and T. Miyamura. 2000. Cell fusion activity of hepatitis C virus envelope proteins. J. Virol. 74:5066-5074.

Wu, L., T.D. Martin, R. Vazeux, D. Unutmaz, and V.N. KewalRamani. 2002. Functional evaluation DC-SIGN monoclonal antibodies reveals DC-SIGN interactions with ICAM-3 do not promote human immunodeficiency virus type 1 transmission. J. Virol. 76: 5905-5914.

Young, K.K., R.M. Resnick, and T.W. Myers. 1993. Detection of hepatitis C virus RNA by a combined reverse transcription-polymerase chain reaction assay. J. Clin. Microbiol. 31: 882-886.

Chien, D.Y, P. Arcangel, A. Medina-Selby, D. Coit, M. Baumeister et al. (1999) Use of a novel hepatitis C virus (HCV) major-epitope chimeric polypeptide for diagnosis of HCV infection. J. Clin. Microbiol. 37(5): 1393-1397..

Meyer, K., A. Basu and R. Ray (2000) Functional features of hepatitis C virus glycoproteins for pseudotype virus entry into mammalian cells. Virology 276(1): 214-226.

* cited by examiner

FIGURE 1

```
msdskeprlq qlglleeeql rglgfrqtrg ykslagclgh gplvlqllsf tllagllvqv
skvpssisqe qsrqdaiyqn ltqlkaavge lseksklqei yqeltqlkaa vgelpekskl
qeiyqeltrl kaavgelpek sklqeiyqel twlkaavgel pekskmqeiy qeltrlkaav
gelpekskqq eiyqeltrlk aavgelpeks kqqeiyqelt rlkaavgelp ekskqqeiyq
eltqlkaave rlchpcpwew tffqgncyfm snsqrnwhds itackevgaq lvviksaeeq
nflqlqssrs nrftwmglsd lnqegtwqwv dgspllpsfk qywnrgepnn vgeedcaefs
gngwnddkcn lakfwickks aascsrdeeq flspapatpn pppa

*FIGURE 2*

```
msdskeprvq qlglleedpt tsgirlfprd fqfqgihghk sstgclghga lvlgllsfml
lagvlvailv qvskvpssls geqseqdaiy qnltqlkaav gelseksklq eiyqeltqlk
aavgelpeks klqeiyqelt rlkaavgelp eksklqeiyq eltrlkaavg elpeksklqe
iyqelt

FIGURE 3

```
MSTNPKPQRKTKRNTNRRPQDVKFPGGGQIVGGVYLLPRRGPRL
GVRATRKTSERSQPRGRROPIPKARRPEGRTWAQPGYPWPLYGNEGCGWAGWLLSPRG
SRPSWGPTDPRRRSRNLGKVIDTLTCGFADLMGYIPLVGAPLGGAARALAHGVRVLED
GVNYATGNLPGCSFSIFLLALLSCLTVPASAYQVRNSSGLYHVTNDCPNSSIVYEAAD
AILHTPGCVPCVREGNASRCWVAVTPTVATRDGKLPTTQLRRHIDLLVGSATLCSALY
VGDLCGSVFLVGQLFTFSPRRHWTTQDCNCSIYPGHITGHRMAWDMMMNWSPTAALVV
AQLLRIPQAIMDMIAGAHWGVLAGIAYFSMVGNWAKVLVVLLLFAGVDAETHVTGGSA
GRTTAGLVGLLTPGAKQNIQLINTNGSWHINSTALNCNESLNTGWLAGLFYQHKFNSS
GCPERLASCRRLTDFAQGWGPISYANGSGLDERPYCWHYPPRPCGIVPAKSVCGPVYC
FTPSPVVVGTTDRSGAPTYSWGANDTDVFVLNNTRPPLGNWFGCTWMNSTGFTKVCGA
PPCVIGGVGNNTLLCPTDCFRKHPEATYSRCGSGPWITPRCMVDYPYRLWHYPCTINY
TIFKVRMYVGGVEHRLEAACNWTRGERCDLEDRDRSELSPLLLSTTQWQVLPCSFTTL
PALSTGLIHLHQNIVDVQYLYGVGSSIASWAIKWEYVVLLFLLLADARVCSCLWMMLL
ISQAEAALENLVILNAASLAGTHGLVSFLVFFCFAWYLKGRWVPGAVYAFYGMWPLLL
LLLALPQRAYALDTEVAASCGGVVLVGLMALTLSPYYKRYISWCMWWLQYFLTRVEAQ
LHVWVPPLNVRGGRDAVILLMCVVHPTLVFDITKLLLAIFGPLWILQASLLKVPYFVR
VQGLLRICALARKIAGGHYVQMAIIKLGALTGTYVYNHLTPLRDWAHNGLRDLAVAVE
PVVFSRMETKLITWGADTAACGDIINGLPVSARRGQEILLGPADGMVSKGWRLLAPIT
AYAQQTRGLLGCIITSLTGRDKNQVEGEVQIVSTATQTFLATCINGVCWTVYHGAGTR
TIASPKGPVIQMYTNVDQDLVGWPAPQGSRSLTPCTCGSSDLYLVTRHADVIPVRRRG
DSRGSLLSPRPISYLKGSSGGPLLCPAGHAVGLFRAAVCTRGVAKAVDFIPVENLETT
MRSPVFTDNSSPFAVPQSFQVAHLHAPTGSGKSTKVPAAYAAQGYKVLVLNPSVAATL
GFGAYMSKAHGVDPNIRTGVRTITTGSPITYSTYGKFLADGGCSGGAYDIIICDECHS
TDATSILGIGTVLDQAETAGARLVVLATATPPGSVTVSHPNIEEVALSTTGEIPFYGK
AIPLEVIKGGRHLIFCHSKKKCDELAAKLVALGINAVAYYRGLDVSVIPTSGDVVVVS
TDALMTGFTGDFDSVIDCNTCVTQTVDFSLDPTFTIETTTLPQDAVSRTQRRGRTGRG
KPGIYRFVAPGERPSGMFDSSVLCECYDAGCAWYELTPAETTVRLRAYMNTPGLPVCQ
DHLEFWEGVFTGLTHIDAHFLSQTKQSGENFPYLVAYQATVCARAQAPPPSWDQMWKC
LIRLKPTLHGPTPLLYRLGAVQNEVTLTHPITKYIMTCMSADLEVVTSTWVLVGGVLA
ALAAYCLSTGCVVIVGRIVLSGKPAIIPDREVLYQEFDEMEECSQHLPYIEQGMMLAE
QFKQKALGLLQTASRQAEVITPAVQTNWQKLEVFWAKHMWNFISGIQYLAGLSTLPGN
PAIASLMAFTAAVTSPLTTGQTLLFNILGGWVAAQLAAPGAATAFVGAGLAGAAIGSV
GLGKVLVDILAGYGAGVAGALVAFKIMSGEVPSTEDLVNLLPAILSPGALVVGVVCAA
ILRRHVGPGEGAVQWMNRLIAFASRGNHVSPTHYVPESDAAARVTAILSSLTVTQLLR
RLHQWISSECTTPCSGSWLRDIWDWICEVLSDFKTWLKAKLMPQLPGIPFVSCQRGYR
GVWRGDGIMHTRCHCGAEITGHVKNGTMRIVGPRTCRNMWSGTFPINAYTTGPCTPLP
APNYKFALWRVSAEEYVEIRRVGDFHYVSGMTTDNLKCPCQIPSPEFFTELDGVRLHR
FAPPCKPLLREEVSFRVGLHEYPVGSQLPCEPEPDVAVLTSMLTDPSHITAEAAGRRL
ARGSPPSMASSSASQLSAPSLKATCTANHDSPDAELIEANLLWRQEMGGNITRVESEN
KVVILDSFDPLVAEEDEREVSVPAEILRKSRRFARALPVWARPDYNPPLVETWKKPDY
EPPVVHGCPLPPPRSPPVPPPRKKRTVVLTESTLSTALAELATKSFGSSSTSGITGDN
TTTSSEPAPSGCPPDSDVESYSSMPPLEGEPGDPDLSDGSWSTVSSGADTEDVVCCSM
SYSWTGALVTPCAAEEQKLPINALSNSLLRHHNLVYSTTSRSACQRQKKVTFDRLQVL
DSHYQDVLKEVKAAASKVKANLLSVEEACSLTPPHSAKSKFGYGAKDVRCHARKAVAH
INSVWKDLLEDSVTPIDTTIMAKNEVFCVQPEKGGRKPARLIVFPDLGVRVCEKMALY
DVVSKLPLAVMGSSYGFQYSPGQRVEFLVQAWKSKKTPMGFSYDTRCFDSTVTESDIR
TEEAIYQCCDLDPQARVAIKSLTERLYVGGPLTNSRGENCGYRRCRASGVLTTSCGNT
LTCYIKARAACRAAGLQDCTMLVCGDDLVVICESAGVQEDAASLRAFTEAMTRYSAPP
GDPPQPEYDLELITSCSSNVSVAHDGAGKRVYYLTRDPTTPLARAAWETARHTPVNSW
LGNIIMFAPTLWARMILMTHFFSVLIARDQLEQALNCEIYGACYSIEPLDLPPIIQRL
HGLSAFSLHSYSPGEINRVAACLRKLGVPPLRAWRHRARSVRARLLSRGGRAAICGKY
LFNWAVRTKLKLTPIAAAGRLDLSGWFTAGYSGGDIYHSVSHARPRWFWFCLLLLAAG
```

*FIGURE 5A*
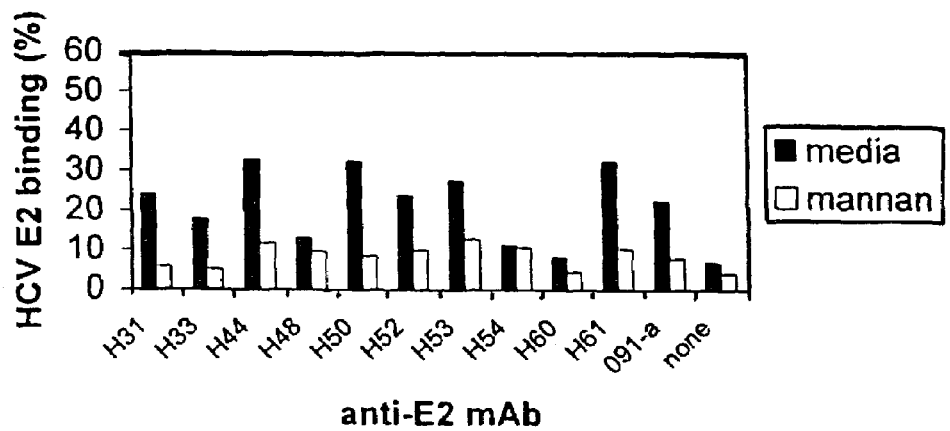
*FIGURE 5B* B. Hela-DC-SIGN-R
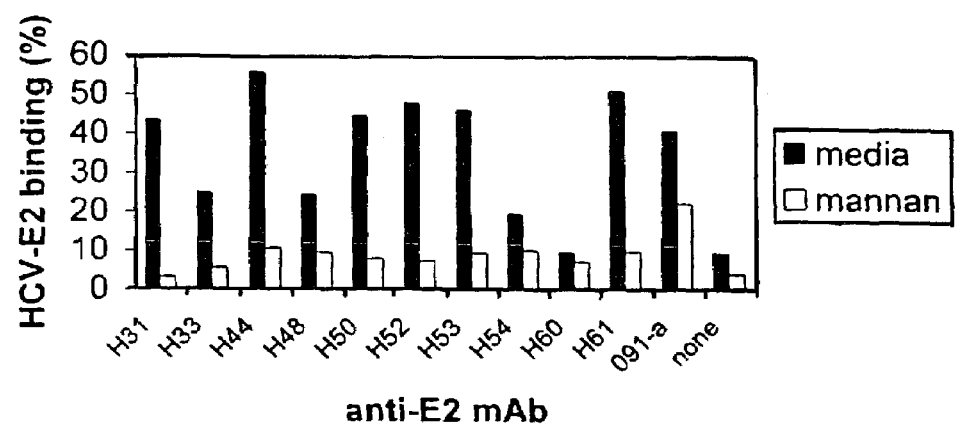
*FIGURE 5C* C. HeLa parent
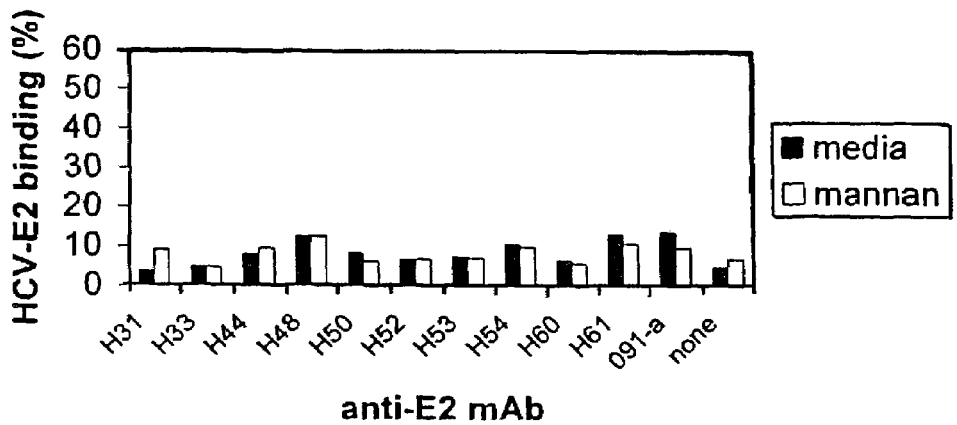

USES OF DC-SIGN AND DC-SIGNR FOR INHIBITING HEPATITIS C VIRUS INFECTION

This application is a continuation-in-part of, and claims the priority of, U.S. Provisional Application No. 60/300,971, filed Jun. 26, 2001, the contents of which is hereby incorporated by reference.

Throughout this application, various publications are referenced by Arabic numerals. Full citations for these publications may be found at the end of the specification immediately preceding the claims. The disclosure of these publications is hereby incorporated by reference into this application to describe more fully the art to which this invention pertains.

BACKGROUND OF THE INVENTION

Hepatitis C virus was first recognized in 1989 and is responsible for the majority of cases of non-A, non-B hepatitis. [1] Infections are typically chronic and lifelong; many infected individuals are healthy and unaffected for decades, whereas others develop chronic hepatitis or cirrhosis, the latter often leading to hepatocellular carcinoma. [16] While screening of the blood supply has drastically reduced new transmissions of the virus, there exists a large cohort of infected individuals who will require treatment in the coming decades. Some reports estimate that nearly 3% of the world's population (including about 4 million people in the U.S.) is infected with HCV. [2] It is estimated that 170 million people worldwide, including about 4 million people in the US, are infected with HCV. Infected individuals have or will develop liver disease with clinical outcomes ranging from an asymptomatic carrier state to active hepatitis and cirrhosis. Chronic infection is also strongly associated with the development of hepatocellular carcinoma. HCV infection and its clinical sequelae are the leading causes of liver transplantation in the US. No vaccine is currently available. Several preparations of interferon alpha and interferon alpha-2b plus ribavirin are presently used for the treatment of chronic hepatitis C. [32] The best long-term response rates are obtained with a combination of interferon alpha-2b and ribavirin. However, only a minority of subjects treated with this combination achieves the desired result of no detectable serum HCV RNA 6 months after stopping treatment. [32] The optimal treatment with these drugs for all infected individuals, including those co-infected with HIV-1, has not been established because data on viral dynamics in response to treatment are scarce. Interferon alpha and ribavirin are non-specific anti-viral agents with incompletely understood mechanisms of action. They also are associated with severe and life-threatening toxicities, including neutropenia, hemolytic anemia and severe depression.

There is an urgent need for new therapeutic agents to combat HCV infection. A particularly attractive target for antiviral therapy is HCV entry into target cells because such inhibitors do not need to cross the plasma membrane nor be modified intracellularly. In addition, viral entry is generally a rate-limiting step that is mediated by conserved structures on the virus and cell membrane. Consequently, inhibitors of viral entry can provide potent and durable suppression of viral replication.

The HCV genome is a 9.4 kilobase positive-sense, single-stranded RNA molecule that encodes a single polyprotein of ~3000 amino acids. [42] A number of isolates have been characterized and found to exhibit considerable sequence diversity. Virus sequences can be divided into major genotypes (exhibiting <70% sequence identity), and further into subtypes (exhibiting 80–90% identity). [53] Genotype 1 (subtypes 1a and 1b) predominates in North America, Europe, and Japan. [46] There is no clear differences in pathology associated with the different genotypes.

Despite the sequence diversity among isolates, many features are held in common. The genomic RNA contains a long 5' non-translated region (NTR) of about 340 nucleotides, followed by a single long open reading frame (ORF) encoding a polyprotein of about 3000 amino acids. [42] A short 3' NTR is followed by a polyA sequence and 98 highly conserved nucleotides (the "X" region). Translation of the RNA is mediated by an IRES element in the 5' NTR. The polyprotein precursor is processed to generate at least ten proteins: from amino- to carboxy-terminus these are termed C, E1, E2, p7, NS2, NS3, NS4A, NS4B, NS5A, and NS5B. [19] The C protein constitutes the nucleocapsid; E1 and E2 are transmembrane envelope glycoproteins; p7 is of unknown function; the various NS proteins are nonstructural proteins with replication functions. Polyprotein cleavage in the structural region (C-p7) is catalyzed in the endoplasmic reticulum (ER) by cellular signal peptidases. Cleavage of the polyprotein in the nonstructural region (NS2-NS5B) is mediated by HCV encoded proteinases. NS2 and NS3 constitute a protease that cleaves the NS2-NS3 junction. NS3 is a dual function protein, containing at its amino-terminus a serine protease domain responsible for cleavage at the remaining sites in the precursor, and an RNA helicase/NTPase domain at its carboxy-terminus. NS4A is thought to enhance or direct the protease activity of NS3, while the functions of NS4B and NS5A are unclear. NS5B is an RNA-dependent RNA polymerase (RdRp) and the catalytic subunit of the replicase for the virus. This enzyme recognizes the 3' end of the RNA and carries out RNA synthesis to create a minus-strand RNA. The 3' end of the minus strand is then similarly recognized by the RdRp to initiate synthesis of plus strand RNAs. As these progeny viral RNAs are made they are packaged into assembling virions. HCV particles bud into the ER and are transported out of the cell by microsomal vesicles. [42]

There are few animal models for HCV infection. These include the chimpanzee [22] [27] [45] which is an endangered species. Another model is the SCID-BNX model, whereby immunodeficient mice are implanted with human liver tissue that is infected with HCV as described. [54] Studies of viral replication in vitro have largely depended on infection of cell lines or primary hepatic cultures with sera of HCV-infected patients. [4] [5] [23] [24] [26] [29] [44] [51] However, the levels of viral RNA in these infected cultures are very low and can only be detected by PCR. [4] [5] [23] [24] [26] [29] [44] [51] In an important recent advance, Lohmann et al. [30] replaced the structural genes in a complete subtype 1b genome with the neomycin phosphotransferase gene followed by the IRES of the encephalomyocarditis virus. In the resulting construct, the phosphotransferase gene was downstream of the HCV 5' NTR (containing the HCV IRES), while the HCV nonstructural genes were downstream of the encephalomyocarditis virus IRES. RNA was transcribed from this construct and transfected into the human hepatoma cell line, Huh-7. After selection in neomycin, cell lines were obtained which showed robust replication of the transfected mini-genome; viral RNA could be detected by Northern analysis and viral proteins could be detected by immunoprecipitation. There is an urgent need for additional animal models of HCV infection.

HCV entry into host cells requires attachment of the viral particle to the cell surface, followed by fusion of the viral envelope with the cellular membrane. This process is mediated by the viral envelope glycoproteins E1 and E2. Two proteins, named E1 and E2 (corresponding to amino acids 192–383 and 384–750 of the HCV polyprotein respectively), have been suggested to be external proteins of the viral envelope which are responsible for the binding of virus to target cells. HCV E1 and E2 have been expressed recombinantly in a number of forms and using a variety of expression systems. Two recent reports have described fusion and entry mediated by E1 and E2 ectodomains fused to the TM domain of the VSV G envelope glycoprotein. [28] [49]

In mammalian cell-based expression systems, the molecular weight of mature, full length E1 is ~35 kD and that of E2 is ~72 kD. [19] [31] [48] The amino-terminal residues of mature E1 and E2 were determined experimentally. [21] Endoproteolytic processing of the HCV polyprotein converts E1 and E2 into type-1 membrane-anchored proteins. [19] [48] Furthermore, E1 and E2 form non-covalently associated heterodimers, from hereon referred to as E1/E2. [8] [19] [37] [41] Fully processed E1/E2 heterodimers are not exported to the cell surface, but are retained in the ER, where HCV budding occurs. [9] [10] [11] [12] [43] Analyses of E1 and E2 N-linked glycosylation patterns further showed that these proteins are retained in the ER without cycling through the Golgi. [12] [34] The ER retention signals are located in the TM domains of E1 and E2. [6] [7] [14] Replacing the TM domains of E1 and E2 by the TM domains of plasma membrane-associated proteins, or mutating charged residues in the TM domains of E1 and E2, results in cell surface expression of the envelope glycoproteins. [6] [7] [8] [14] Such TM domain modifications, however, also abrogate E1/E2 heterodimerization. [7] [36] The dimerization and ER retention signals of E1 and E2 therefore cannot be dissociated. Deletion of the entire TM domain of E1 and E2 results in the secretion of soluble, monomeric ectodomains of the envelope glycoproteins. [12] [13] [35]

To date, two human cellular proteins, CD81 and low-density lipoprotein (LDL) receptors, have been implicated as putative receptors that mediate HCV entry [25], and glycosaminoglycans have been suggested to play a role in the nonspecific attachment of HCV to cell. [52] Uses of the CD81 in the treatment and diagnosis of HCV infection are disclosed by Abrignani et al. in the international patent application WO 99/18198. Studies have demonstrated that the recombinant soluble E2 ectodomain binds specifically and with high affinity to human and chimpanzee CD81, but not to CD81 from other species. [15] [20] [38] [39] However, these results have come into question in light of a recent studies, including one showing that tamarin CD81, a species that is refractive to HCV infection, also binds soluble E2 with high affinity. [33] Even though a number of studies have defined the structural determinants of the human CD81/E2 interaction, direct functional proof of CD81-mediated HCV fusion and entry is still lacking. Moreover, CD81 is expressed on numerous tissues outside of the liver, and thus CD81 tissue distribution fails to explain the cellular tropism of HCV. Similarly, studies to date have failed to demonstrate a direct interaction between LDL receptors and the HCV envelope glycoproteins. [52] In addition, LDL receptors are widely expressed on tissues other than liver, and thus its expression does not explain the tropism of HCV.

DC-SIGN (Dendritc Cell-Specific Intercellular adhesion molecule 3-Grabbing Nonintegrin, Genbank accession number AF209479) and DC-SIGNR (DC-SIGN Related, Genbank accession number AF245219) are type II membrane proteins with close sequence homologies (77% identity in amino acids). DC-SIGN is expressed at high levels on dendritic cells; DC-SIGNR is expressed at high levels in liver and lymph nodes but not on dendritic cells; and both molecules are expressed on endometrium and placenta. [40] [47] [3] [17]

The proteins are C-type (calcium-dependent) lectins that possess all of the residues known to be required for binding of mannose. DC-SIGN and DC-SIGNR bind the HIV-1 surface envelope glycoprotein gp120, which possesses high-mannose sugars, and this binding is inhibited by mannan. [47] [3] [17] Both DC-SIGN and DC-SIGNR bind infectious HIV-1 particles and promote infection of susceptible T cells in trans. [40] [47] [3] European patent applications EP 1046651A1 and EP 1086137 A1 describe the use of DC-SIGN in compositions and methods for inhibiting HIV-1 infection. The entire contents of these applications are incorporated herein by reference.

Like DC-SIGN and DC-SIGNR, the lectin *Galanthus nivalis* (GNA lectin) from snowdrop bulbs avidly binds carbohydrates and glycoproteins possessing high-mannose structures. Notably, GNA lectin avidly binds HIV-1 envelope glycoproteins. [18] [50] In addition, GNA captures the HCV envelope glycoproteins [13], which contain high-mannose carbohydrates. Based on these findings, we have discerned that DC-SIGN and DC-SIGNR avidly bind HCV envelope glycoproteins and thus serve as receptors for the virus.

To our knowledge, no association has been made between DC-SIGN, DC-SIGNR and HCV infection. DC-SIGN and DC-SIGNR are also able to mediate internalization, as required for cellular entry and infection by HCV but not HIV-1. In addition, DC-SIGNR in particular is expressed at high levels in liver, the primary target organ for HCV infection. Since the ability of DC-SIGN and particularly DC-SIGNR to serve as receptors for HCV has not been previously appreciated, this discovery affords the opportunity to treat or prevent HCV infection through therapies or vaccines that block the specific interaction between HCV and these receptors.

SUMMARY OF THE INVENTION

This invention provides a method of inhibiting HCV infection of a cell susceptible to HCV infection which comprises contacting the cell with an amount of a compound effective to inhibit binding of an HCV envelope glycoprotein to a DC-SIGN protein present on the surface of the cell, so as to thereby inhibit HCV infection of the cell susceptible to HCV infection. In one embodiment the compound does not inhibit HCV binding to a DC-SIGNR protein. In another embodiment, the compound does not inhibit HIV infection of a cell susceptible to HIV infection. In a further embodiment, the compound does not block ICAM adhesion.

This invention provides a method of inhibiting HCV infection of a cell susceptible to HCV infection which comprises contacting the cell with an amount of a compound effective to inhibit binding of an HCV envelope glycoprotein to a DC-SIGNR protein present on the surface of the cell, so as to thereby inhibit HCV infection of the cell susceptible to HCV infection. In one embodiment the compound does not inhibit HCV binding to a DC-SIGN protein. In another embodiment the compound does not inhibit HIV infection of a cell susceptible to HIV infection. In a further embodiment the compound does not block ICAM adhesion.

This invention provides a method of inhibiting HCV infection of a target cell whose susceptibility to HCV infection is increased when HCV binds to a DC-SIGN protein expressing cell, which method comprises contacting the DC-SIGN protein expressing cell with an amount of a compound effective to inhibit binding of an HCV envelope glycoprotein to a DC-SIGN protein, so as to thereby inhibiting HCV infection of the target cell. In one embodiment the compound does not inhibit HCV binding to a DC-SIGNR protein. In another embodiment, the compound does not inhibit HIV infection of a cell susceptible to HIV infection. In a further embodiment, the compound does not block ICAM adhesion.

This invention provides a method of inhibiting HCV infection of a target cell whose susceptibility to HCV infection is increased when HCV binds to a DC-SIGNR protein expressing cell, which method comprises contacting the DC-SIGNR protein expressing cell with an amount of a compound effective to inhibit binding of an HCV envelope glycoprotein to a DC-SIGN protein, so as to thereby inhibiting HCV infection of the target cell. In one embodiment the compound does not inhibit HCV binding to a DC-SIGN protein. In another embodiment the compound does not inhibit HIV infection of a cell susceptible to HIV infection. In a further embodiment the compound does not block ICAM adhesion.

An embodiment of the invention involves the application of one of the methods described above wherein the cell is present in a subject and the contacting is effected by administering the compound to the subject. In another embodiment, the subject may be pregnant. The compound may be administered prior to, during or post-delivery to such a subject. In a further embodiment of the invention the compound blocks placental transmission of HCV to a fetus.

This invention provides a method of treating HCV infection in a subject which comprises inhibiting HCV infection of the subject's cells susceptible to HCV infection by a method described herein, wherein the contacting is effected by administering the compound to the subject.

This invention provides a method of determining whether a compound is capable of inhibiting HCV infection of a cell which comprises:
a) immobilizing an HCV envelope glycoprotein on a solid support;
b) contacting the immobilized HCV envelope glycoprotein with sufficient detectable DC-SIGN protein to saturate all binding sites for the DC-SIGN protein on the immobilized HCV envelope glycoprotein under conditions permitting binding of the DC-SIGN protein to the immobilized HCV envelope glycoprotein so as to form a complex;
c) removing unbound DC-SIGN protein;
d) contacting the complex with the compound; and
e) determining whether any DC-SIGN protein is displaced from the complex, wherein displacement of DC-SIGN protein from the complex indicates that the compound binds to the HCV envelope glycoprotein, so as to thereby determine that the compound is one which is capable of inhibiting HCV infection of the cell.

This invention provides a method of determining whether a compound is capable of inhibiting HCV infection of a cell which comprises:
a) immobilizing an HCV envelope glycoprotein on a solid support;
b) contacting the immobilized HCV envelope glycoprotein with sufficient detectable DC-SIGNR protein to saturate all binding sites for the DC-SIGNR protein on the immobilized HCV envelope glycoprotein under conditions permitting binding of the DC-SIGNR protein to the immobilized HCV envelope glycoprotein so as to form a complex;
c) removing unbound DC-SIGNR protein;
d) contacting the complex with the compound;
e) determining whether any DC-SIGNR protein is displaced from the complex, wherein displacement of DC-SIGNR protein from the complex indicates that the compound binds to the HCV envelope glycoprotein, so as to thereby determine that the compound is one which is capable of inhibiting HCV infection of the cell.

This invention provides a method of determining whether a compound is capable of inhibiting HCV infection of a cell which comprises:
a) immobilizing a DC-SIGN protein on a solid support;
b) contacting the immobilized DC-SIGN protein with sufficient detectable HCV envelope glycoprotein to saturate all binding sites for the HCV envelope glycoprotein on the immobilized DC-SIGN protein under conditions permitting binding of the immobilized DC-SIGN protein to the HCV envelope glycoprotein so as to form a complex;
c) removing unbound HCV envelope glycoprotein;
d) contacting the complex with the compound;
e) determining whether any HCV envelope glycoprotein is displaced from the complex, wherein displacement of HCV envelope glycoprotein from the complex indicates that the compound binds to the DC-SIGN protein, so as to thereby determine that the compound is one which is capable of inhibiting HCV infection of the cell.

This invention provides a method of determining whether a compound is capable of inhibiting HCV infection of a cell which comprises:
a) immobilizing a DC-SIGNR protein on a solid support;
b) contacting the immobilized DC-SIGNR protein with sufficient detectable HCV envelope glycoprotein to saturate all binding sites for the HCV envelope glycoprotein on the immobilized DC-SIGNR protein under conditions permitting binding of the immobilized DC-SIGNR protein to the HCV envelope glycoprotein so as to form a complex;
c) removing unbound HCV envelope glycoprotein;
d) contacting the complex with the compound;
e) determining whether any HCV envelope glycoprotein is displaced from the complex, wherein displacement of HCV envelope glycoprotein from the complex indicates that the compound binds to the DC-SIGNR protein, so as to thereby determine that the compound is one which is capable of inhibiting HCV infection of the cell.

This invention provides a method of determining whether a compound is capable of inhibiting HCV infection of a cell which comprises:
(a) contacting an HCV envelope glycoprotein with sufficient detectable DC-SIGN protein to saturate all binding sites for the DC-SIGN protein on the HCV envelope glycoprotein under conditions permitting binding of the DC-SIGN protein to the HCV envelope glycoprotein so as to form a complex;
(b) removing unbound DC-SIGN protein;
(c) measuring the amount of DC-SIGN protein which is bound to the HCV envelope glycoprotein in the complex;
(d) contacting the complex with the compound so as to displace DC-SIGN protein from the complex;
(e) measuring the amount of DC-SIGN protein which is bound to the compound in the presence of the compound; and
(f) comparing the amount of DC-SIGN protein bound to the HCV envelope glycoprotein in step (e) with the amount measured in step (c), wherein a reduced amount measured in step (e) indicates that the compound binds to the HCV envelope glycoprotein, so as to thereby determine that the compound is one which is capable of inhibiting HCV infection of the cell.

This invention provides a method of determining whether a compound is capable of inhibiting HCV infection of a cell which comprises:
(a) contacting an HCV envelope glycoprotein with sufficient detectable DC-SIGNR protein to saturate all binding sites for the DC-SIGNR protein on the HCV envelope glycoprotein under conditions permitting binding of the DC-SIGNR protein to the HCV envelope glycoprotein so as to form a complex;
(b) removing unbound DC-SIGNR protein;
(c) measuring the amount of DC-SIGNR protein which is bound to the HCV envelope glycoprotein in the complex;
(d) contacting the complex with the compound so as to displace DC-SIGNR protein from the complex;
(e) measuring the amount of DC-SIGNR protein which is bound to the compound in the presence of the compound; and
(f) comparing the amount of DC-SIGNR protein bound to the HCV envelope glycoprotein in step (e) with the amount measured in step (c), wherein a reduced amount measured in step (e) indicates that the compound binds to the HCV envelope glycoprotein so as to thereby identify the compound as one which is capable of inhibiting HCV infection of a cell.

This invention provides a method of determining whether a compound is capable of inhibiting HCV infection of a cell which comprises:
(a) immobilizing an HCV envelope glycoprotein on a solid support;
(b) contacting the immobilized HCV envelope glycoprotein with the compound and detectable DC-SIGN protein under conditions permitting binding of the DC-SIGN protein to the immobilized HCV envelope glycoprotein in the absence of the compound so as to form a complex;
(c) removing unbound DC-SIGN protein;
(d) comparing the amount of detectable DC-SIGN protein which is bound to the immobilized HCV envelope glycoprotein in the complex in the presence of the compound with the amount of detectable DC-SIGN protein which binds to the immobilized HCV envelope glycoprotein in the absence of the compound;
(e) wherein a reduced amount of DC-SIGN protein measured in the presence of the compound indicates that the compound binds to the HCV envelope glycoprotein or the DC-SIGN protein, so as to thereby determine that the compound is one which is capable of inhibiting HCV infection of the cell.

This invention provides a method of determining whether a compound is capable of inhibiting HCV infection of a cell which comprises:
(a) immobilizing an HCV envelope glycoprotein on a solid support;
(b) contacting the immobilized HCV envelope glycoprotein with the compound and detectable DC-SIGNR protein under conditions permitting binding of the DC-SIGNR protein to the immobilized HCV envelope glycoprotein in the absence of the compound so as to form a complex;
(c) removing unbound DC-SIGNR protein;
(d) comparing the amount of detectable DC-SIGNR protein which is bound to the immobilized HCV envelope glycoprotein in the complex in the presence of the compound with the amount of detectable DC-SIGNR protein which binds to the immobilized HCV envelope glycoprotein in the absence of the compound;
(e) wherein a reduced amount of DC-SIGNR protein measured in the presence of the compound indicates that the compound binds to the HCV envelope glycoprotein or the DC-SIGNR protein, so as to thereby determine that the compound is one which is capable of inhibiting HCV infection of the cell.

This invention provides a method of determining whether a compound is capable of inhibiting HCV infection of a cell which comprises:
(a) immobilizing a DC-SIGN protein on a solid support;
(b) contacting the immobilized DC-SIGN protein with the compound and detectable HCV envelope glycoprotein under conditions permitting binding of the immobilized DC-SIGN protein to the HCV envelope glycoprotein in the absence of the compound so as to form a complex;
(c) removing unbound HCV envelope glycoprotein;
(d) comparing the amount of detectable HCV envelope glycoprotein which is bound to the immobilized DC-SIGN protein in the complex in the presence of the compound with the amount of detectable HCV envelope glycoprotein which binds to the immobilized DC-SIGN protein in the absence of the compound;
(e) wherein a reduced amount of HCV envelope glycoprotein measured in the presence of the compound indicates that the compound binds to the HCV envelope glycoprotein or the DC-SIGN protein, so as to thereby determine that the compound is one which is capable of inhibiting HCV infection of the cell.

This invention provides a method of determining whether a compound is capable of inhibiting HCV infection of a cell which comprises:
(a) immobilizing a DC-SIGNR protein on a solid support;
(b) contacting the immobilized DC-SIGNR protein with the compound and detectable HCV envelope glycoprotein under conditions permitting binding of the immobilized DC-SIGNR protein to the HCV envelope glycoprotein in the absence of the compound so as to form a complex;
(c) removing unbound HCV envelope glycoprotein;
(d) comparing the amount of detectable HCV envelope glycoprotein which is bound to the immobilized DC-SIGNR protein in the complex in the presence of the compound with the amount of detectable HCV envelope glycoprotein which binds to the immobilized DC-SIGNR protein in the absence of the compound;
(e) wherein a reduced amount of HCV envelope glycoprotein measured in the presence of the compound indicates that the compound binds to the HCV envelope glycoprotein or the DC-SIGNR protein, so as to thereby determine that the compound is one which is capable of inhibiting HCV infection of the cell.

This invention provides a method of determining whether a compound is capable of inhibiting HCV infection of a cell which comprises:
(a) contacting an HCV envelope glycoprotein with the compound and detectable DC-SIGN protein under conditions permitting binding of the DC-SIGN protein to the HCV envelope glycoprotein in the absence of the compound so as to form a complex;
(b) removing unbound DC-SIGN protein;
(c) comparing the amount of detectable DC-SIGN protein which is bound to the HCV envelope glycoprotein in the complex in the presence of the compound with the amount of detectable DC-SIGN protein which binds to the compound in the absence of the compound; wherein a reduced amount of DC-SIGN protein measured in presence of the compound indicates that the compound binds to the HCV envelope glycoprotein or DC-SIGN protein so as to thereby determine that the compound is one which is capable of inhibiting HCV infection of the cell.

This invention provides a method of determining whether a compound is capable of inhibiting HCV infection of a cell which comprises:
(a) contacting an HCV envelope glycoprotein with the compound and detectable DC-SIGNR protein under conditions permitting binding of the DC-SIGNR protein to the HCV envelope glycoprotein in the absence of the compound so as to form a complex;
(b) removing unbound DC-SIGNR protein;
(c) comparing the amount of detectable DC-SIGNR protein which is bound to the HCV envelope glycoprotein in the complex in the presence of the compound with the amount of detectable DC-SIGNR protein which binds to the compound in the absence of the compound; wherein a reduced amount of DC-SIGNR protein measured in presence of the compound indicates that the compound binds to the HCV envelope glycoprotein or DC-SIGNR protein so as to thereby determine that the compound is one which is capable of inhibiting HCV infection of the cell.

This invention provides a method of obtaining a composition which comprises:
(a) identifying a compound which inhibits HCV infection of a cell according to a method described herein;
(b) recovering the compound; and
(c) admixing the compound so identified or a homolog or derivative thereof with a carrier, so as to thereby obtain a composition.

This invention provides a method of treating or preventing a liver disease in a subject which comprises administering to the subject an effective amount of a compound capable of inhibiting binding of an HCV envelope glycoprotein to a DC-SIGN protein present on the surface of the subject's cells, so as to thereby treat or prevent the liver disease in a subject.

This invention provides a method of treating or preventing a liver disease in a subject which comprises administering to the subject an effective amount of a compound capable of inhibiting binding of an HCV envelope glycoprotein to a DC-SIGNR protein present on the surface of the subject's cells, so as to thereby treat or prevent the liver disease in a subject.

This invention provides a method of treating or preventing hepatocellular carcinoma in a subject which comprises administering to the subject an effective amount of a compound capable of inhibiting binding of an HCV envelope glycoprotein to a DC-SIGN protein present on the surface of the subject's cells, so as to thereby treat or prevent hepatocellular carcinoma in a subject.

This invention provides a method of treating or preventing hepatocellular carcinoma in a subject which comprises administering to the subject an effective amount of the compound capable of inhibiting binding of an HCV envelope glycoprotein to a DC-SIGNR protein present on the surface of the subject's cells, so as to thereby treat or prevent hepatocellular carcinoma in a subject.

This invention provides a method of diagnosing HCV infection of a subject which comprises:
(a) immobilizing a DC-SIGN protein on a solid support;
(b) contacting the immobilized DC-SIGN protein with sufficient HCV envelope glycoprotein to saturate all of a portion of the binding sites for the HCV envelope glycoprotein on the immobilized DC-SIGN protein so as to form a complex;
(c) removing unbound HCV envelope glycoprotein;
(d) contacting the complex with a suitable sample obtained from the subject;
(e) removing unbound sample; and
(f) determining whether there is antibody bound to the HCV envelope glycoprotein, wherein the presence of anti-HCV antibodies thereby diagnoses HCV infection of the subject.

This invention provides a method of diagnosing HCV infection of a subject which comprises:
(a) immobilizing a DC-SIGNR protein on a solid support;
(b) contacting the immobilized DC-SIGNR protein with sufficient HCV envelope glycoprotein to saturate all or a portion of the binding sites for the HCV envelope glycoprotein on the immobilized DC-SIGNR protein so as to form a complex;
(c) removing unbound HCV envelope glycoprotein;
(d) contacting the complex with a suitable sample obtained from the subject;
(e) removing unbound sample; and
(f) determining whether there is antibody bound to the HCV envelope glycoprotein, wherein the presence of anti-HCV antibodies thereby diagnoses HCV infection of the subject.

This invention provides a method of diagnosing HCV infection of a subject which comprises:
(a) contacting DC-SIGN protein with sufficient HCV envelope glycoprotein to saturate all or a portion of the binding sites for the HCV envelope glycoprotein on the DC-SIGN protein so as to form a complex;
(b) removing unbound HCV envelope glycoprotein;
(c) contacting the complex with a suitable sample obtained from the subject;
(d) removing unbound sample; and
(e) determining whether there is antibody bound to the HCV envelope glycoprotein, wherein the presence of anti-HCV antibodies thereby diagnoses HCV infection of the subject.

This invention provides a method of diagnosing HCV infection of a subject which comprises:
(a) contacting DC-SIGNR protein with sufficient HCV envelope glycoprotein to saturate all or a portion of the binding sites for the HCV envelope glycoprotein on the DC-SIGNR protein so as to form a complex;
(b) removing unbound HCV envelope glycoprotein;
(c) contacting the complex with a suitable sample obtained from the subject;
(d) removing unbound sample; and
(e) determining whether there is antibody bound to the HCV envelope glycoprotein, wherein the presence of anti-HCV antibodies thereby diagnoses HCV infection of the subject.

This invention provides an antibody or portion thereof capable of inhibiting binding of a DC-SIGN protein to an HCV envelope glycoprotein, which antibody binds to an epitope located within a region of the DC-SIGN protein, which region of the DC-SIGN protein binds to an HCV envelope glycoprotein. In one embodiment the antibody does not inhibit HCV binding to a DC-SIGNR protein. In another embodiment the antibody does not inhibit HIV infection of a cell susceptible to HIV infection. In a further embodiment the antibody does not block ICAM adhesion.

This invention provides an antibody or portion thereof capable of inhibiting binding of a DC-SIGNR protein to an HCV envelope glycoprotein, which antibody binds to an epitope located within a region of the DC-SIGNR protein, which region of the DC-SIGNR protein binds to an HCV envelope glycoprotein. In one embodiment the antibody does not inhibit HCV binding to a DC-SIGN protein. In another embodiment the antibody does not inhibit HIV infection of a cell susceptible to HIV infection. In a further embodiment the antibody does not block ICAM adhesion.

This invention provides an antibody or portion thereof capable of inhibiting binding of a DC-SIGN protein to an HCV envelope glycoprotein, which antibody binds to an epitope located within a region of the HCV envelope glycoprotein, which region of the HCV envelope glycoprotein binds to a DC-SIGN protein. In one embodiment the antibody does not inhibit HCV binding to a DC-SIGNR protein. In another embodiment the antibody does not inhibit HIV infection of a cell susceptible to HIV infection. In a further embodiment the antibody does not block ICAM adhesion.

This invention provides an antibody or portion thereof capable of inhibiting binding of a DC-SIGN protein to an HCV envelope glycoprotein, which antibody binds to an epitope located within a region of the HCV envelope glycoprotein, which region of the HCV envelope glycoprotein binds to a DC-SIGNR protein. In one embodiment the antibody does not inhibit HCV binding to a DC-SIGN protein. In another embodiment the antibody does not inhibit HIV infection of a cell susceptible to HIV infection. In a further embodiment the antibody does not block ICAM adhesion.

This invention provides a polypeptide capable of inhibiting binding of a DC-SIGN protein to an HCV envelope glycoprotein, which polypeptide comprises consecutive amino acids having a sequence which corresponds to the sequence of at least a portion of an extracellular domain of a DC-SIGN protein, which portion binds to an HCV envelope glycoprotein. In one embodiment the polypeptide does not bind to an HIV envelope glycoprotein. In another embodiment the polypeptide does not inhibit HIV infection of a cell susceptible to an HIV infection. In a further embodiment the polypeptide does not block ICAM adhesion.

This invention provides a polypeptide capable of inhibiting binding of a DC-SIGNR protein to an HCV envelope glycoprotein, which polypeptide comprises consecutive amino acids having a sequence which corresponds to the sequence of at least a portion of an extracellular domain of a DC-SIGNR protein, which portion binds to an HCV envelope glycoprotein. In one embodiment the polypeptide does not bind to an HIV envelope glycoprotein. In another embodiment the polypeptide does not inhibit HIV infection of a cell susceptible to an HIV infection. In a further embodiment the polypeptide does not block ICAM adhesion.

This invention provides a polypeptide capable of inhibiting binding of a DC-SIGN protein to an HCV envelope glycoprotein, which polypeptide comprises consecutive amino acids having a sequence which corresponds to the sequence of at least a portion of an extracellular domain of an HCV envelope glycoprotein, which portion binds to a DC-SIGN protein.

This invention provides a polypeptide capable of inhibiting binding of a DC-SIGNR protein to an HCV envelope glycoprotein, which polypeptide comprises consecutive amino acids having a sequence which corresponds to the sequence of at least a portion of an extracellular domain of an HCV envelope glycoprotein, which portion binds to a DC-SIGNR protein.

This invention provides a nonpeptidyl agent capable of inhibiting binding of a DC-SIGN protein to an HCV envelope glycoprotein, which nonpeptidyl binds to an epitope located within a region of the DC-SIGN protein, which region of the DC-SIGN protein binds to an HCV envelope glycoprotein. In one embodiment the nonpeptidyl agent does not inhibit HCV binding to a DC-SIGNR protein. In another embodiment the nonpeptidyl agent does not inhibit HIV infection of a cell susceptible to HIV infection. In a further embodiment the nonpeptidyl agent does not block ICAM adhesion.

This invention provides a nonpeptidyl agent capable of inhibiting binding of a DC-SIGNR protein to an HCV envelope glycoprotein, which nonpeptidyl binds to an epitope located within a region of the DC-SIGNR protein, which region of the DC-SIGNR protein binds to an HCV envelope glycoprotein. In one embodiment the nonpeptidyl agent does not inhibit HCV binding to a DC-SIGN protein. In another embodiment the nonpeptidyl agent does not inhibit HIV infection of a cell susceptible to HIV infection. In a further embodiment the nonpeptidyl agent does not block ICAM adhesion.

This invention provides a nonpeptidyl agent capable of inhibiting binding of a DC-SIGN protein to an HCV envelope glycoprotein, which nonpeptidyl agent binds to at least a portion of an extracellular domain of an HCV envelope glycoprotein, which portion binds to a DC-SIGN protein. In one embodiment the nonpeptidyl agent does not inhibit HCV binding to a DC-SIGNR protein. In another embodiment the nonpeptidyl agent does not inhibit HIV infection of a cell susceptible to an HIV infection. In a further embodiment the nonpeptidyl agent does not block ICAM adhesion.

This invention provides a nonpeptidyl agent capable of inhibiting binding of a DC-SIGNR protein to an HCV envelope glycoprotein, which nonpeptidyl agent binds to at least a portion of an extracellular domain of an HCV envelope glycoprotein, which portion binds to a DC-SIGNR protein. In one embodiment the nonpeptidyl agent does not inhibit HCV binding to a DC-SIGN protein. In another embodiment the nonpeptidyl agent does not inhibit HIV infection of a cell susceptible to HIV infection. In a further embodiment the nonpeptidyl agent does not block ICAM adhesion.

This invention provides a composition which comprises a antibody or portion thereof, polypeptide and/or nonpeptide agent described herein and a carrier. In one embodiment the composition further comprises mannan, a calcium chelator or combinations thereof.

BRIEF DESCRIPTION OF THE FIGURES

FIG. 1

Figure 4:
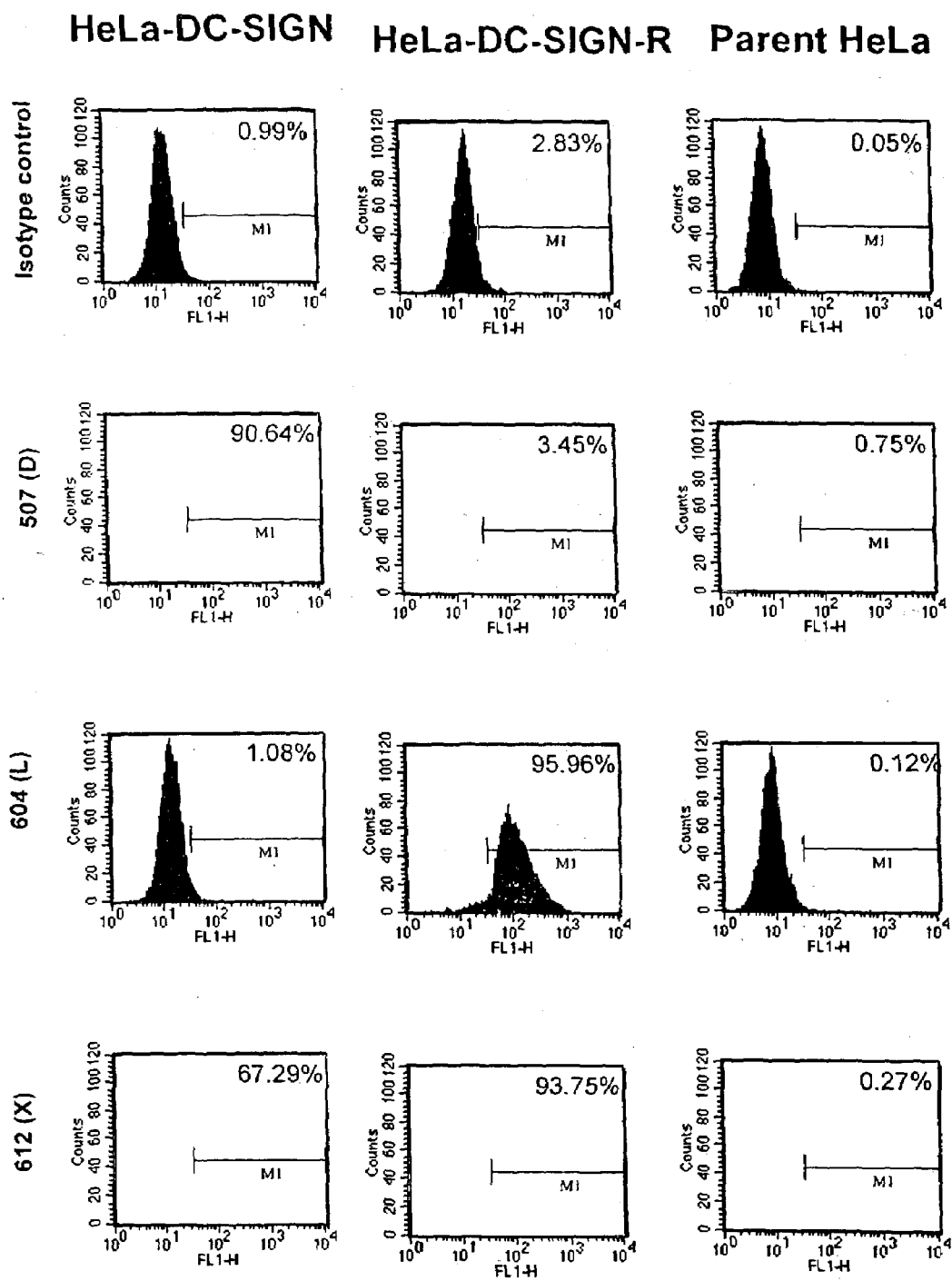

Amino acid sequence for homo sapien DC-SIGN as set forth in Genbank No. AAK20997 (SEQ ID NO:1).

FIG. 2

Amino acid sequence for homo sapien DC-SIGNR as set forth in Genbank No. AAG13848 (SEQ ID NO:2).

FIG. 3

Amino acid sequence for Hepatitis C Virus polyprotein gene as set forth in Genbank No. AF009606 (SEQ ID NO:3).

FIG. 4

Characterization of HeLa-DC-SIGN and HeLa-DC-SIGN-R cell lines using antibodies specific for DC-SIGN (507(D)), DC-SIGN-R (604(L)) or both molecules (612(X)).

FIG. 5

DC-SIGN and DC-SIGNR transfectants bind HCV-E2. (A) HeLa-DC-SIGN, (B) HeLa-DC-SIGNR and (C) parental HeLa cells were allowed to bind to HCV-E2-coated beads that were prepared by conjugation with a panel of anti-E2 mAbs. Adhesion was quantified by FACS analysis, and was blocked by mannan (20 µg/ml), and one representative experiment out of three is shown.

FIG. 6

Effect of mAbs on adhesion of HCV-E2 to DC-SIGN or DC-SIGNR. HeLa cells expressing DC-SIGN or DC-SIGNR were incubated with mAbs or mannan as described, and H53-conjugated E2 beads were added at a 20:1 bead to cell ratio. Binding was quantified by fluorescence using FACScan machine and results normalized to control (IgG2a) levels.

DETAILED DESCRIPTION OF THE INVENTION

This invention provides a method of inhibiting HCV infection of a cell susceptible to HCV infection which comprises contacting the cell with an amount of a compound effective to inhibit binding of an HCV envelope glycoprotein to a DC-SIGN protein present on the surface of the cell, so as to thereby inhibit HCV infection of the cell susceptible to HCV infection. This invention provides a method of inhibiting HCV infection of a cell susceptible to HCV infection which comprises contacting the cell with an amount of a compound effective to inhibit binding of an HCV envelope glycoprotein to a DC-SIGNR protein present on the surface of the cell, so as to thereby inhibit HCV infection of the cell susceptible to HCV infection.

Cells which are susceptible to HCV infection may bind virus through DC-SIGN and/or DC-SIGNR molecules. In addition, cells which are not susceptible to HCV infection may bind virus through DC-SIGN and/or DC-SIGNR molecules. Bound virus is then transmitted to a second susceptible target cell in trans. Accordingly, this invention provides a method of inhibiting the initial attachment of virus to a DC-SIGN and/or DC-SIGNR expressing, non-susceptible cell, and then this results in the prevention of subsequent infection of the susceptible target cell. This invention provides a method of inhibiting HCV infection of a target cell whose susceptibility to HCV infection is increased when HCV binds to a second cell which is DC-SIGN protein expressing cell, which method comprises contacting the DC-SIGN protein expressing cell with an amount of a compound effective to inhibit binding of an HCV envelope glycoprotein to a DC-SIGN protein, so as to thereby inhibiting HCV infection of the target cell. This invention provides a method of inhibiting HCV infection of a target cell whose susceptibility to HCV infection is increased when HCV binds to a second cell which is a DC-SIGNR protein expressing cell, which method comprises contacting the DC-SIGNR protein expressing cell with an amount of a compound effective to inhibit binding of an HCV envelope glycoprotein to a DC-SIGN protein, so as to thereby inhibiting HCV infection of the target cell.

This invention provides a method of inhibiting HCV infection of a target cell which does not express a DC-SIGN and/or DC-SIGNR receptor on its surface which comprises contacting a second cell that does express a DC-SIGN and/or DC-SIGNR receptor on its surface with an amount of a compound described herein effective to inhibit binding of HCV to the DC-SIGN and/or DC-SIGNR receptor so as to thereby inhibit HCV infection of the first target cell in trans. In one embodiment of this method, the target cell is present in a subject and the contacting is effected by administering the compound to the subject. In one embodiment, the target cell which does not express the DC-SIGN and/or DC-SIGNR receptor and the second cell which does express the DC-SIGN and/or DC-SIGNR receptor are neighboring. In one embodiment, the target cell and the second cell are adjacent. In another embodiment, the target cell and the second cell are not neighboring. In one embodiment, the target cell and the second cell are less than 1 Å apart, at least 1 Å apart, at least 10 Å apart, at least 100 Å apart, at least 1 nm apart, at least 10 nm apart, at least 100 nm apart, at least 1 µm apart, at least 10 µm apart, at least 100 µm apart, at least 1 mm apart, at least 1 cm apart, at least 10 cm apart, and at least 100 cm apart, at least 1 meter apart.

As used herein, "HCV" means the Hepatitis C Virus. HCV includes but is not limited to extracellular virus particles and the forms of RCV associated with and/or found in HCV infected cells. As used herein, a "cell expressing an HCV envelope glycoprotein on its surface" may also be denoted as an "HCV envelope glycoprotein$^+$ cell." As used herein, "HCV infection" means the introduction of HCV genetic information into a target cell, such as.by fusion of the target cell membrane with HCV or an HCV envelope glycoprotein$^+$ cell. The target cell may be a bodily cell of a subject. In one embodiment, the target cell is a bodily cell from a subject, such as from a human subject. As used herein, "inhibiting HCV infection" means the reduction of the amount of HCV genetic information introduced into a target cell population as compared to the amount that would be introduced without, for example, an inhibiting agent. As used herein, "inhibits" means that the amount is reduced as compared with the amount that would occur in a control sample. For example, a control sample may be one which does not contain the inhibiting agent and therefore, there would be no inhibition of HCV infection. In a preferred embodiment, inhibits means that the amount is reduced 100%. As used herein, "fusion" means the joining or union of the lipid bilayer membranes found on mammalian cells or viruses such as HCV. This process is distinguished from the attachment of HCV to a target cell. Attachment is mediated by the binding of the HCV exterior glycoprotein to a ligand present on the surface of a cell susceptible to HCV infection. As used herein, such ligand includes DC-SIGN and or DC-SIGNR. As used herein, the fusion of cell membrane of the cell susceptible to HCV infection with HCV envelope glycoprotein$^+$ cell membrane means the hydrophobic joining and integration of the cell membrane of the infection susceptible cell with HCV envelope glycoprotein$^+$ cell to form a hybrid membrane comprising components of both cell membranes. As used herein, "attachment" means the process that is mediated by the binding of the HCV envelope glycoprotein to a ligand present on the surface of a cell susceptible to HCV infection. As used herein, "inhibiting fusion of an HCV envelope glycoprotein$^+$ cell with a cell susceptible to HCV infection" means (a) reducing the rate of fusion of a cell membrane of a cell susceptible to HCV infection with a cell membrane of an HCV envelope glycoprotein$^+$ cell by at least 5%, or (b) reducing by at least 5% the total amount of fusion of a cell membrane of a cell susceptible to HCV infection with an HCV envelope glycoprotein$^+$ cell membrane occurring by the endpoint of fusion. As used herein, the rate of cell membrane fusion means the total quantity of cell membrane fused per unit of time. As used herein, the "endpoint of fusion" means the point in time at which all fusion of cell membranes of cells susceptible to HCV infection with HCV envelope glycoprotein$^+$ cell membrane capable of occurring has occurred. As used herein, a "cell susceptible to HCV infection" may also be referred to as a "target cell" and includes cells capable of being infected by or fusing with HCV or HCV infected cells. As used herein, the word "cell" includes a biological cell, e.g., a HeLa cell, and a non-biological cell, e.g., a lipid vesicle (e.g., a phospholipid vesicle) or virion.

In one embodiment of the methods described herein, the compound is an antibody or portion of an antibody. In one embodiment, the antibody is a monoclonal antibody. In one embodiment, the antibody is a polyclonal antibody.

In one embodiment, the antibody is a humanized antibody. In one embodiment, the antibody is a chimeric antibody. In one embodiment, the portion of the antibody comprises a light chain of the antibody. In one embodiment, the portion of the antibody comprises a heavy chain of the antibody. In one embodiment, the portion of the antibody comprises a Fab portion of the antibody. In one embodiment, the portion of the antibody comprises a F(ab')$_2$ portion of the antibody. In one embodiment, the portion of the antibody comprises a Fd portion of the antibody. In one embodiment, the portion of the antibody comprises a Fv portion of the antibody. In one embodiment, the portion of the antibody comprises a variable domain of the antibody. In one embodiment, the portion of the antibody comprises one or more CDR domains of the antibody.

In one embodiment of the methods described herein, the compound is a polypeptide. In one embodiment, the compound is a peptide. In one embodiment, the compound is an oligopeptide.

In one embodiment of the methods described herein, the compound is nonpeptidyl agent. In one embodiment, nonpeptidyl agent is a carbohydrate. Such carbohydrate may be any carbohydrate known to one skilled in the art including but not limited to mannose, mannan or methyl-α-D-mannopyranoside. In one embodiment of the methods described herein, the compound is a small molecule or small molecular weight molecule. In one embodiment, the compound has a molecular weight less than 500 daltons.

In one embodiment of the methods described herein, the HCV envelope glycoprotein is an HCV E1 envelope glycoprotein. In one embodiment of the methods described herein, the HCV envelope glycoprotein is an HCV E2 envelope glycoprotein.

In one embodiment of the methods described herein, the cell is present in a subject and the contacting is effected by administering the agent to the subject. Accordingly, the subject invention has various applications which includes HCV treatment such as treating a subject who has become afflicted with HCV. As used herein, "afflicted with HCV" means that the subject has at least one cell which has been infected by HCV. As used herein, "treating" means either slowing, stopping or reversing the progression of an HCV disorder. In the preferred embodiment, "treating" means reversing the progression to the point of eliminating the disorder. As used herein, "treating" also means the reduction of the number of viral infections, reduction of the number of infectious viral particles, reduction of the number of virally infected cells, or the amelioration of symptoms associated with HCV. Another application of the subject invention is to prevent a subject from contracting HCV. As used herein, "contracting HCV" means becoming infected with HCV, whose genetic information replicates in and/or incorporates into the host cells. Another application of the subject invention is to treat a subject who has become infected with HCV. As used herein, "HCV infection" means the introduction of HCV genetic information into a target cell, such as by fusion of the target cell membrane with HCV or an HCV envelope glycoprotein$^+$ cell. The target cell may be a bodily cell of a subject. In the preferred embodiment, the target cell is a bodily cell from a human subject. Another application of the subject invention is to inhibit HCV infection. As used herein, "inhibiting HCV infection" means reducing the amount of HCV genetic information introduced into a target cell population as compared to the amount that would be introduced without said composition.

As for the amount of the compound and/or agent for administration to the subject, one skilled in the art would know how to determine the appropriate amount. As used herein, a dose or amount would be one in sufficient quantities to either inhibit HCV infection, treat HCV infection, treat the subject or prevent the subject from becoming infected with HCV. This amount may be considered an effective amount. A person of ordinary skill in the art can perform simple titration experiments to determine what amount is required to treat the subject. The dose of the composition of the invention will vary depending on the subject and upon the particular route of administration used. In one embodiment, the dosage can range from about 0.1 to about 100,000 µg/kg body weight of the subject. Based upon the composition, the dose can be delivered continuously, such as by continuous pump, or at periodic intervals. For example, on one or more separate occasions. Desired time intervals of multiple doses of a particular composition can be determined without undue experimentation by one skilled in the art.

In one embodiment of the methods described herein, the effective amount of the compound is between about 1 mg and about 50 mg per kg body weight of the subject. In one embodiment, the effective amount of the compound is between about 2 mg and about 40 mg per kg body weight of the subject. In one embodiment, the effective amount of the compound is between about 3 mg and about 30 mg per kg body weight of the subject. In one embodiment, the effective amount of the compound is between about 4 mg and about 20 mg per kg body weight of the subject. In one embodiment, the effective amount of the compound is between about 5 mg and about 10 mg per kg body weight of the subject. The effective amount of the compound may comprise from about 0.000001 mg/kg body weight to about 100 mg/kg body weight. In one embodiment, the effective amount may comprise from about 0.001 mg/kg body weight to about 50 mg/kg body weight. In another embodiment, the effective amount may range from about 0.01 mg/kg body weight to about 10 mg/kg body weight. The effective amount may be based upon, among other things, the size of the compound, the biodegradability of the compound, the bioactivity of the compound and the bioavailability of the compound. If the compound does not degrade quickly, is bioavailable and highly active, a smaller amount will be required to be effective. The effective amount will be known to one of skill in the art; it will also be dependent upon the form of the compound, the size of the compound and the bioactivity of the compound. One of skill in the art could routinely perform empirical activity tests for a compound to determine the bioactivity in bioassays and thus determine the effective amount. In one embodiment of the above methods, the effective amount of the compound comprises from about 1.0 ng/kg to about 100 mg/kg body weight of the subject. In another embodiment of the above methods, the effective amount of the compound comprises from about 100 ng/kg to about 50 mg/kg body weight of the subject. In another embodiment of the above methods, the effective amount of the compound comprises from about 1 µg/kg to about 10 mg/kg body weight of the subject. In another embodiment of the above methods, the effective amount of the compound comprises from about 100 µg/kg to about 1 mg/kg body weight of the subject.

As for when the compound and/or agent is to be administered, one skilled in the art can determine when to administer such compound and/or agent. The administration may be constant for a certain period of time or periodic and at specific intervals. The compound may be delivered hourly, daily, weekly, monthly, yearly (e.g. in a time release form) or as a one time delivery. The delivery may be continuous delivery for a period of time, e.g. intravenous delivery. In one embodiment of the methods described herein, the agent is administered at least once per day. In one embodiment of the methods described herein, the agent is administered daily. In one embodiment of the methods described herein, the agent is administered every other day. In one embodiment of the methods described herein, the agent is administered every 6 to 8 days. In one embodiment of the methods described herein, the agent is administered weekly.

As used herein, "subject" means any animal or artificially modified animal capable of becoming HCV-infected. The subjects include but are mot limited to a human being, a primate, an equine, an opine, an avian, a bovine, a porcine, a canine, a feline or a mouse. Artificially modified animals include, but are not limited to, SCID mice with human immune systems. The animals include but are not limited to mice, rats, dogs, guinea pigs, ferrets, rabbits, and primates. In the preferred embodiment, the subject is a human being. The subject may be an "HCV-infected subject" which is a subject having at least one of his or her own cells invaded by HCV. In the preferred embodiment, the HCV infected subject is a human being. The subject may be a "non-HCV-infected subject" which is a subject not having any of his own cells invaded by HCV. In the preferred embodiment, the non-HCV infected subject is a human being.

As used herein, "administering" may be effected or performed using any of the methods known to one skilled in the art. The compound may be administered by various routes including but not limited to aerosol, intravenous, oral or topical route. The administration may comprise intralesional, intraperitoneal, subcutaneous, intramuscular or intravenous injection; infusion; liposome-mediated delivery; topical, intrathecal, gingival pocket, per rectum, intrabronchial, nasal, transmucosal, intestinal, oral, ocular or otic delivery. In a further embodiment, the administration includes intrabronchial administration, anal, intrathecal administration or transdermal delivery. The compounds and/or agents of the subject invention may be delivered locally via a capsule which allows sustained release of the agent or the peptide over a period of time. Controlled or sustained release compositions include formulation in lipophilic depots (e.g., fatty acids, waxes, oils). Also comprehended by the invention are particulate compositions coated with polymers (e.g., poloxamers or poloxamines) and the agent coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

The carrier may be a diluent, an aerosol, a topical carrier, an aqueous solution, a nonaqueous solution or a solid carrier.

This invention provides a method of treating HCV infection in a subject which comprises inhibiting HCV infection of the subject's cells susceptible to HCV infection by a method described herein, wherein the contacting is effected by administering the compound to the subject. This invention provides a method of preventing HCV infection of a subject which comprises inhibiting HCV infection of the subject's cells susceptible to HCV infection by a method described herein, wherein the contacting is effected by administering the compound to the subject. This invention provides a method of preventing a cell or cells of a subject from becoming infected with HCV which comprises administering to the subject an amount of one of the compounds described herein effective to inhibit binding of HCV to DC-SIGN and/or DC-SIGNR receptors on the surface of the subject's cells so as to thereby prevent the subject's cell or cells from becoming infected with HCV. This invention provides a method of treating a subject whose cells are infected with HCV which comprises administering to the subject an amount of one of the compounds described herein effective to inhibit binding of HCV to DC-SIGN and/or DC-SIGNR receptors on the surface of the subject's cells so as to thereby treat the subject. In a preferred embodiment, the subject is a human. In another embodiment, the subject is a SCID-BNX mouse (Galun et al., J. Inf. Dis. 172:25, 1995).

In one embodiment of the above methods, the subject is infected with HCV prior to administering the compound to the subject. In one embodiment of the above methods, the subject is not infected with HCV prior to administering the compound to the subject. In one embodiment of the above methods, the subject is not infected with, but has been exposed to, HCV.

In one embodiment of the methods described herein, the cell susceptible to HCV infection is a primary cell. In one embodiment, the cell is a dendritic cell, placental cell or endometrial cell. In one embodiment, the cell is a liver cell, lymph node cell, endometrial cell in liver or placenta cell. In one embodiment of the methods described herein, the cell susceptible to HCV infection is a eucaryotic cell. In one embodiment of the methods described herein, the cell susceptible to HCV infection is a human cell. In one embodiment of the methods described herein, the cell susceptible to HCV infection is a peripheral blood mononuclear cell. In one embodiment of the methods described herein, the cell susceptible to HCV infection is a HeLa cell. In one embodiment of the methods described herein, the cell susceptible to HCV infection is a hepatic cell. A hepatic cell may include but is not limited to a HepG2 cell, SK-HEP1 cell, C3A cell or an Huh-7 cell. In one embodiment, the hepatic cell is a primary hepatic cell.

This invention provides a method of treating a subject afflicted with HCV which comprises administering to the subject an effective dose of an agent of composition described herein. In one embodiment, the agent or composition may be enough to decrease the subject's viral load. As used herein, "treating" means either slowing, stopping or reversing the progression of an HCV disorder. In the preferred embodiment, "treating" means reversing the progression to the point of eliminating the disorder. As used herein, "treating" also means the reduction of the number of viral infections, reduction of the number of infectious viral particles, reduction of the number of virally infected cells, or the amelioration of symptoms associated with HCV. As used herein, "afflicted with HCV" means that the subject has at least one cell which has been infected by HCV.

This invention provides a method of preventing a subject from contracting HCV which comprises administering to the subject an effective dose of an agent or composition described herein.

This invention provides a use of a compound and/or agent described herein, such as an antibody or portion thereof, peptide, polypeptide or oligopeptide, or nonpeptidyl agent for the preparation of a pharmaceutical composition for inhibiting HCV infection of a cell susceptible to HCV infection. This invention provides a use of a compound and/or agent described herein, such as an antibody or portion thereof, peptide, polypeptide or oligopeptide, or nonpeptidyl agent for the preparation of a pharmaceutical composition for treating HCV infection in a subject. This invention provides a use of a compound and/or agent described herein, such as an antibody or portion thereof, peptide, polypeptide or oligopeptide, or nonpeptidyl agent for the preparation of a pharmaceutical composition for preventing HCV infection in a subject.

This invention provides a method of determining whether a compound is capable of inhibiting HCV infection of a cell which comprises:
a) immobilizing an HCV envelope glycoprotein on a solid support;
b) contacting the immobilized HCV envelope glycoprotein with sufficient detectable DC-SIGN protein to saturate all binding sites for the DC-SIGN protein on the immobilized HCV envelope glycoprotein under conditions permitting binding of the DC-SIGN protein to the immobilized HCV envelope glycoprotein so as to form a complex;
c) removing unbound DC-SIGN protein;
d) contacting the complex with the compound; and
e) determining whether any DC-SIGN protein is displaced from the complex, wherein displacement of DC-SIGN protein from the complex indicates that the compound binds to the HCV envelope glycoprotein, so as to thereby determine that the compound is one which is capable of inhibiting HCV infection of the cell.

This invention provides a method of determining whether a compound is capable of inhibiting HCV infection of a cell which comprises:
a) immobilizing an HCV envelope glycoprotein on a solid support;
b) contacting the immobilized HCV envelope glycoprotein with sufficient detectable DC-SIGNR protein to saturate all binding sites for the DC-SIGNR protein on the immobilized HCV envelope glycoprotein under conditions permitting binding of the DC-SIGNR protein to the immobilized HCV envelope glycoprotein so as to form a complex;
c) removing unbound DC-SIGNR protein;
d) contacting the complex with the compound;
e) determining whether any DC-SIGNR protein is displaced from the complex, wherein displacement of DC-SIGNR protein from the complex indicates that the compound binds to the HCV envelope glycoprotein, so as to thereby determine that the compound is one which is capable of inhibiting HCV infection of the cell.

This invention provides a method of determining whether a compound is capable of inhibiting HCV infection of a cell which comprises:
a) immobilizing a DC-SIGN protein on a solid support;
b) contacting the immobilized DC-SIGN protein with sufficient detectable HCV envelope glycoprotein to saturate all binding sites for the HCV envelope glycoprotein on the immobilized DC-SIGN protein under conditions permitting binding of the immobilized DC-SIGN protein to the HCV envelope glycoprotein so as to form a complex;
c) removing unbound HCV envelope glycoprotein;
d) contacting the complex with the compound;
e) determining whether any HCV envelope glycoprotein is displaced from the complex, wherein displacement of HCV envelope glycoprotein from the complex indicates that the compound binds to the DC-SIGN protein, so as to thereby determine that the compound is one which is capable of inhibiting HCV infection of the cell.

This invention provides a method of determining whether a compound is capable of inhibiting HCV infection of a cell which comprises:
a) immobilizing a DC-SIGNR protein on a solid support;
b) contacting the immobilized DC-SIGNR protein with sufficient detectable HCV envelope glycoprotein to saturate all binding sites for the HCV envelope glycoprotein on the immobilized DC-SIGNR protein under conditions permitting binding of the immobilized DC-SIGNR protein to the HCV envelope glycoprotein so as to form a complex;
c) removing unbound HCV envelope glycoprotein;
d) contacting the complex with the compound;
e) determining whether any HCV envelope glycoprotein is displaced from the complex, wherein displacement of HCV envelope glycoprotein from the complex indicates that the compound binds to the DC-SIGNR protein, so as to thereby determine that the compound is one which is capable of inhibiting HCV infection of the cell.

This invention provides a method of determining whether a compound is capable of inhibiting HCV infection of a cell which comprises:
(a) contacting an HCV envelope glycoprotein with sufficient detectable DC-SIGN protein to saturate all binding sites for the DC-SIGN protein on the HCV envelope glycoprotein under conditions permitting binding of the DC-SIGN protein to the HCV envelope glycoprotein so as to form a complex;
(b) removing unbound DC-SIGN protein;
(c) measuring the amount of DC-SIGN protein which is bound to the HCV envelope glycoprotein in the complex;
(d) contacting the complex with the compound so as to displace DC-SIGN protein from the complex;
(e) measuring the amount of DC-SIGN protein which is bound to the compound in the presence of the compound; and
(f) comparing the amount of DC-SIGN protein bound to the HCV envelope glycoprotein in step (e) with the amount measured in step (c), wherein a reduced amount measured in step (e) indicates that the compound binds to the HCV envelope glycoprotein, so as to thereby determine that the compound is one which is capable of inhibiting HCV infection of the cell.

This invention provides a method of determining whether a compound is capable of inhibiting HCV infection of a cell which comprises:
(a) contacting an HCV envelope glycoprotein with sufficient detectable DC-SIGNR protein to saturate all binding sites for the DC-SIGNR protein on the HCV envelope glycoprotein under conditions permitting binding of the DC-SIGNR protein to the HCV envelope glycoprotein so as to form a complex;
(b) removing unbound DC-SIGNR protein;
(c) measuring the amount of DC-SIGNR protein which is bound to the HCV envelope glycoprotein in the complex;
(d) contacting the complex with the compound so as to displace DC-SIGNR protein from the complex;
(e) measuring the amount of DC-SIGNR protein which is bound to the compound in the presence of the compound; and
(f) comparing the amount of DC-SIGNR protein bound to the HCV envelope glycoprotein in step (e) with the amount measured in step (c), wherein a reduced amount measured in step (e) indicates that the compound binds to the HCV envelope glycoprotein so as to thereby identify the compound as one which is capable of inhibiting HCV infection of a cell.

This invention provides a method of determining whether a compound is capable of inhibiting HCV infection of a cell which comprises:
(a) immobilizing an HCV envelope glycoprotein on a solid support;
(b) contacting the immobilized HCV envelope glycoprotein with the compound and detectable DC-SIGN protein under conditions permitting binding of the DC-SIGN protein to the immobilized HCV envelope glycoprotein so as to form a complex;
(c) removing unbound DC-SIGN protein;
(d) comparing the amount of detectable DC-SIGN protein which is bound to the immobilized HCV envelope glycoprotein in the complex in the presence of the compound with the amount of detectable DC-SIGN protein which binds to the immobilized HCV envelope glycoprotein in the absence of the compound;
(e) wherein a reduced amount of DC-SIGN protein measured in the presence of the compound indicates that the compound binds to the HCV envelope glycoprotein or the DC-SIGN protein, so as to thereby determine that the compound is one which is capable of inhibiting HCV infection of the cell.

In one embodiment of the methods described herein, the amount of the detectable DC-SIGN is sufficient to saturate all binding sites for the DC-SIGN protein on the HCV envelope glycoprotein.

This invention provides a method of determining whether a compound is capable of inhibiting HCV infection of a cell which comprises:
(a) immobilizing an HCV envelope glycoprotein on a solid support;
(b) contacting the immobilized HCV envelope glycoprotein with the compound and detectable DC-SIGNR protein under conditions permitting binding of the DC-SIGNR protein to the immobilized HCV envelope glycoprotein so as to form a complex;
(c) removing unbound DC-SIGNR protein;
(d) comparing the amount of detectable DC-SIGNR protein which is bound to the immobilized HCV envelope glycoprotein in the complex in the presence of the compound with the amount of detectable DC-SIGNR protein which binds to the immobilized HCV envelope glycoprotein in the absence of the compound;
(e) wherein a reduced amount of DC-SIGNR protein measured in the presence of the compound indicates that the compound binds to the HCV envelope glycoprotein or the DC-SIGNR protein, so as to thereby determine that the compound is one which is capable of inhibiting HCV infection of the cell.

In one embodiment of the methods described herein, the amount of the detectable DC-SIGNR is sufficient to saturate all binding sites for the DC-SIGNR protein on the HCV envelope glycoprotein.

This invention provides a method of determining whether a compound is capable of inhibiting HCV infection of a cell which comprises:
(a) immobilizing a DC-SIGN protein on a solid support;
(b) contacting the immobilized DC-SIGN protein with the compound and detectable HCV envelope glycoprotein under conditions permitting binding of the immobilized DC-SIGN protein to the HCV envelope glycoprotein so as to form a complex;
(c) removing unbound HCV envelope glycoprotein;
(d) comparing the amount of detectable HCV envelope glycoprotein which is bound to the immobilized DC-SIGN protein in the complex in the presence of the compound with the amount of detectable HCV envelope glycoprotein which binds to the immobilized DC-SIGN protein in the absence of the compound;
(e) wherein a reduced amount of HCV envelope glycoprotein measured in the presence of the compound indicates that the compound binds to the HCV envelope glycoprotein or the DC-SIGN protein, so as to thereby determine that the compound is one which is capable of inhibiting HCV infection of the cell.

In one embodiment of the methods described herein, the amount of the detectable HCV envelope glycoprotein is sufficient to saturate all binding sites for the HCV envelope glycoprotein on the DC-SIGN protein.

This invention provides a method of determining whether a compound is capable of inhibiting HCV infection of a cell which comprises:
(a) immobilizing a DC-SIGNR protein on a solid support;
(b) contacting the immobilized DC-SIGNR protein with the compound and detectable HCV envelope glycoprotein under conditions permitting binding of the immobilized DC-SIGNR protein to the HCV envelope glycoprotein so as to form a complex;
(c) removing unbound HCV envelope glycoprotein;
(d) comparing the amount of detectable HCV envelope glycoprotein which is bound to the immobilized DC-SIGNR protein in the complex in the presence of the compound with the amount of detectable HCV envelope glycoprotein which binds to the immobilized DC-SIGNR protein in the absence of the compound;
(e) wherein a reduced amount of HCV envelope glycoprotein measured in the presence of the compound indicates that the compound binds to the HCV envelope glycoprotein or the DC-SIGNR protein, so as to thereby determine that the compound is one which is capable of inhibiting HCV infection of the cell.

In one embodiment of the methods described herein, the amount of the detectable HCV envelope glycoprotein is sufficient to saturate all binding sites for the HCV envelope glycoprotein on the DC-SIGNR protein.

This invention provides a method of determining whether a compound is capable of inhibiting HCV infection of a cell which comprises:
(a) contacting an HCV envelope glycoprotein with the compound and detectable DC-SIGN protein under conditions permitting binding of the DC-SIGN protein to the HCV envelope glycoprotein so as to form a complex;
(b) removing unbound DC-SIGN protein;
(c) comparing the amount of detectable DC-SIGN protein which is bound to the HCV envelope glycoprotein in the complex in the presence of the compound with the amount of detectable DC-SIGN protein which binds to the compound in the absence of the compound; wherein a reduced amount of DC-SIGN protein measured in presence of the compound indicates that the compound binds to the HCV envelope glycoprotein or DC-SIGN protein so as to thereby determine that the compound is one which is capable of inhibiting HCV infection of the cell.

In one embodiment of the methods described herein, the amount of the detectable DC-SIGN protein is sufficient to saturate all binding sites for the DC-SIGN protein on the HCV envelope glycoprotein.

This invention provides a method of determining whether a compound is capable of inhibiting HCV infection of a cell which comprises:
(a) contacting an HCV envelope glycoprotein with the compound and detectable DC-SIGNR protein under conditions permitting binding of the DC-SIGNR protein to the HCV envelope glycoprotein so as to form a complex;
(b) removing unbound DC-SIGNR protein;
(c) comparing the amount of detectable DC-SIGNR protein which is bound to the HCV envelope glycoprotein in the complex in the presence of the compound with the amount of detectable DC-SIGNR protein which binds to the compound in the absence of the compound; wherein a reduced amount of DC-SIGN protein measured in presence of the compound indicates that the compound binds to the HCV envelope glycoprotein or DC-SIGNR protein so as to thereby determine that the compound is one which is capable of inhibiting HCV infection of the cell.

In one embodiment of the methods described herein, the amount of the detectable DC-SIGNR protein is sufficient to saturate all binding sites for the DC-SIGNR protein on the HCV envelope glycoprotein.

In the methods described herein, an entity may be made detectable by labeling it with a detectable marker. For example, In one embodiment of the methods described herein, the detectable DC-SIGN protein is labeled with a detectable marker. In one embodiment of the methods described herein, the detectable DC-SIGNR protein is labeled with a detectable marker. In one embodiment of the methods described herein, the detectable HCV envelope glycoprotein is labeled with a detectable marker. One skilled in the art would know various types of detectable markers. Such detectable markers include but are not limited to a radioactive, calorimetric, luminescent and fluorescent markers.

This invention provides a method of identifying an agent which inhibits binding of HCV to DC-SIGN which comprises:
(a) immobilizing one or both of the HCV envelope glycoproteins on a solid support;
(b) contacting the result from step (a) with the agent;
(c) contacting the result from step (c) with a detectable form of DC-SIGN protein under conditions that permit binding of the detectable DC-SIGN protein in the absence of the compound;
(d) detecting the amount of bound detectable DC-SIGN protein, wherein a reduction of the amount of bound detectable DC-SIGN protein compared to an amount bound in the absence of the agent thereby identifies the agent as one which inhibits binding of HCV to the DC-SIGN.

This invention provides a method of identifying an agent which inhibits binding of HCV to DC-SIGNR which comprises:
(a) immobilizing one or both of the HCV envelope glycoproteins on a solid support;
(b) contacting the result from step (a) with the agent;
(c) contacting the result from step (c) with a detectable form of DC-SIGNR protein under conditions that permit binding of the detectable DC-SIGNR protein in the absence of the compound;
(d) detecting the amount of bound detectable DC-SIGNR protein, wherein a reduction of the amount of bound detectable DC-SIGNR protein compared to an amount bound in the absence of the agent thereby identifies the agent as one which inhibits binding of HCV to the DC-SIGNR.

This invention provides a method of identifying an agent which inhibits binding of HCV to DC-SIGN which comprises:
(a) immobilizing a DC-SIGN protein on a solid support;
(b) contacting the result from step (a) with the agent
(c) contacting the result from step (b) with a detectable form of one or more of the HCV envelope glycoproteins under conditions that permit binding of the detectable HCV envelope glycoprotein(s) in the absence of the compound;
(d) detecting the amount of bound detectable HCV envelope glycoprotein(s), wherein a reduction of the amount of bound detectable HCV envelope glycoprotein(s) compared to an amount bound in the absence of the agent thereby identifies the agent as one which inhibits binding of HCV to the DC-SIGN.

This invention provides a method of identifying an agent which inhibits binding of HCV to DC-SIGNR which comprises:
(a) immobilizing a DC-SIGNR protein on a solid support;
(b) contacting the result from step (a) with the agent
(c) contacting the result from step (c) with a detectable form of one or more of the HCV envelope glycoproteins under conditions that permit binding of the detectable HCV envelope glycoprotein(s) in the absence of the compound;
(d) detecting the amount of bound detectable HCV envelope glycoprotein(s), wherein a reduction of the amount of bound detectable HCV envelope glycoprotein(s) compared to an amount bound in the absence of the agent thereby identifies the agent as one which inhibits binding of HCV to the DC-SIGNR.

In one embodiment of the method described herein, the solid support is a microtiter plate well. In another embodiment, the solid support is a bead. In a further embodiment, the solid support is a surface plasmon resonance sensor chip. The surface plasmon resonance sensor chip can have pre-immobilized streptavidin. In one embodiment, the surface plasmon resonance sensor chip is a BIAcore™ chip.

In one embodiment of the above methods, the detectable molecule is labeled with a detectable marker. In another embodiment of the above methods, the detectable molecule is detected by contacting it with another compound which is both capable of binding the detectable molecule and is detectable. The detectable markers include those described above.

As used herein, the terms "agent" and "compound" include both protein and non-protein moieties. In one embodiment, the agent/compound is a small molecule. In another embodiment, the agent/compound is a protein. The protein may be, by way of example, an antibody directed against a portion of an HCV envelope glycoprotein. The agent/compound may be derived from a library of low molecular weight compounds or a library of extracts from plants or other organisms. In an embodiment, the agent is known. In a separate embodiment, the agent/compound is not previously known. The agents/compounds of the subject invention include but are not limited to compounds or molecular entities such as peptides, polypeptides, and other organic or inorganic molecules and combinations thereof.

Compounds of the present invention inhibit HCV infection of cells susceptible to HCV infection. The compounds of the present invention preferable have specificity for preventing or inhibiting infection by HCV and do not inhibit infection by other viruses, such as HIV, that may utilize DC-SIGN or DC-SIGNR for infection. Moreover the compounds of the present invention preferably do not interfere or inhibit members of the immunoglobulin superfamily, in particular, the compounds do not interfere with ICAM-2 or ICAM-3 or with ICAM-2-like, or ICAM-3-like molecules.

As used herein, the terms "agent" and "compound" may be used interchangeably. In one embodiment of the methods described herein, the agent is an antibody or a portion of an antibody. In one embodiment of the antibody, the antibody is a monoclonal antibody. In one embodiment of the antibody, the antibody is a polyclonal antibody. In one embodiment of the antibody, the antibody is a humanized antibody. In one embodiment of the antibody, the antibody is a chimeric antibody. The portion of the antibody may comprise a light chain of the antibody. The portion of the antibody may comprise a heavy chain of the antibody. The portion of the antibody may comprise a Fab portion of the antibody. The portion of the antibody may comprise a F(ab')$_2$ portion of the antibody. The portion of the antibody may comprise a Fd portion of the antibody. The portion of the antibody may comprise a Fv portion of the antibody. The portion of the antibody may comprise a variable domain of the antibody. The portion of the antibody may comprise one or more CDR domains of the antibody.

In one embodiment of the methods described herein, the agent is a polypeptide. In one embodiment of the methods described herein, the agent is a oligopeptide. In one embodiment of the methods described herein, the agent is a non-peptidyl agent. In one embodiment, the nonpeptidyl agent is a compound having a molecular weight less than 500 daltons.

This invention provides a method of obtaining a composition which comprises:
(a) identifying a compound which inhibits HCV infection of a cell according to a method described herein;
(b) admixing the compound so identified or a homolog or derivative thereof with a carrier, so as to thereby obtain a composition.

This invention provides a method of obtaining a composition which comprises:
(a) identifying a compound which inhibits binding of HCV to DC-SIGN according to one of the methods described herein; and
(b) admixing the compound so identified or a homolog or derivative thereof with a carrier.

This invention provides a method of obtaining a composition which comprises:
(a) identifying a compound which inhibits binding of HCV to DC-SIGNR according to one of the above methods; and
(b) admixing the compound so identified or a homolog or derivative thereof with a carrier.

In one embodiment of these methods of obtaining a composition, this method further comprises recovering the identified compound before it is admixed with the carrier.

This invention provides a method of treating or preventing a liver disease in a subject which comprises administering to the subject an effective amount of a compound capable of inhibiting binding of an HCV envelope glycoprotein to a DC-SIGN protein present on the surface of the subject's cells, so as to thereby treat or prevent the liver disease in a subject. This invention provides a method of treating or preventing a liver disease in a subject which comprises administering to the subject an effective amount of a compound capable of inhibiting binding of an HCV envelope glycoprotein to a DC-SIGNR protein present on the surface of the subject's cells, so as to thereby treat or prevent the liver disease in a subject. In one embodiment of the methods described herein, the liver disease is hepatitis. In one embodiment of the methods described herein, the liver disease is cirrhosis.

This invention provides a method of treating or preventing hepatocellular carcinoma in a subject which comprises administering to the subject an effective amount of a compound capable of inhibiting binding of an HCV envelope glycoprotein to a DC-SIGN protein present on the surface of the subject's cells, so as to thereby treat or prevent hepatocellular carcinoma in a subject. This invention provides a method of treating or preventing hepatocellular carcinoma in a subject which comprises administering to the subject an effective amount of the compound capable of inhibiting binding of an HCV envelope glycoprotein to a DC-SIGNR protein present on the surface of the subject's cells, so as to thereby treat or prevent hepatocellular carcinoma in a subject.

This invention provides a method of diagnosing HCV infection of a subject which comprises:
(a) immobilizing a DC-SIGN protein on a solid support;
(b) contacting the immobilized DC-SIGN protein with sufficient detectable HCV envelope glycoprotein to saturate all binding sites for the HCV envelope glycoprotein on the immobilized DC-SIGN protein so as to form a complex;
(c) removing unbound HCV envelope glycoprotein;
(d) contacting the complex with a suitable sample obtained from the subject; and
(e) detecting whether any HCV envelope glycoprotein is displaced from the complex, wherein displacement of the HCV envelope glycoprotein from the complex indicates the presence of anti-HCV antibodies present in the sample, so as to thereby diagnose HCV infection of the subject.

This invention provides a method of diagnosing HCV infection of a subject which comprises:
(a) immobilizing a DC-SIGNR protein on a solid support;
(b) contacting the immobilized DC-SIGNR protein with sufficient detectable HCV envelope glycoprotein to saturate all binding sites for the HCV envelope glycoprotein on the immobilized DC-SIGNR protein so as to form a complex;
(c) removing unbound HCV envelope glycoprotein;
(d) contacting the complex with a suitable sample obtained from the subject; and
(e) detecting whether any HCV envelope glycoprotein is displaced from the complex, wherein displacement of the HCV envelope glycoprotein from the complex indicates the presence of anti-HCV antibodies present in the sample, so as to thereby diagnose HCV infection of the subject.

This invention provides a method of diagnosing HCV infection of a subject which comprises:
(a) contacting DC-SIGN protein with sufficient detectable HCV envelope glycoprotein to saturate all binding sites for the HCV envelope glycoprotein on the DC-SIGN protein so as to form a complex;
(b) removing unbound HCV envelope glycoprotein;
(c) contacting the complex with a suitable sample obtained from the subject; and
(d) detecting whether any HCV envelope glycoprotein is displaced from the complex, wherein displacement of the HCV envelope glycoprotein from the complex indicates the presence of anti-HCV antibodies present in the sample, so as to thereby diagnose HCV infection of the subject.

This invention provides a method of diagnosing HCV infection of a subject which comprises:
(a) contacting DC-SIGNR protein with sufficient detectable HCV envelope glycoprotein to saturate all binding sites for the HCV envelope glycoprotein on the DC-SIGNR protein so as to form a complex;
(b) removing unbound HCV envelope glycoprotein;
(c) contacting the complex with a suitable sample obtained from the subject; and
(d) detecting whether any HCV envelope glycoprotein is displaced from the complex, wherein displacement of the HCV envelope glycoprotein from the complex indicates the presence of anti-HCV antibodies present in the sample, so as to thereby diagnose HCV infection of the subject.

The ability of a DC-SIGN protein, a DC-SIGNR protein or functional equivalent thereof to bind to HCV permits the use of the protein as a diagnostic for HCV infection, for example in an ELISA (Enzyme linked immunosorbent assay). In one embodiment, a soluble form of a DC-SIGN protein and/or a DC-SIGNR protein could be used to detect serum antibodies to HCV. In a preferred embodiment, the DC-SIGN protein and/or DC-SIGNR protein or functional equivalent thereof is immobilized on a solid support and contacted with the HCV envelope glycoprotein(s), which may be an E1 HCV envelope glycoprotein, an E2 HCV envelope glycoprotein, or both. The contacting may occur in the presence or absence of serum or serum antibodies. In an assay of this form, competitive binding between antibodies and the HCV glycoprotein(s) for binding to the immobilized protein thereof results in the bound HCV protein being a measure of antibodies in the serum sample, most particularly. The amount of bound HCV glycoprotein(s) is then detected. The HCV glycoprotein(s) may be labeled with radioactive, enzymatic, biotin, fluorescent or other detectable marker to facilitate detection.

This invention provides methods of diagnosing HCV infection in a subject employing a method known to one skilled in the art, including but not limited to a sandwich assay and a competition assay.

For example, one embodiment of a sandwich assay is as follows:
(5) obtain a suitable sample of DC-SIGN and/or DC-SIGNR protein;
(2) contact the DC-SIGN and/or DC-SIGNR protein with an HCV envelope glycoprotein, so as to form a complex;
(3) obtain a suitable sample from the subject and contact the HCV envelope glycoprotein with the sample, under conditions permitting formation of a complex between the HCV envelope glycoprotein and any anti-HCV envelope glycoprotein antibodies present in the subject's sample;
(4) contacting the bound anti-HCV envelope glycoprotein antibodies with detectable anti-human IgG antibodies, which would bind to any bound anti-HCV envelope glycoprotein antibodies;
(5) detecting the anti-human IgG antibodies, wherein the presence of such antibodies indicates that the subject is HCV infected.

For example, one embodiment of a competition assay is as follows:
(1) obtaining a suitable sample of DC-SIGN and/or DC-SIGNR protein;
(2) contacting the DC-SIGN and/or DC-SIGNR protein with an HCV envelope glycoprotein, so as to form a complex;
(3) contacting the HCV envelope glycoprotein with a sample from the subject, under conditions permitting binding between any anti-HCV antibodies present in the sample and the HCV envelope glycoprotein;
(4) also contacting the HCV envelope glycoprotein with detectable anti-HCV envelope glycoprotein antibodies, under conditions permitting binding between the detectable anti-HCV envelope glycoprotein antibodies and the HCV envelope glycoprotein;
(5) determining the amount of detectable anti-HCV envelope glycoprotein antibodies bound, compared with the amount bound in the absence of any sample from the subject, wherein an increased amount measured in the absence of the sample indicates that the subject is HCV infected.

In one embodiment of the methods and assays described herein, the sample from the subject is a serum sample. In one embodiment, the DC-SIGN and/or DC-SIGNR protein is immobilized. The above methods may include wash steps so as to wash unbound compounds including nut not limited to unbound HCV envelope glycoprotein, unbound sample from the subject, unbound anti-HCV envelope glycoprotein antibodies, and unbound detectable anti-human IgG antibodies. In one embodiment, the detectable anti-human IgG antibodies are labeled with a detectable marker. In one embodiment, the detectable anti-HCV envelope antibodies are labeled with a detectable marker. In one embodiment, the amount of anti-human IgG antibodies detected is compared with an amount measured in the absence of HCV envelope glycoprotein, so as to determine a baseline measurement.

This invention provides an article of manufacture comprising a solid support having operably affixed thereto an agent capable of specifically forming a complex with a domain present on an HCV envelope glycoprotein.

The solid support may be any solid support known in the art to which the agent can be operably affixed. Solid supports include, by way of example, natural or synthetic polymers. Synthetic polymers include, by way of example, polystyrene, polyethylene and polypropylene Natural polymers include, by way of example, latex. The solid support may be selected, for example, from the group consisting of a bead, a receptacle, and a filter. Solid supports in the form of beads are widely used and readily available to those skilled in the art. Beads include, for example, latex and polystyrene beads.

The receptacle can be any receptacle in which a bodily fluid is stored, or with which such fluid comes into contact. For example, the receptacle may be in the form of a bag or tubing. In the preferred embodiment, the receptacle is a bag specifically intended for the collection and/or storage of blood or blood components.

Solid supports in the form of filters are widely used and readily available to those skilled in the art. Filters include, for example, polyester filters (e.g., polyester leukofiltration devices) and cellulose acetate filters.

The agent affixed to the solid support may either be a protein or a non-protein agent. In one embodiment, the agent is DC-SIGN and/or DC-SIGNR. In one embodiment, the agent is an antibody or portion. Such antibody may be one which is capable of binding to an HCV envelope glycoprotein.

As used herein, "operably affixed" means affixed in a manner permitting the formation of a complex between the affixed agent and the domain present on an HCV envelope glycoprotein. Methods of operably affixing an agent to a solid support are well known to those skilled in the art.

As used herein, "capable of specifically forming a complex with a domain present on an HCV envelope glycoprotein" means capable of forming a complex with a domain present on an HCV envelope glycoprotein but not capable of forming a complex with any other domain.

In one embodiment, the domain present on the HCV envelope glycoprotein is a conserved domain. As used herein, a "conserved domain" is an envelope glycoprotein domain which is present on, and whose structure is invariant among, at least 90% of all strains of HCV. In the preferred embodiment, the conserved domain present on the HCV envelope glycoprotein is the DC-SIGN and/or DC-SIGNR-binding domain of the HCV envelope glycoprotein. In another embodiment, the domain present on the HCV envelope glycoprotein is a non-conserved domain.

This invention further provides an article of manufacture comprising a solid support having operably affixed thereto a plurality of agents each capable of specifically forming a complex with a domain present on an HCV envelope glycoprotein.

As used herein, a "plurality of agents" means at least two agents. In one embodiment, the plurality of agents consists of a plurality of DC-SIGN and/or DC-SIGNR-based molecules. In another embodiment, the plurality of agents consists of a plurality of antibodies. In a further embodiment, the plurality of agents comprises an antibody and a DC-SIGN and/or DC-SIGNR-based molecule.

This invention further provides an aqueous-soluble agent which (a) is capable of specifically forming a complex with a domain present on an HCV envelope glycoprotein, and (b) comprises a moiety capable of specifically forming a complex with a known ligand, which moiety permits the removal of the agent from a sample via contact with an immobilized form of the known ligand. As used herein, "aqueous-soluble" means capable of existing in soluble form in water at 4° C. at a concentration of at least 1 pM.

The use of a moiety capable of specifically forming a complex with a known ligand is commonly referred to in the art as "molecular tagging." The moiety may be selected, for example, from the group consisting of a small molecule and a protein. The ligand includes but is not limited to for example, a metal ion, a small molecule, a peptide or a protein. Specific examples of moiety/ligand combinations include, but are not limited to, (a) oligohistidine/nickel ion, (b) glutathione S-transferase/glutathione, (c) biotin/streptavidin, and (d) the HA peptide YPYDVPDYA/anti-HA peptide antibody. The moiety may be attached by any means known to one skilled in the art, such as for example, chemically or genetically This invention further provides a method of treating a bodily fluid sample so as to remove therefrom HCV or HCV envelope glycoprotein if present in the sample which comprises contacting the sample under suitable conditions with an article of manufacture comprising a solid support having operably affixed thereto an agent capable of specifically forming a complex with a domain present on an HCV envelope glycoprotein, thereby removing therefrom HCV or HCV envelope glycoprotein if present in the sample.

As used herein, "treating a bodily fluid sample so as to remove therefrom HCV" means either (a) rendering the HCV in the bodily fluid sample unable to invade target cells, such as those expressing DC-SIGN and/or DC-SIGNR, (b) physically separating HCV from the bodily fluid sample, or (c) a combination of (a) and (b), with the proviso that the HCV present in the resulting sample and capable of invading target cells does not exceed 50% of the amount of such HCV present in the sample prior to removing HCV. As used herein, a target cell includes a cell having DC-SIGN and/or DC-SIGNR present on its surface, wherein the DC-SIGN and/or DC-SIGNR expressing cell is capable of specifically binding to and fusing with HCV contacted therewith.

Suitable conditions for contacting the sample with the subject article of manufacture are conditions which would permit the formation of a complex between the agent and HCV. Such conditions are known to those skilled in the art.

This invention further provides a method of treating a bodily fluid sample so as to substantially reduce the likelihood of a subject's becoming infected with HCV as a result of contact with the sample which comprises contacting the sample with a suitable amount of an aqueous-soluble agent capable of specifically forming a complex with a domain present on an HCV envelope glycoprotein, so as to form a complex between the agent and HCV if present in the sample and thereby reduce the likelihood of a subject's becoming infected with HCV as a result of contact with the sample.

This invention provides a method of substantially reducing the amount of HCV envelope glycoprotein in a bodily fluid sample which comprises contacting the sample with a suitable amount of an aqueous-soluble agent capable of specifically forming a complex with a domain present on an HCV envelope glycoprotein, so as to form a complex between the agent and HCV if present in the sample and thereby reduce the amount of HCV envelope glycoprotein in the sample.

In an embodiment, the blood of HCV-infected individuals will be passed through filters on which DC-SIGN and/or DC-SIGNR-based proteins or antibodies have been immobilized. This would allow the removal of HCV virions and/or HCV envelope glycoprotein from the blood. The presence of HCV envelope glycoprotein in the blood may be pathogenic for example by binding to DC-SIGN and/or DC-SIGNR-expressing cells and inhibiting the immune response or by initiating apoptosis of these cells.

In the preferred embodiment, the subject is a human. As used herein, substantially reducing the likelihood of the subject's becoming infected with HCV means reducing the likelihood of the subject's becoming infected with HCV by at least two-fold. For example, if a subject has a 1% chance of becoming infected with HCV, a two-fold reduction in the likelihood of the subject's becoming infected with HCV would result in the subject's having a 0.5% chance of becoming infected with HCV. In one embodiment, substantially reducing the likelihood of the subject's becoming infected with HCV means reducing the likelihood by at least ten-fold. In the preferred embodiment, substantially reducing the likelihood of a subject's becoming infected with HCV means reducing the likelihood by at least 100-fold.

As used herein, "the subject's becoming infected with HCV" means the invasion of the subject's own cells by HCV.

As used herein, contact with a bodily fluid sample is any contact sufficient to cause HCV in the sample to be transmitted to the subject's body, and thereby infect the subject with HCV.

The amount of aqueous-soluble agent suitable to substantially reduce the likelihood of a subject's becoming infected with HCV may be determined according to methods known to those skilled in the art. In one embodiment, the suitable amount of aqueous-soluble agent is an amount between about 1 pM and about 10 mM. In the preferred embodiment, the suitable amount of aqueous-soluble agent is an amount between about 1 pM and about 10 µM.

In one embodiment, the agent is an antibody. In another embodiment, the agent is a DC-SIGN and/or DC-SIGNR-based molecule.

This invention further provides a method of treating a bodily fluid sample so as to substantially reduce the likelihood of a subject's becoming infected with HIV-1 as a result of contact with the sample which comprises the steps of (a) contacting the sample with a suitable amount of an aqueous-soluble agent capable of specifically forming a complex with a domain present on an HCV envelope glycoprotein, thereby forming a complex between the agent and HCV if present in the sample; and (b) removing any complex so formed from the resulting sample, so as to thereby reduce the likelihood of a subject's becoming infected with HCV as a result of contact with the sample.

Removing complex from the resulting sample may be accomplished according to methods well known to those skilled in the art. Such methods include, for example, affinity chromatography.

The subject method may further comprise the step of removing uncomplexed agent from the sample should such removal be desirable (e.g., when the agent would cause undesirable effects in a subject to whom it is administered).

This invention further provides a method of treating a bodily fluid sample so as to substantially reduce the likelihood of a subject's becoming infected with HCV as a result of contact with the sample which comprises the steps of (a) contacting the sample with a suitable amount of an aqueous-soluble agent which (i) is capable of specifically forming a complex with a domain present on an HCV envelope glycoprotein, and (ii) comprises a moiety capable of specifically forming a complex with a known ligand, which moiety permits the removal of the agent from a sample via contact with an immobilized form of the known ligand, thereby forming a complex between the agent and HCV if present in the sample; and (b) removing any complex so formed from the resulting sample by contacting the resulting sample with an immobilized form of the known ligand, so as to thereby reduce the likelihood of a subject's becoming infected with HCV as a result of contact with the sample.

Methods of immobilizing a ligand are well known to those skilled in the art. As used herein, a ligand in its "immobilized form" is capable of forming a complex with the moiety specifically recognized by the ligand in its free form.

This invention further provides a method of treating a bodily fluid sample so as to substantially reduce the likelihood of a subject's becoming infected with HCV as a result of contact with the sample which comprises the steps of (a) contacting the sample under suitable conditions with an article of manufacture comprising a solid support having operably affixed thereto an agent capable of specifically forming a complex with a domain present on an HCV envelope glycoprotein; and (b) contacting the sample with a suitable amount of an aqueous-soluble agent capable of specifically forming a complex with a domain present on an HCV envelope glycoprotein, so as to form a complex between the agent and HCV if present in the sample, with the proviso that step (a) may either precede or follow step (b).

This invention further provides a method of treating a bodily fluid sample so as to substantially reduce the likelihood of a subject's becoming infected with HCV as a result of contact with the sample which comprises the steps of (a) contacting the sample under suitable conditions with an article of manufacture comprising a solid support having operably affixed thereto an agent capable of specifically forming a complex with a domain present on an HCV envelope glycoprotein; and (b) (i) contacting the sample with a suitable amount of an aqueous-soluble agent capable of specifically forming a complex with a domain present on an HCV envelope glycoprotein, thereby forming a complex between the agent and HIV-1 if present in the sample, and (ii) removing any complex so formed from the resulting sample, with the proviso that step (a) may either precede or follow step (b).

This invention further provides a method of treating a bodily fluid sample so as to substantially reduce the likelihood of a subject's becoming infected with HCV as a result of contact with the sample which comprises the steps of (a) contacting the sample under suitable conditions with an article of manufacture comprising a solid support having operably affixed thereto an agent capable of specifically forming a complex with a domain present on an HCV envelope glycoprotein; and (b) (I) contacting the sample with a suitable amount of an aqueous-soluble agent which (1) is capable of specifically forming a complex with a domain present on an HIV-1 envelope glycoprotein, and (2) comprises a moiety capable of specifically forming a complex with a known ligand, thereby forming a complex between the agent and HCV if present in the sample, and (II) removing any complex so formed from the resulting sample by contacting the resulting sample with an immobilized form of the known ligand, with the proviso that step (a) may either precede or follow step (b).

The methods of the subject invention may further comprise the step of removing target cells from the bodily fluid sample. In the one embodiment, the target cells are leukocytes. Methods of removing leukocytes from a bodily fluid sample are well known to those skilled in the art and include, for example, leukofiltration.

As used herein, a bodily fluid is any fluid which is present in a subject's body and is capable of containing HCV in an HCV-infected subject. Bodily fluids include, but are not limited to, whole blood or derivatives thereof (e.g., red blood cell and platelet preparations), saliva, cerebrospinal fluid, tears, vaginal secretions, urine, alveolar fluid, synovial fluid, semen, pleural fluid and bone marrow. In the preferred embodiment, the bodily fluid is a fluid which is to be administered to a subject. Also in the preferred embodiment, the bodily fluid sample is selected from the group consisting of whole blood, a red blood cell preparation, a platelet preparation and semen.

The bodily fluid samples such as whole blood may further comprise exogenous substances added thereto for clinical or storage purposes. Such exogenous substances include, by way of example, anticoagulants (e.g., citrate) and preservatives (e.g., dextrose).

In one embodiment, the contacting steps of the methods of the subject invention are performed at about 4° C. In another embodiment, the contacting steps of the methods of the subject invention are performed at about 20° C. In still another embodiment, the contacting steps of the methods of the subject invention are performed at about 37° C.

The invention also provides a kit for treating a bodily fluid sample so as to substantially reduce the likelihood of a subject's becoming infected with HCV as a result of contact with the sample which comprises the above-described article of manufacture.

This invention further provides a kit for treating a bodily fluid sample so as to substantially reduce the likelihood of a subject's becoming infected with HCV as a result of contact with the sample which comprises, in separate compartments: (a) an article of manufacture comprising a solid support having operably affixed thereto an agent capable of specifically forming a complex with a domain present on an HCV envelope glycoprotein; and (b) an aqueous-soluble agent capable of specifically forming a complex with a domain present on an HCV envelope glycoprotein.

This invention further provides a kit for treating a bodily fluid sample so as to substantially reduce the likelihood of a subject's becoming infected with HCV as a result of contact with the sample which comprises, in separate compartments: (a) an article of manufacture comprising a solid support having operably affixed thereto an agent capable of specifically forming a complex with a domain present on an HCV envelope glycoprotein; (b) an aqueous soluble agent which (1) is capable of specifically forming a complex with a domain present on an HCV envelope glycoprotein, and (2) comprises a moiety capable of specifically forming a complex with a known ligand, which moiety permits the removal of the agent from a sample via contact with an immobilized form of the known ligand; and (c) an article of manufacture comprising a solid support having operably affixed thereto the known ligand capable of specifically forming a complex with the moiety of the aqueous-soluble agent of step (b).

This invention provides a kit for treating a bodily fluid sample so as to substantially reduce the likelihood of a subject's becoming infected with HCV as a result of contact with the sample which comprises, in separate compartments: (a) an aqueous-soluble agent which (i) is capable of specifically forming a complex with a domain present on an HCV envelope glycoprotein, and (ii) comprises a moiety capable of specifically forming a complex with a known ligand, which moiety permits the removal of the agent from a sample via contact with an immobilized form of the known ligand; and (b) an article of manufacture comprising a solid support having operably affixed thereto the known ligand capable of specifically forming a complex with the moiety of said aqueous-soluble agent.

This invention also provides a kit for reducing the amount of HCV or HCV envelope glycoprotein present in a bodily fluid sample which comprises the above-described article of manufacture. In an embodiment, the bodily fluid is blood.

The kits of the subject invention may further comprise suitable buffers.

In order to facilitate an understanding of the following examples, certain frequently occurring methods and/or terms are best described in Sambrook, et al.

The methods described herein to capture the HCV virions may be used for any purpose known to one skilled in the art. In one embodiment, the method is employed so as to reduce the infectivity of a subject's sample. In one embodiment, the method is employed for concentrating the HCV virions so as to enable a greater chance of HCV detection, such as in a PCR assay for HCV nucleic acid, such as HCV RNA.

Obtaining a sample of HCV envelope glycoprotein$^+$ cells may be performed according to methods well known to those skilled in the art. HCV envelope glycoprotein$^+$ cells may be obtained from blood or any other bodily fluid known to contain HCV envelope glycoprotein$^+$ cells in HCV-infected subjects.

This invention provides a compound or agent capable of inhibiting binding of a DC-SIGN protein to an HCV envelope glycoprotein, thereby inhibiting HCV infection of a cell. This invention provides a compound or agent capable of inhibiting binding of a DC-SIGNR protein to an HCV envelope glycoprotein, thereby inhibiting HCV infection of a cell.

This invention provides an antibody or portion thereof capable of inhibiting binding of a DC-SIGN protein to an HCV envelope glycoprotein, which antibody binds to an epitope located within a region of the DC-SIGN protein, which region of the DC-SIGN protein binds to an HCV envelope glycoprotein. This invention provides an antibody or portion thereof capable of inhibiting binding of a DC-SIGNR protein to an HCV envelope glycoprotein, which antibody binds to an epitope located within a region of the DC-SIGNR protein, which region of the DC-SIGNR protein binds to an HCV envelope glycoprotein.

This invention provides an antibody or portion thereof capable of inhibiting binding of a DC-SIGN protein to an HCV envelope glycoprotein, which antibody binds to an epitope located within a region of the HCV envelope glycoprotein, which region of the HCV envelope glycoprotein binds to a DC-SIGN protein. This invention provides an antibody or portion thereof capable of inhibiting binding of a DC-SIGN protein to an HCV envelope glycoprotein, which antibody binds to an epitope located within a region of the HCV envelope glycoprotein, which region of the HCV envelope glycoprotein binds to a DC-SIGNR protein.

In one embodiment of the antibodies or portions thereof described herein, the antibody is a monoclonal antibody. In one embodiment of the antibodies or portions thereof described herein, the antibody is a polyclonal antibody. In one embodiment of the antibodies or portions thereof described herein, the antibody is a humanized antibody. In one embodiment of the antibodies or portions thereof described herein, the antibody is a chimeric antibody. In one embodiment of the antibodies or portions thereof described herein, the portion of the antibody comprises a light chain of the antibody. In one embodiment of the antibodies or portions thereof described herein, the portion of the antibody comprises a heavy chain of the antibody. In one embodiment of the antibodies or portions thereof described herein, the portion of the antibody comprises a Fab portion of the antibody. In one embodiment of the antibodies or portions thereof described herein, the portion of the antibody comprises a $F(ab')_2$ portion of the antibody. In one embodiment of the antibodies or portions thereof described herein, the portion of the antibody comprises a Fd portion of the antibody. In one embodiment of the antibodies or portions thereof described herein, the portion of the antibody comprises a Fv portion of the antibody. In one embodiment of the antibodies or portions thereof described herein, the portion of the antibody comprises a variable domain of the antibody. In one embodiment of the antibodies or portions thereof described herein, the portion of the antibody comprises one or more CDR domains of the antibody.

In one embodiment of the antibodies or portions thereof described herein, the antibody binds to an epitope located within a region of an E1 HCV envelope glycoprotein. In one embodiment of the antibodies or portions thereof described herein, the antibody binds to an epitope located within a region of an E2 HCV envelope glycoprotein.

The invention embraces antibodies or fragments of antibodies having the ability to block the interaction between HCV and DC-SIGN and/or the interaction between HCV and DC-SIGNR. The antibodies may have specificity to HCV, DC-SIGN or DC-SIGNR. According to a further aspect of the invention, there is provided an antibody with the above specificity for use in the treatment of all HCV infection and in the manufacture of a medicament for the treatment of an HCV infection, The antibody is preferably a monoclonal antibody. Such an antibody can be used to temporarily block the DC-SIGNR receptor preventing infection from HCV, for example, immediately after an accidental infection with HCV-infected blood.

As used herein, "antibody" includes both naturally occurring and non-naturally occurring antibodies. Specifically, "antibody" includes polyclonal and monoclonal antibodies, and monovalent and divalent fragments thereof. Furthermore, "antibody" includes chimeric antibodies, wholly synthetic antibodies, single chain antibodies, and fragments thereof. The antibody may be a human or nonhuman antibody. A nonhuman antibody may be humanized by recombinant methods to reduce its immunogenicity in man. Antibodies are prepared according to conventional methodology. Monoclonal antibodies may be generated using the method of Kohler and Milstein (Nature, 256:495, 1975). To prepare monoclonal antibodies useful in the invention, a mouse or other appropriate host animal is immunized at suitable intervals (e.g., twice-weekly, weekly, twice-monthly or monthly) with antigenic forms of HCV, HCV envelope glycoproteins, DC-SIGN, or DC-SIGNR. The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. A given animal may be immunized with multiple forms of the antigen by multiple routes.

In one embodiment, HCV is purified from the plasma of HCV-infected individuals using the method of sucrose gradient centrifugation. Alternatively, recombinant HCV E1 and/or E2 envelope glycoproteins, which are available commercially from a variety of sources, such as Austral Biologicals (San Ramon, Calif., Cat # HCA-090-2), Immunodiagnostics (Woburn, Mass., Cat #4001) and Accurate Chemical (Westbury, Mass., Cat #YVS8921). The recombinant HCV envelope glycoproteins may be provided by surface expression on recombinant cell lines. DC-SIGN may be provided in the form of human dendritic cells, whereas DC-SIGNR may be provided as liver sinusoidal cells. Recombinant forms of DC-SIGN and DC-SIGNR may be provided using previously described methods {Pohlmann, Soilleux, et al. 2001 ID: 1081}. Alternatively, the antigen may be provided as synthetic peptides corresponding to antigenic regions of interest.

Following the immunization regimen, lymphocytes are isolated from the spleen, lymph node or other organ of the animal and fused with a suitable myeloma cell line using an agent such as polyethylene glycol to form a hydridoma. Following fusion, cells are placed in media permissive for growth of hybridomas but not the fusion partners using standard methods, as described (Goding, Monoclonal Antibodies: Principles and Practice: Production and Application of Monoclonal Antibodies in Cell Biology, Biochemistry and Immunology, 3$^{rd}$ edition, Academic Press, New York, 1996).

Following culture of the hybridomas, cell supernatants are analyzed for the presence of antibodies of the desired specificity, i.e., that selectively bind the antigen. Suitable analytical techniques include ELISA, flow cytometry, immunoprecipitation, and western blotting. Other screening techniques are well-known in the field. Preferred techniques are those that confirm binding of antibodies to conformationally intact, natively folded antigen, such as non-denaturing ELISA, flow cytometry, and immunoprecipitation.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody.

This invention provides in certain embodiments compositions and methods that include humanized forms of antibodies. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference. One of ordinary skill in the art will be familiar with other methods for antibody humanization.

In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA and IgM molecules. A "humanized" antibody retains a similar antigenic specificity as the original antibody. However, using certain methods of humanization, the affinity and/or specificity of binding of the antibody may be increased using methods of "directed evolution", as described by Wu et al.,

*J. Mol. Biol.* 294:151, 1999, the contents of which are incorporated herein by reference.

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

The various antibody molecules and fragments may derive from any of the commonly known immunoglobulin classes, including but not limited to IgA, secretory IgA, IgE, IgG and IgM. IgG subclasses are also well known to those in the art and include but are not limited to human IgG1, IgG2, IgG3 and IgG4.

Monoclonal antibodies may be produced by mammalian cell culture in hydridoma or recombinant cell lines such as Chinese hamster ovary cells or murine myeloma cell lines. Such methods are well-known to those skilled in the art. Bacterial, yeast, and insect cell lines can also be used to produce monoclonal antibodies or fragments thereof. In addition, methods exist to produce monoclonal antibodies in transgenic animals or plants (Pollock et al., J. Immunol. Methods, 231:147, 1999; Russell, Curr. Top. Microbiol. Immunol. 240:119, 1999).

In one embodiment of the agents described herein, the agent is an antibody or portion of an antibody. As used herein, "antibody" means an immunoglobulin molecule comprising two heavy chains and two light chains and which recognizes an antigen. The immunoglobulin molecule may derive from any of the commonly known classes, including but not limited to IgA, secretory IgA, IgG and IgM. IgG subclasses are also well known to those in the art and include but are not limited to human IgG1, IgG2, IgG3 and IgG4. It includes, by way of example, both naturally occurring and non-naturally occurring antibodies. Specifically, "antibody" includes polyclonal and monoclonal antibodies, and monovalent and divalent fragments thereof. Furthermore, "antibody" includes chimeric antibodies, wholly synthetic antibodies, single chain antibodies, and fragments thereof. Optionally, an antibody can be labeled with a detectable marker. Detectable markers include, for example, radioactive or fluorescent markers. The antibody may be a human or nonhuman antibody. The nonhuman antibody may be humanized by recombinant methods to reduce its immunogenicity in man. Methods for humanizing antibodies are known to those skilled in the art. As used herein, "monoclonal antibody," also designated as mAb, is used to describe antibody molecules whose primary sequences are essentially identical and which exhibit the same antigenic specificity. Monoclonal antibodies may be produced by hybridoma, recombinant, transgenic or other techniques known to one skilled in the art. The term "antibody" includes, but is not limited to, both naturally occurring and non-naturally occurring antibodies. Specifically, the term "antibody" includes polyclonal and monoclonal antibodies, and antigen-binding fragments thereof. Furthermore, the term "antibody" includes chimeric antibodies, wholly synthetic antibodies, and antigen-binding fragments thereof. Accordingly, in one embodiment, the antibody is a monoclonal antibody. In one embodiment, the antibody is a polyclonal antibody. In one embodiment, the antibody is a humanized antibody. In one embodiment, the antibody is a chimeric antibody. Such chimeric antibodies may comprise a portion of an antibody from one source and a portion of an antibody from another source.

In one embodiment, the portion of the antibody comprises a light chain of the antibody. As used herein, "light chain" means the smaller polypeptide of an antibody molecule composed of one variable domain (VL) and one constant domain (CL), or fragments thereof. In one embodiment, the portion of the antibody comprises a heavy chain of the antibody. As used herein, "heavy chain" means the larger polypeptide of an antibody molecule composed of one variable domain (VH) and three or four constant domains (CH1, CH2, CH3, and CH4), or fragments thereof. In one embodiment, the portion of the antibody comprises a Fab portion of the antibody. As used herein, "Fab" means a monovalent antigen binding fragment of an immunoglobulin that consists of one light chain and part of a heavy chain. It can be obtained by brief papain digestion or by recombinant methods. In one embodiment, the portion of the antibody comprises a F(ab')$_2$ portion of the antibody. As used herein, "F(ab')2 fragment" means a bivalent antigen binding fragment of an immunoglobulin that consists of both light chains and part of both heavy chains. It cen be obtained by brief pepsin digestion or recombinant methods. In one embodiment, the portion of the antibody comprises a Fd portion of the antibody. In one embodiment, the portion of the antibody comprises a Fv portion of the antibody. In one embodiment, the portion of the antibody comprises a variable domain of the antibody. In one embodiment, the portion of the antibody comprises a constant domain of the antibody. In one embodiment, the portion of the antibody comprises one or more CDR domains of the antibody. As used herein, "CDR" or "complementarity determining region" means a highly variable sequence of amino acids in the variable domain of an antibody.

This invention provides humanized forms of the antibodies described herein. As used herein, "humanized" describes antibodies wherein some, most or all of the amino acids outside the CDR regions are replaced with corresponding amino acids derived from human immunoglobulin molecules. In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA and IgM molecules. A "humanized" antibody would retain a similar antigenic specificity as the original antibody.

One skilled in the art would know how to make the humanized antibodies of the subject invention. Various publications, several of which are hereby incorporated by reference into this application, also describe how to make humanized antibodies. For example, the methods described in U.S. Pat. No. 4,816,567 comprise the production of chimeric antibodies having a variable region of one antibody and a constant region of another antibody.

U.S. Pat. No. 5,225,539 describes another approach for the production of a humanized antibody. This patent describes the use of recombinant DNA technology to produce a humanized antibody wherein the CDRs of a variable region of one immunoglobulin are replaced with the CDRs from an immunoglobulin with a different specificity such that the humanized antibody would recognize the desired target but would not be recognized in a significant way by the human subject's immune system. Specifically, site directed mutagenesis is used to graft the CDRs onto the framework.

Other approaches for humanizing an antibody are described in U.S. Pat. Nos. 5,585,089 and 5,693,761 and WO 90/07861 which describe methods for producing humanized immunoglobulins. These have one or more CDRs and possible additional amino acids from a donor immunoglobulin and a framework region from an accepting human immunoglobulin. These patents describe a method to increase the affinity of an antibody for the desired antigen. Some amino acids in the framework are chosen to be the same as the amino acids at those positions in the donor rather than in the acceptor. Specifically, these patents describe the preparation of a humanized antibody that binds to a receptor by combining the CDRs of a mouse monoclonal antibody with human immunoglobulin framework and constant regions. Human framework regions can be chosen to maximize homology with the mouse sequence. A computer model can be used to identify amino acids in the framework region which are likely to interact with the CDRs or the specific antigen and then mouse amino acids can be used at these positions to create the humanized antibody.

The above U.S. Pat. Nos. 5,585,089 and 5,693,761, and WO 90/07861 also propose four possible criteria which may used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3 Å of the CDRs in a three dimensional model of the antibody and is predicted to be capable of interacting with the CDRs. The above methods are merely illustrative of some of the methods that one skilled in the art could employ to make humanized antibodies.

This invention provides isolated nucleic acids encoding the agents and/or compounds described herein. In one embodiment, the nucleic acid encodes the antibodies described herein or their humanized versions. The nucleic acid can be RNA, DNA or cDNA. In one embodiment, the nucleic acid encodes the light chain. In one embodiment, the nucleic acid encodes the heavy chain. In one embodiment, the nucleic acid encodes both the heavy and light chains. In one embodiment, one or more nucleic acids encode the Fab portion. In one embodiment, one or more nucleic acids encode CDR portions. In one embodiment, the nucleic acid encodes the variable domain.

This invention provides the nucleic acids described herein, wherein the nucleic acids may be altered by the insertion, deletion and/or substitution of one or more nucleotides, which could result in an alteration of the nucleic acid sequence. In one embodiment, the nucleotide changes do not result in a mutation at the amino acid level. One embodiment, the nucleotide change may result in an amino acid change. Such amino acid change could be one which does not affect the protein's function.

This invention provides a vector which comprises a nucleic acid described herein. On embodiment, the vector is a plasmid. This invention provides a host vector system which comprises the vector described herein and suitable host cell. This invention provides a method of producing a polypeptide which comprises growing the host vector system described herein under suitable conditions for producing the polypeptide and recovering the polypeptide so produced.

In one embodiment of the agents described herein, the agent is a polypeptide. In one embodiment of the agents described herein, the agent is a oligopeptide. As used herein, "polypeptide" means two or more amino acids linked by a peptide bond.

This invention provides a polypeptide capable of inhibiting binding of a DC-SIGN protein to an HCV envelope glycoprotein, which polypeptide comprises consecutive amino acids having a sequence which corresponds to the sequence of at least a portion of an extracellular domain of a DC-SIGN protein, which portion binds to an HCV envelope glycoprotein.

In one embodiment, the polypeptide corresponds to an extracellular domain of DC-SIGN. In one embodiment of the polypeptide, the extracellular domain comprises consecutive amino acids having a sequence which begins with the lysine at position 62 and ends with the carboxy terminal amino acid as set forth in SEQ ID NO: 1.

In one embodiment of the polypeptide, the extracellular domain is a C-type lectin binding domain or portion thereof.

In one embodiment of the polypeptide, the C-type lectin domain comprises consecutive amino acids having a sequence which begins with the leucine at position 229 and ends with the carboxy terminal amino acid as set forth in SEQ ID NO 1.

This invention provides a polypeptide capable of inhibiting binding of a DC-SIGNR protein to an HCV envelope glycoprotein, which polypeptide comprises consecutive amino acids having a sequence which corresponds to the sequence of at least a portion of an extracellular domain of a DC-SIGNR protein, which portion binds to an HCV envelope glycoprotein. In one embodiment of the polypeptide, the extracellular domain comprises consecutive amino acids having a sequence which begins with the lysine at position 74 and ends with the carboxy terminal amino acid as set forth in SEQ ID NO: 2.

In one embodiment of the polypeptide, the C-type lectin domain comprises consecutive amino acids having a sequence which begins with the leucine at position 241 and ends with the carboxy terminal amino acid as set forth in SEQ ID NO 2.

This invention provides a polypeptide capable of inhibiting binding of a DC-SIGN protein to an HCV envelope glycoprotein, which polypeptide comprises consecutive amino acids having a sequence which corresponds to the sequence of at least a portion of an extracellular domain of an HCV envelope glycoprotein, which portion binds to a DC-SIGN protein.

In one embodiment, the polypeptide comprises consecutive amino acids having a sequence which corresponds to the sequence of at least a portion of an extracellular domain of an E1 HCV envelope glycoprotein, which portion binds to a DC-SIGN protein. In one embodiment, the polypeptide comprises consecutive amino acids having the sequence as set forth in SEQ ID NO: 3 from position 192 to position 346, or a portion thereof.

In one embodiment, the polypeptide comprises consecutive amino acids having a sequence which corresponds to the sequence of at least a portion of an extracellular domain of an E2 HCV envelope glycoprotein, which portion binds to a DC-SIGN protein. In one embodiment, the polypeptide comprises consecutive amino acids having the sequence as set forth in SEQ ID NO: 3 from position 383 to position 717, or a portion thereof.

This invention provides a polypeptide capable of inhibiting binding of a DC-SIGNR protein to an HCV envelope glycoprotein, which polypeptide comprises consecutive amino acids having a sequence which corresponds to the sequence of at least a portion of an extracellular domain of an HCV envelope glycoprotein, which portion binds to a DC-SIGNR protein.

In one embodiment, the polypeptide comprises consecutive amino acids having a sequence which corresponds to the sequence of at least a portion of an extracellular domain of an E1 HCV envelope glycoprotein, which portion binds to a DC-SIGNR protein. In one embodiment, the polypeptide comprises consecutive amino acids having the sequence as set forth in SEQ ID NO: 3 from position 192 to position 346, or a portion thereof.

In one embodiment, the polypeptide comprises consecutive amino acids having a sequence which corresponds to the sequence of at least a portion of an extracellular domain of an E2 HCV envelope glycoprotein, which portion binds to a DC-SIGNR protein. In one embodiment, the polypeptide comprises consecutive amino acids having the sequence as set forth in SEQ ID NO: 3 from position 383 to position 717, or a portion thereof.

The compounds and/or agents described herein may be made by any means known to one skilled in the art. For example, a protein may be made by recombinant expression from a nucleic acid, such as a plasmid or vector comprising the encoding nucleic acid, wherein the plasmid or vector is in a suitable host cell, i.e. a host-vector system for the production of the polypeptide of interest. A suitable vector may be made which comprises suitable regulatory sequences, such as enhancers and promotors. The host cell may be of any type, including but not limited to mammalian, bacteria and yeast cells. Suitable bacterial cells include E.coli cells. Suitable mammalian cells include but are not limited to human embryonic kidney (HEK) 293T cells, HeLa cells, NIH 3T3 cells Chinese hamster ovary (CHO) cells and Cos cells.

If the protein is produced recombinantly, it may be expressed from a plasmid containing a synthetic nucleic acid insert. Such insertion site in the plasmid may allow linking the protein to a tag, such as a poly-Histidine tag. Such a tag facilitates later protein purification.

A Nucleic acid encoding the polypeptide, protein or functional equivalent thereof may be cloned under the control of an inducible promoter, thereby allowing regulation of protein expression. Suitable inducible systems are known to those of skill in the art.

Vectors for expressing the protein or functional equivalents described herein may be selected from commercial sources or constructed for a particular expression system. Such vectors may contain appropriate regulatory sequences, such as promoter sequences, terminator sequences, polyadenylation sequences, enhancer sequences and marker genes. Vectors may be plasmids, or viral-based. One skilled may consult Molecular Cloning: a laboratory manual (Sambrook et al., 1989). Many known techniques and protocols for the manipulation of nucleic acids and analysis of proteins are described in detail in "Short protocols in molecular biology", second addition, Ausubel et al. (John Wiley & Sons 1992).

Methods for the isolation and purification of recombinant proteins are known to those of skill in the art and described in various sources such as in Sambrook et al. (1989). In bacteria such as E.Coli, the recombinant protein may form inclusion bodies within the bacterial cell, thus facilitating its preparation. If produced in inclusion bodies, the carrier protein may require refolding to a natural conformation.

Additionally, in order to tailor the properties of the protein or functional equivalent thereof, one skilled appreciates that alterations may be made at the nucleic acid level from known protein sequences, such as by adding, substituting, deleting or inserting one or more nucleotides. Site-directed mutagenesis is the method of preference that may be employed to make mutated proteins. There are many site-directed mutagenesis techniques known to those skill in the art, including but not limited to oligonucleotide-directed mutagenesis using PCR, such as is described in Sambrook, or using commercially available kits.

Suitable vectors may be selected or constructed, containing appropriate regulatory sequences, including promoter sequences, polyadenylation sequences, enhancer sequences, marker genes and other sequences as appropriate. The vectors include but are not limited to plasmids, such as viral e.g. phage, or phagemid, and as described in Sambrook. Techniques and protocols for manipulating nucleic acids, such as in preparing nucleic acid constructs, mutagenesis, sequencing, introducing nucleic acids into cells and gene expression, and analysis of proteins, are described in detail in *Short Protocals in Molecular Biology*, Second Edition, Ausubel et al. Eds, John Wiley & Sons, 1992, which is incorporated by reference.

This invention also provides soluble forms of the polypeptides described herein. Accordingly, for example, a transmembrane domain for a polypeptide expressed on a cell surface may be removed such that the polypeptide would become soluble.

This invention provides a nonpeptidyl agent capable of inhibiting binding of a DC-SIGN protein to an HCV envelope glycoprotein, which nonpeptidyl binds to an epitope located within a region of the DC-SIGN protein, which region of the DC-SIGN protein binds to an HCV envelope glycoprotein. This invention provides a nonpeptidyl agent capable of inhibiting binding of a DC-SIGNR protein to an HCV envelope glycoprotein, which nonpeptidyl binds to an epitope located within a region of the DC-SIGNR protein, which region of the DC-SIGNR protein binds to an HCV envelope glycoprotein.

This invention provides a nonpeptidyl agent capable of inhibiting binding of a DC-SIGN protein to an HCV envelope glycoprotein, which nonpeptidyl agent binds to at least a portion of an extracellular domain of an HCV envelope glycoprotein, which portion binds to a DC-SIGN protein. This invention provides a nonpeptidyl agent capable of inhibiting binding of a DC-SIGNR protein to an HCV envelope glycoprotein, which nonpeptidyl agent binds to at least a portion of an extracellular domain of an HCV envelope glycoprotein, which portion binds to a DC-SIGNR protein.

In one embodiment of the nonpeptidyl agents described herein, the nonpeptidyl agent binds to at least a portion of an extracellular domain of an E1 HCV envelope glycoprotein. In one embodiment of the nonpeptidyl agents described herein, the nonpeptidyl agent binds to at least a portion of an extracellular domain of an E2 HCV envelope glycoprotein.

In one embodiment of the nonpeptidyl agents described herein, the nonpeptidyl agent is a carbohydrate. The carbohydrate may one known to those of skill in the art, including but not limited to mannose, mannan and methyl-α-D-mannopyranoside.

As used herein, "nonpeptidyl agent" means an agent that does not consist in its entirety of a linear sequence of amino acids linked by peptide bonds. A nonpeptidyl molecule may, however, contain one or more peptide bonds. In one embodiment, the nonpeptidyl agent is a compound having a molecular weight less than 500 daltons. As used herein, a "small molecule" or small molecular weight molecule is one having a molecular weight less than 500 daltons.

This invention provides a composition which comprises a carrier and a compound which inhibits binding of HCV to DC-SIGN and/or DC-SIGNR on the surface of a cell. In one embodiment, the composition comprises an amount of the compound effective to inhibit binding of HCV to DC-SIGN and/or DC-SIGNR on the surface of a cell.

This invention provides a composition which comprises an antibody or portion thereof described herein and a carrier. This invention provides a composition which comprises a polypeptide described herein and a carrier. This invention provides a composition which comprises a nonpeptidyl agent described herein and a carrier. The carriers include but are not limited to an aerosol, intravenous, oral and topical carriers. Accordingly, the invention provides the above composition adapted for aerosol, intravenous, oral or topical applications or other applications known to one skilled in the art.

This invention provides the agents, compounds and/or compositions described herein and carrier. Such carrier may be a pharmaceutically acceptable carrier.

Pharmaceutically acceptable carriers are well known to those skilled in the art. Such pharmaceutically acceptable carriers may include but are not limited to aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

As used herein, "composition" means a mixture. The compositions include but are not limited to those suitable for oral, rectal, intravaginal, topical, nasal, opthalmic, or parenteral administration to a subject. As used herein, "parenteral" includes but is not limited to subcutaneous, intravenous, intramuscular, or intrasternal injections or infusion techniques. As used herein, "administering" may be effected or performed using any of the methods known to one skilled in the art. The methods for administration to the subject include but are not limited to oral, rectal, intravaginal, topical, nasal, opthalmic, parenteral subcutaneous, intravenous, intramuscular, or intrasternal injections or infusion techniques.

This invention provides DC-SIGN and DC-SIGNR proteins, or functional equivalents thereof, for use in the therapy or diagnosis of HCV. The invention provides a compound that binds specifically to DC-SIGN and/or DC-SIGNR proteins for use in the therapy or diagnosis of HCV.

As used herein, a functional equivalent of DC-SIGN or DC-SIGNR is a compound which is capable of binding to HCV, thereby preventing its interaction with DC-SIGN and/or DC-SIGNR. Preferably, the functional equivalent is a peptide or protein. The term "functional equivalent" includes fragments, mutants, and muteins of DC-SIGN and DC-SIGNR. Functional equivalents include molecules that bind HCV, preferably the HCV envelope glycoproteins, and comprise all or a portion of the extracellular domains of DC-SIGN or DC-SIGNR.

The functional equivalents include soluble forms of the DC-SIGN or DC-SIGNR proteins. A suitable soluble form of these proteins, or functional equivalents thereof, might comprise, for example, a truncated form of the protein from which the transmembrane domain has been removed by chemical, proteolytic or recombinant methods. The transmembrane domain of DC-SIGN starts at about glycine 49 and ends at about serine 61, whereas the transmembrane domain of DC-SIGNR starts at about glycine 49 and ends at about serine 73.

In one embodiment, the functional equivalent comprises all or a portion of the extracellular domain of DC-SIGN or DC-SIGNR. The extracellular region of DC-SIGN begins at about lysine 62 and includes the carboxy-terminal amino acids, whereas the extracellular region of DC-SIGNR begins at about lysine 74 and includes the carboxy-terminal amino acids. Preferably, the functional equivalent is at least 80% homologous to the corresponding protein. In a preferred embodiment, the functional equivalent is at least 90% homologous as assessed by any conventional analysis algorithm such as for example, the Pileup sequence analysis software (Program Manual for the Wisconsin Package, 1996). Amino acid numbering is as provided in GenBank Protein Accession Number AAK20997 for DC-SIGN and AAG13848 for DC-SIGNR.

The term "a functionally equivalent fragment" as used herein also may mean any fragment or assembly of fragments of DC-SIGN and/or DC-SIGNR that binds to HCV, preferably that binds to the HCV envelope glycoproteins. The C-type lectin binding domain of DC-SIGN begins at about leucine 229 and includes the carboxy-terminal amino acids, whereas the C-type lectin binding domain of DC-SIGNR begins at about leucine 241 and includes the carboxy-terminal amino acids. The complete protein, extracellular domain, or C-type lectin domain may be truncated at one or both ends or portions may be removed internally provided that the protein retains the defined function.

Proteinaceous, functionally equivalent fragments or analogues may belong to the same protein family as the human DC-SIGN and DC-SIGNR proteins identified herein. By "protein family" is meant a group of proteins that share a common function and exhibit common sequence homology. Homologous proteins may be derived from non-human species. Preferably, the homology between functionally equivalent protein sequences is at least 25% across the whole of amino acid sequence of the complete protein or of the complete EC2 fragment (amino acids 11.3–201). More preferably, the homology is at least 50%, even more preferably 75% across the whole of amino acid sequence of the protein or protein fragment. More preferably, homology is greater than 80% across the whole of the sequence. More preferably, homology is greater than 90% across the whole of the sequence. More preferably, homology is greater than 95% across the whole of the sequence.

The term "a functionally equivalent analogue" is used to describe those compounds that possess an analogous function to an activity of the DC-SIGN and DC-SIGNR proteins and may, for example comprise a peptide, cyclic peptide, polypeptide, antibody or antibody fragment. These compounds may be proteins, or may be synthetic agents designed so as to mimic certain structures or epitopes on the inhibitor protein. Preferably, the compound is an antibody or antibody fragment.

The term "functionally equivalent analogue" also includes any analogue of DC-SIGN or DC-SIGNR obtained by altering the amino acid sequence, for example by one or more amino acid deletions, substitutions or additions such that the protein analogue retains the ability to bind to HCV, preferably the envelope glycoproteins of HCV. Amino acid substitutions may be made, for example, by point mutation of the DNA encoding the amino acid sequence. In one embodiment, the analogue retains the ability to bind HCV but does not bind ICAM-3.

The functional equivalent of DC-SIGN or DC-SIGNR may be an analogue of a fragment of the DC-SIGN or DC-SIGNR. The DC-SIGN or DC-SIGNR or functional equivalent may be chemically modified, provided it retains its ability to bind to HCV, preferably the envelope glycoproteins of HCV.

This invention also provides functional equivalents of such polypeptides and fragments thereof. Such functional equivalents may be at least 75% homologous to the native sequence. Such functional equivalents may also be at least 80%, at least 85%, at least 90%, at least 95% or at least 100% homologous to the native sequence. A functionally equivalent fragment may be a fragment of the polypeptide that still binds to its target ligand. For example, a functionally equivalent fragment of the E1 ectodomain would be a fragment that has a deletion of at least one amino acid at it's amino terminal end, at it's carboxy terminal end, internally, or a combination thereof, yet still binds to its ligand on the cell susceptible to HCV infection.

This invention also provides functionally equivalent analogs of such polypeptides and polypeptide fragments. Such analogs would have an activity which is analogous to the polypeptide or fragment. Such analogs may be obtained by changing the amino acid sequence, such as by an insertion, deletion or substitution of at least one amino acid. Such an analog would still bind to its ligand. For example, an E1 analog would still bind to its ligand on the cell susceptible to HCV infection. Amino acid substitutions may be conservative substitutions. Such conservative substitutions may ones within the following groups: (1) glycine and alanine; (2) valine, isoleucine, and leucine; (3) aspartic acid and glutamic acid; (4) asparagine and glutamine; (5)serine and threonine; (6) lysine and arginine; (7) phenylalanine and tyrosine. Such substitutions may also be homologous substitutions such as within the following groups: (a) glycine, alanine, valine, leucine, and isoleucine; (b) phenylalanine, tyrosine, and tryptophan; (c) lysine, arginine, and histidine; (d) aspartic Acid, and glutamic Acid; (e) asparagine and glutamine; (f) serine and threonine; (g) cysteine and methionine.

The functional equivalent may also be modified such as by a chemical modification, yet wherein it still binds to its respective ligand.

It is envisaged that such molecules will be useful in preventative therapy of HCV infection, because these molecules will bind specifically to the virus and will thus prevent entry of the virus into cells. As used herein, "binding specifically" means that the functionally equivalent analogue has high affinity for HCV or the HCV envelope glycoproteins but not for control proteins. Specific binding may be measured by a number of techniques such as ELISA, flow cytometry, western blotting, or immunoprecipitation. Preferably, the functionally equivalent analogue specifically binds to HCV or the HCV envelope glycoproteins at nanomolar or picomolar concentrations.

This application also provides a compound that binds to DC-SIGN and/or DC-SIGNR for use in the diagnosis or therapy of HCV. Preferably the compound binds specifically to DC-SIGN and/or DC-SIGNR at nanomolar or picomolar concentrations. Such compounds may be used to prevent the virus binding and infecting target cells. The compound includes but is not limited to an antibody, a carbohydrate, a small molecule, a peptide, a polypeptide, and an oligopeptide.

The DC-SIGN protein, DC-SIGNR protein, or functional equivalent thereof may be produced by any suitable means, as will be apparent to those of skill in the art. In order to produce sufficient amounts of the DC-SIGN protein, DC-SIGNR protein, or functional equivalents thereof for use in accordance with the present invention, expression may conveniently be achieved by culturing under appropriate conditions recombinant host cells containing the DC-SIGNR protein, or functional equivalent thereof. Preferably, the DC-SIGN or DC-SIGNR protein is produced by recombinant means, by expression from an encoding nucleic acid molecule. Systems for cloning and expression of a polypeptide in a variety of different host cells are well known.

When expressed in recombinant form, the DC-SIGN protein, DC-SIGNR protein or functional equivalent thereof is preferably generated by expression from an encoding nucleic acid in a host cell. Any host cell may be used, depending upon the individual requirements of a particular system. Suitable host cells include bacteria mammalian cells, plant cells, yeast and baculovirus systems. Mammalian cell lines available in the art for expression of a heterologous polypeptide include Chinese hamster ovary cells. HeLa cells, baby hamster kidney cells and many others. Bacteria are also preferred hosts for the production of recombinant protein, due to the ease with which bacteria may be manipulated and grown. A common, preferred bacterial host is *E coli*.

The nucleic acids, polyepeptides and antibodies or any other agent or compound described herein may be isolated and/or purified. One skilled in the art would know how to isolate and/or purify them. Methods are provided in any laboratory manual such as "Molecular Cloning" by Samrook, Fritsch and Maniatis.

As used herein, the following standard abbreviations are used throughout the specification to indicate specific amino acids: A=ala=alanine; R=arg=arginine; N=asn=asparagine D=asp=aspartic acid; C=cys=cysteine; Q=gln=glutamine; E=glu=glutamic acid; G=gly=glycine; H=his=histidine; I=ile=isoleucine; L=leu=leucine; K=lys=lysine; M=met=methionine; F=phe=phenylalanine; P=pro=proline; S=ser=serine; T=thr=threonine; W=trp=tryptophan; Y=tyr=tyrosine; and V=val=valine.

This invention provides a transgenic nonhuman animal which comprises a transgene encoding the polypeptide of interest or a functional equivalent thereof. The following U.S. patents are hereby incorporated by reference: U.S. Pat. No. 6,025,539, IL-5 transgenic mouse; U.S. Pat. No. 6,023,010, Transgenic non-human animals depleted in a mature lymphocytic cell-type; U.S. Pat. No. 6,018,098, In vivo and in vitro model of cutaneous photoaging; U.S. Pat. No. 6,018,097, Transgenic mice expressing human insulin; U.S. Pat. No. 6,008,434, Growth differentiation factor-11 transgenic mice; U.S. Pat. No. 6,002,066; H2-M modified transgenic mice; U.S. Pat. No. 5,994,618, Growth differentiation factor-8 transgenic mice; U.S. Pat. No. 5,986,171, Method for examining neurovirulence of polio virus, U.S. Pat. No. 5,981,830, Knockout mice and their progeny with a disrupted hepsin gene; U.S. Pat. No. 5,981,829, .DELTA.Nur77 transgenic mouse; U.S. Pat. No. 5,936,138; Gene encoding mutant L3T4 protein which facilitates HIV infection and transgenic mouse expressing such protein; U.S. Pat. No. 5,912,411, Mice transgenic for a tetracycline-inducible transcriptional activator; U.S. Pat. No. 5,894,078, Transgenic mouse expressing C-100 app.

The methods used for generating transgenic mice are well known to one of skill in the art. For example, one may use the manual entitled "Manipulating the Mouse Embryo" by Brigid Hogan et al. (Ed. Cold Spring Harbor Laboratory) 1986. See for example, Leder and Stewart, U.S. Pat. No. 4,736,866 for methods for the production of a transgenic mouse.

For sometime it has been known that it is possible to carry out the genetic transformation of a zygote (and the embryo and mature organism which result therefrom) by the placing or insertion of exogenous genetic material into the nucleus of the zygote or to any nucleic genetic material which ultimately forms a part of the nucleus of the zygote. The genotype of the zygote and the organism which results from a zygote will include the genotype of the exogenous genetic material. Additionally, the inclusion of exogenous genetic material in the zygote will result in a phenotype expression of the exogenous genetic material.

The genotype of the exogenous genetic material is expressed upon the cellular division of the zygote. However, the phenotype expression, e.g., the production of a protein product or products of the exogenous genetic material, or alterations of the zygote's or organism's natural phenotype, will occur at that point of the zygote's or organism's development during which the particular exogenous genetic material is active. Alterations of the expression of the phenotype include an enhancement or diminution in the expression of a phenotype or an alteration in the promotion and/or control of a phenotype, including the addition of a new promoter and/or controller or supplementation of an existing promoter and/or controller of the phenotype.

The genetic transformation of various types of organisms is disclosed and described in detail in U.S. Pat. No. 4,873,191, issued Oct. 10, 1989, which is incorporated herein by reference to disclose methods of producing transgenic organisms. The genetic transformation of organisms can be used as an in vivo analysis of gene expression during differentiation and in the elimination or diminution of genetic diseases by either gene therapy or by using a transgenic non-human mammal as a model system of a human disease. This model system can be used to test putative drugs for their potential therapeutic value in humans.

The exogenous genetic material can be placed in the nucleus of a mature egg. It is preferred that the egg be in a fertilized or activated (by parthenogenesis) state. After the addition of the exogenous genetic material, a complementary haploid set of chromosomes (e.g., a sperm cell or polar body) is added to enable the formation of a zygote. The zygote is allowed to develop into an organism such as by implanting it in a pseudopregnant female. The resulting organism is analyzed for the integration of the exogenous genetic material. If positive integration is determined, the organism can be used for the in vivo analysis of the gene expression, which expression is believed to be related to a particular genetic disease.

The "transgenic non-human animals" of the invention are produced by introducing "transgenes" into the germline of the non-human animal. Embryonal target cells at various developmental stages can be used to introduce transgenes. Different methods are used depending on the stage of development of the embryonal target cell. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster, et al. (1985) Proc. Natl. Acad. Sci. U.S.A. 82, 4438–4442). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) Proc. Natl. Acad. Sci U.S.A. 73, 1260–1264). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retrovirus carrying the transgene (Jahner, et al. (1985) Proc. Natl. Acad. Sci. U.S.A. 82, 6927–6931; Van der Putten, et al. (1985) Proc. Natl. Acad. Sci U.S.A. 82, 6148–6152). Transfection is easily and efficiently obtained by culturing the blastomeres on a monolayer of virus-producing cells (Van der Putten, supra; Stewart, et al. (1987) EMBO J. 6, 383–388). Alternatively, infection can be performed at a later stage. Virus or virus-producing cells can be injected into the blastocoele (Jahner, D., et al. (1982) Nature 298, 623–628).

Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line, albeit with low efficiency, by intrauterine retroviral infection of the midgestation embryo (Jahner, D. et al. (1982) supra).

A third type of target cell for transgene introduction is the embryonal stem cell (ES). ES cells are obtained from pre-implantation embryos cultured in vitro and fused with embryos (Evans, M. J., et al. (1981) Nature 292, 154–156; Bradley, M. O., et al. (1984) Nature 309, 255–258; Gossler, et al. (1986) Proc. Natl. Acad. Sci U.S.A. 83, 9065–9069; and Robertson, et al. (1986) Nature 322, 445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) Science 240, 1468–1474.

As used herein, a "transgene" is a DNA sequence introduced into the germline of a non-human animal by way of human intervention such as by way of the above described methods.

The invention is illustrated in the Experimental Detail section which follows. These experimental details are set forth to aid in an understanding of the invention, but they are not intended to, and should not be construed to, limit in any way the invention as set forth in the claims which follow thereafter.

EXPERIMENTAL DETAILS

First Set of Experiments

Binding of Hepatitis C Virus Structural Glycoprotein E2 to Human C-Type Lectins, DC-SIGN and DC-SIGN-R Summary DC-SIGN, a human C-type lectin, is expressed on the surface of dendritic cells (DC), and a highly-homologous protein, DC-SIGN-R, is found at high levels on sinusoidal endothelial cells of the liver and lymph node. These molecules bind HIV envelope glycoprotein, gp120, and facilitate virus transmission in trans by attachment to DC. HCV E2 is the functional equivalent of HIV gp120 and contains abundant high-mannose type oligosaccharides which may bind to lectin molecules, DC-SIGN and DC-SIGN-R. To test this hypothesis, HeLa cell lines expressing DC-SIGN or DC-SIGN-R were constructed and binding to E2 protein and HCV virions was evaluated. Using a fluorometric bead assay, it was demonstrated for the first time that purified E2 binds to DC-SIGN and DC-SIGN-R and these interactions are inhibited by a monoclonal antibody to DC-SIGN/DC-SIGN-R in addition to mannan and calcium chelators. From these experiments it appears that DC-SIGN and DC-SIGN-R function as attachment co-receptors for HCV and that their expression on DC, and on endothelium in the liver and placenta have important implications for HCV disease.

Materials and Methods

Plasmids and Cells

Plasmids pcDNA3-DC-SIGN and pcDNA3-DC-SIGN-R (Item # 5444 and 6749 respectively, AIDS Research and Reference Reagent Program, Rockville, Md.) were transfected into HeLa cells using a lipid formulation (Effectene, Qiagen, Valencia, Calif.) according to the manufacturer's suggested protocol. Two days post-transfection, cells were treated with standard growth media (Dulbecco's modified Eagle's medium (DMEM) containing 10% fetal bovine serum (FBS; Hyclone, Logan, Utah), penicillin/streptomycin (Life Technologies, Carlsbad, Calif.), and L-glutamine (Life Technologies) supplemented with 600 ug/ml Geneticin (Life Technologies). After 2 weeks, surviving colonies of cells were selected, expanded, and screened by flow cytometry using monoclonal antibodies that recognize DC-SIGN (507D, L-SIGN (612X), or both DC- and L-SIGN (604L). The transfected HeLa cell lines were routinely cultured in DMEM supplemented with 10% FBS, penicillin/streptomycin, L-Glutamine with Geneticin (600 ug/ml). Growing cells were divided for maintenance culture using cell dissociation solution (Sigma, St. Louis, Mo.).

Antibodies

The following mAbs were used

Anti-E2 mAb HCM-091-a-5 (Clone 4F6/2) from Austral Biologicals (San Ramon, Calif.), is a mouse IgG1 mAb which reacts with linear epitope in E2 and with serum from HCV seropositive donors. H31, H33, H44, H48, H53, H55, H60, H61 are all anti HCV-E2 mouse mAbs (from Dr. Jean Dubuisson, Institut Pasteur de Lille, France) that cross-react with conformation epitopes (Deleersnyder et al, J. Virol, 71, 697–704 (1997), Flint et al, J. Virol, 73, 6782–6790 (1999)).

120507 (507D) from BD Pharmingen (San Diego, Calif.) is a DC-SIGN-specific, lectin binding domain targeted, conformation dependent, mouse IgG2b. 507D blocks SIV and HIV infection and ICAM-3 adhesion (Jameson et al, J. Virol, 76, 1866–1875 (2002), Wu et al, J. Virol, 76, 5905–5914 (2002)).

120604 (604L) from BD Pharmingen (San Diego, Calif.) is a DC-SIGN-R-specific, lectin binding domain targeted, conformation dependent, mouse IgG2b. 604L does not block binding to SIV or HIV, and exhibits only weak or no blocking of ICAM-3 adhesion (Jameson et al, J. Virol, 76, 1866–1875 (2002), Wu et al, J. Virol, 76, 5905–5914 (2002)).

120612 (612X) from BD Pharmingen (San Diego, Calif.) is a mouse IgG2a that recognizes the lectin binding domain of both DC-SIGN and DC-SIGN-R). 612X blocks ICAM-3 adhesion and HIV infection (Jameson et al, J. Virol, 76, 1866–1875 (2002), Wu et al, J. Virol, 76, 5905–5914 (2002)).

DC4 (item # 5442, AIDS Research and Reference Reagent Program, Rockville, Md.) is a mouse IgG1 that recognizes both DC-SIGN and DC-SIGN-R, via the neck or repeat region, and not the lectin-binding domain. DC4 does not block ICAM-3 binding or SIV transmission (Baribaud et al, J. Virol, 10281–10289 (2001)).

DC28 (item # 5443, AIDS Research and Reference Reagent Program, Rockville, Md.) is a mouse IgG2a that recognizes both DC-SIGN and DC-SIGN-R, via the neck or repeat region, and not the lectin-binding domain. DC28 does not block ICAM-3 binding or SIV transmission (Baribaud et al, J. Virol, 10281–10289 (2001)).

Immunofluorescence

Cells were stained in PBS/0.5% BSA at 4° C. for 30 minutes with primary mAbs and washed before addition of isotype-specific FITC-conjugated secondary mAbs (anti-mouse-FTTC, BD Pharmingen (San Diego, Calif.) for a further 30 minutes at 4° C. After washing, cells were analyzed by flow cytometry using a FACScan (Becton Dickinson, Mountain View, Calif.). Isotype-specific controls were included to establish quadrant positions.

Preparation of HCV-E2 Fluorescent Beads

Carboxylate-modified FluoSpheres® NeutrAvidin™ labeled microspheres (505/515 nm, 1.0 um; Molecular Probes, Eugene, Oreg.) were coated with HCV E2 glycoprotein as described for ICAM-1 beads (Geijtenbeek et al, Blood, 94, 754–764 (1999)). Briefly, NeutrAvidin™-coated beads were sonicated, and washed in PBS/BSA (0.5%). Beads were incubated with biotinylated-Sp-conjugated AffiniPure F(ab')2 goat anti-mouse IgG F(ab')2 fragment specific (6 ug/ml in PBS/BSA (0.5%); Jackson Immunoresearch Laboratories, Inc., West Grove, Pa.) for 2 hours at 37° C. After washing, beads were incubated with mouse anti-E2 antibodies (6 ug/ml in PBS/BSA (0.5%)) at 4° C. overnight. The beads were washed and incubated with 250 ng/ml purified HCV E2 produced in CHO cells (Accurate Chemicals, NY) overnight at 4° C. Identity of E2 protein was confirmed by Western blot analysis with anti-E2 mAbs (data not shown).

Fluorescent Bead Adhesion Assay

This was performed as described by Geijtenbeek et al, (Blood, 94, 754–764 (1999)), with modifications. Cells were removed from culture by cell dissociation solution (Sigma) for 5 minutes at 37° C. and washed three times in adhesion buffer (20 mM Tris-HCl [pH 8.0], 150 mM NaCl, 1 mM CaCl2, 2 mM MgCl2, and 0.5% BSA). Cells were resuspended at a final concentration of 5×106 cells/ml in adhesion buffer for 30 minutes at 4° C. to recharge Ca2+ levels. Cells (5×105) were preincubated with mannan (20 ug/ml; Sigma), antibodies (0.1–10 ug/ml), EDTA (5 mM) or EGTA (5 mM) for 10 minutes at room temperature. HCV-E2-coated fluorescent beads (20 beads/cell) were added, and the suspension incubated for 30 minutes at 37° C. Adhesion was determined by measuring the percentage of cells that bound fluorescent beads by flow cytometry using a FACSca (Becton Dickinson, Oxnard, Calif.).

Results

To investigate whether DC-SIGN and DC-SIGN-R are receptors for HCV E2, stable HeLa cell lines were produced by transfection of cDNAs encoding either DC-SIGN or DC-SIGN-R. Flow cytometric analysis was performed on selected clones of these cells (HeLa-DC-SIGN and HeLa-DC-SIGN-R) using a panel of anti-DC-SIGN or anti-DC-SIGN-R specific antibodies that have been reported to react with human tissues (FIG. 4 and Table 1 below). High levels of DC-SIGN and DC-SIGN-R molecules were expressed at the cell surface of the respective cell lines. HeLa parent cells did not stain with any of the anti-DC-SIGN or anti-DC-SIGN-R antibodies.

TABLE 1

Cell surface expression of DC-SIGN and DC-SIGN-R in HeLa-DC-SIGN and HeLa-DC-SIGN-R stable cell lines.

| Antibody Clone | Specificity | % Positive Cells (Mean fluorescence intensity) | | |
|---|---|---|---|---|
| | | HeLa-DC-SIGN | HeLa-DC-SIGN-R | HeLa parent |
| 507 (D) | DC-SIGN | 90.6 (81.1) | 3.5 (17.1) | 0.8 (7.8) |
| 612 (X) | DC-SIGN, DC-SIGNR | 67.3 (46.6) | 94.8 (102.1) | 0.3 (8.1) |
| 604 (L) | DC-SIGNR | 1.1 (14.2) | 96.0 (128.9) | 0.1 (8.6) |
| Isotype control | none | 1.0 (16.9) | 2.8 (13.7) | 0.1 (7.9) |

To determine whether DC-SIGN and DC-SIGN-R bind to HCV-E2 glycoproetin, a flow cytometric adhesion assay (Geijtenbeek et al, Blood, 94, 754–764 (1999)) was adapted. HCV-E2 protein produced in CHO cells was captured on fluorescent beads using a panel of anti-E2 mAbs, which were incubated with DC-SIGN- and DC-SIGN-R-HeLa cells at a ratio of 20 beads per cell. The HCV-E2 coated beads bound efficiently to both cell types, and binding was efficiently inhibited by mannan (FIG. 5) and EDTA or EGTA (data not shown). Low levels of background adhesion were observed in the non-transfected HeLa parent cell line, which does not express DC-SIGN or DC-SIGN-R. Binding levels were dependent on the anti-E2 mAb used for coating, however the trend was similar for DC-SIGN and DC-SIGN-R cells. Beads conjugated with antibody only, and without E2 protein, did not bind to cells (data not shown).

Figure 6:
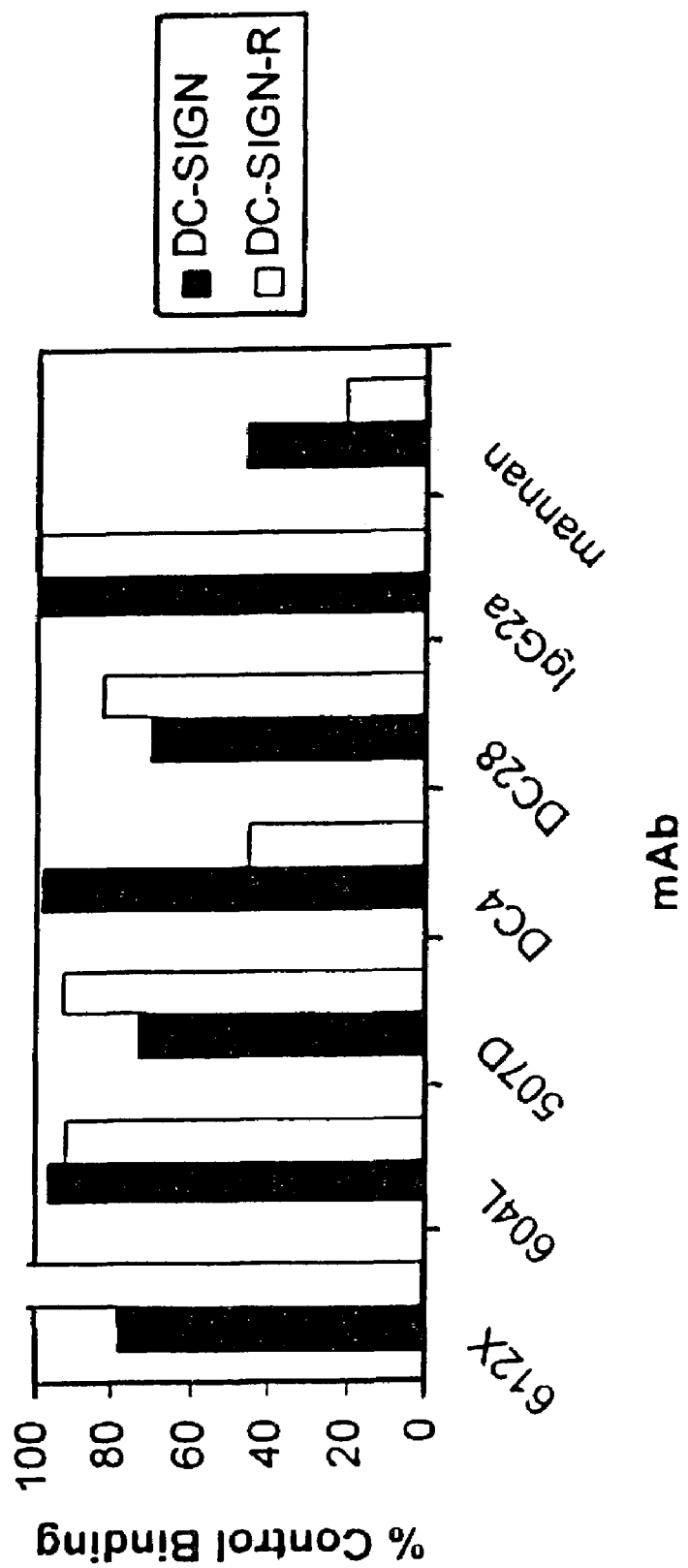

The panel of anti-DC-SIGN and anti-D-SIGN-R mAbs was tested for their effect on E2:DC-SIGN/DC-SIGN-R adhesion in the fluorescent bead binding assay (FIG. 6). E2 binding to DC-SIGN-R was inhibited by DC4, a mAb that recognizes both DC-SIGN and DC-SIGN-R, however, binding to DC-SIGN was only moderately inhibited by a subset of mAbs in the panel, suggesting that E2 may interact with different sites on these molecules. DC4 does not inhibit lentivirus attachment or ICAM-3 binding to DC-SIGN and DC-SIGN-R, therefore, it may represent a novel HCV-specific inhibitor Discussion It has therefore been demonstrated that HCV-E2 glycoprotein interacts with DC-SIGN and DC-SIGN-R, and that mannan, calcium chelators and an anti-DC-SIGN/DC-SIGN-R mAb inhibit this interaction. These findings are novel, and the expression of these potential HCV receptors on DC and endothelium has important implications for viral life cycle. DC-SIGN expressed on DC may transmit HCV in trans to susceptible cells in a similar fashion to HIV, and expression of DC-SIGN-R in the liver and placenta may dictate viral tropism and subsequent pathogenesis.

Liver sinusoidal endothelial cells are in continuous contact with passing leukocytes, and may capture viruses, apoptotic cells and antigens from the blood and promote trans-infection of target cells. It is thus possible that DC-SIGN-R promotes infection of these cells, thereby establishing a reservoir for production of new virus to pass on to hepatocytes. A similar mechanism may operate for vertical transmission of HCV via term placenta, a tissue that contains high levels of DC-SIGN-R. Inhibition of these interactions represents therapeutic and prophylactic strategies for HCV disease. The role of DC-SIGN-R and DC-SIGN as tethering molecules that orchestrates HCV trafficking and localization to the liver remain to be elucidated, however their interactions with HCV-E2 represent novel targets for therapeutic intervention.

Second Set of Experiments

Summary

An inhibitor of HCV attachment to DC-SIGN and/or DC-SIGN-R is described that abrogates binding of HCV positive sera, or purified virions in the assay described below. This inhibitor may interact with the virus, or the receptor, or both.

Serum Binding to Cells

HeLa cell lines (HeLa-DC-SIGN, HeLa-DC-SIGN-R) or parental HeLa cells are cultured overnight in DMEM containing 10% FBS in a 24-well plate at 1×105 cells/well. The following day, the cells are washed once with adherence buffer and then blocked with adherence buffer containing 10% heat-inactivated goat serum for 20 minutes at 37° C. The cells are washed once with adherence buffer, and inhibitor(s) are added for 1 hour in adhesion buffer to half of the wells. Ten µL of either HCV RNA+ (virus positive) or HCV RNA-serum (virus negative) is diluted in advance for a final volume of 200 µL, and is added to the wells. Inhibitor(s) may also be added to aliquots of the sera for 1 hour to enable interaction with virus. The virus is allowed to bind to cells for 1 hour at 37° C. with gentle agitation every 15 minutes. Finally, the serum is removed and the cells are washed five times with adherence buffer.

Viral RNA Extraction

Viral RNA is extracted from cells using a QIAmp Viral RNA Mini Spin kit (Qiagen) with modifications. Briefly, two extractions with 280 µL of lysis buffer are added per well and transferred to a 1.7 mL tube. The empty plate is washed with 140 µL of Dulbecco's phosphate buffered saline with calcium and magnesium, and pooled into the same tube. RNA extraction and binding to spin columns is done using the manufacturer's guidelines. Following a wash with wash buffer, DNA on the column is removed by treatment with RNase-free DNase (Qiagen) using the manufacturer's guidelines. RNA is washed and eluted in two steps using 30 µL and 40 µL elution buffer, and the eluate is combined.

HCV-Specific RT-PCR

One half nmol of primer RJD-5 is combined with 0.5 µL of extracted RNA in a final volume of 6 µL. Samples are heated for 10 minutes at 70° C. and then cooled to 4° C. using a GeneAmp PCR system (Perkin Elmer). In a 10 µL reaction mixture, the pre-heated template is combined with 1× First Strand Buffer, 10 mM DTT, 5 mM deoxyribo-nucleoside triphosphates (dNTPs), and 7.5 U of Thermo-Script (Invitrogen), incubated at 58° C. for 50 minutes, then 85° C. for 5 minutes, before cooling to 4° C. From this RT reaction, 5 µL is used as the template for PCR in a 50 µL reaction containing 1× High Fidelity PCR Buffer, 2 mM MgSO4, 2 mM dNTPs, 50 pmol primers RJD-1 and RJD-5, and 1.25 U Platinum Taq high fidelity DNA polymerase (Invitrogen). PCR amplification is accomplished using the method of Young et al. (Young KK, Resnik R M, Myers T W. Detection of hepatitis C virus RNA by a combined reverse transcription-polymerase chain reaction assay. J Clin Microbiol. 1993 Apr. 3:31(4):882–6.)

Blotting of RT-PCR Products

Ten µL of each RT-PCR reaction is resolved on a 1% agarose gel containing a biotinylated DNA ladder (NEB). The gel is capillary blotted onto a Protran nitrocellulose membrane (type BA-85, Schleicher and Schull) following the Southern blot method described in Sambrook, Fritsch, and Maniatis (Sambrook, J., Fritsch, E. F., and Maniatis, T., in Molecular Cloning: A Laboratory Manual. Cold Spring Harbor Laboratory Press, N.Y., Vol. 1, 2, 3 (1989). The following day the DNA is crosslinked to the membrane at 2400 J/m2 using a StrataLinker (Stratagene) and dried at room temperature for at least 1 hour.

Hybridization to Detect HCV

The blot is incubated for 4 hours at 63° C. in prehybridization solution. Prehybridization solution contains 5× Denhardt's [0.2% (w/v) fatty-acid free BSA (JRH Biosciences), 0.2% (w/v) polyvinylpyrrolidonpolyvinyl (PVP, Sigma), 0.2% (w/v) Ficoll-400 (Sigma)], 6×SSC (0.9 M NaCl, 90 mM sodium citrate pH 7.4), 0.5% (w/v) sodium dodecyl-sulfate (SDS, Promega), and 0.1 mg/mL Hering Sperm DNA (Invitrogen). After the incubation, 1 pmol/mL of primer RJD-6 or RJD-7 is added to the prehybridization solution to make the hybridization solution, and is incubated overnight at 63° C. The following morning, the blot is washed twice for 5 minutes in wash buffer [2×SSC, 0.1% (w/v) SDS] at room temperature, twice for 15 minutes in wash buffer at 63° C., and once more in wash buffer at room temperature. The blot is then washed once for 5 minutes in PBST [Dulbecco's phosphate buffered saline without calcium and magnesium, 0.05% (v/v) Tween-20]. The blot is then incubated with strepavidin-HRP (Amersham) at 1/1500 in PBST for 45 minutes at room temperature. The blot is washed twice quickly then three times for 15 minutes in PBST. The blot is developed using Western Lightening (NEN/Perkin Elmer) and Kodak film. An HCV RNA positive signal is exemplified by a specific band of 243 base pairs. The intensity of the 243 base pair band is compared in the presence and the absence of inhibitor, and a reduction in intensity indicates inhibition of HCV binding.

| Oligo name | Sequence |
| --- | --- |
| RJD-1 (KY80[1]) | 5'-GCA GAA AGC GTC TAG CCA TGG CGT-3' |
| RJD-5 (KY78[1]) | 5'-CTC GCA AGC ACC CTA TCA GGC AGT-3' |
| RJD-6 | 5' biotin-GGA GAG CCA TAG TGG TCT GCG GAA C-3' |
| RJD-7 (KY88[1]) | 5' biotin-GTT GGG TCG CGA AAG CCT TGT GGT-3 |

Third Set of Experiments

Summary

A novel, enhanced method for detecting HCV in samples from humans (blood, serum, plasma, tissue, amniotic fluid, et al) is disclosed that utilizes the assay described in the example vide infra. In this method, the samples are tested in the cell binding assay (SIGN assay) for attachment to HeLa cells expressing DC-SIGN and/or DC-SIGN-R. The standard cell-free assay is used as a control at varying dilutions of sample to determine the limit of detection and linearity of the SIGN assay. This test provides additional quantitative information on HCV viral load, (e.g., an increased sensitivity in detecting the presence of HCV in a biological sample), in addition to qualitative properties (DC-SIGN or DC-SIGN-R binding) on the virus present in the sample. This assay provides novel information relevant for receptor usage, the distribution of viral quasi-species (e.g., pathogenic phenotypes) and thus has utility in monitoring clinical disease progression.

Sample Binding to Cells

HeLa cell lines (HeLa-DC-SIGN, HeLa-DC-SIGN-R) or parental HeLa cells are cultured overnight in DMEM containing 10% FBS in a 24-well plate at 1×105 cells/well. The following day, the cells are washed once with adherence buffer and blocked with adherence buffer containing 10% heat-inactivated goat serum for 20 minutes at 37° C. The cells are washed once with adherence buffer. A fixed volume (e.g., 10–1000 µL) of either HCV RNA+ (virus positive) or HCV RNA– serum (virus negative), or other samples (plasma, tissue extracts et al) is diluted in adherence buffer for a final volume of 200 µL, and a range of 10-fold serial dilutions is prepared. These suspensions are added to wells for 1 hour to enable interaction with virus and are incubated at 37° C. with gentle agitation every 15 minutes. Finally, the sample is removed and the cells are washed five times with adherence buffer. To determine the limit of detection and linearity of the assay, aliquots of the same samples are used without cell binding (cell-free samples) in the subsequent steps as discussed below.

Viral RNA Extraction

Viral RNA is extracted from cells, or cell-free samples, using a QIAmp Viral RNA Mini Spin kit (Qiagen) with modifications. Briefly, two extractions with 280 µL of lysis buffer are added per well and transferred to a 1.7 mL tube. The empty plate is washed with 140 µL of Dulbecco's phosphate buffered saline with calcium and magnesium, and pooled into the same tube. RNA extraction and binding to spin columns is carried out using the manufacturer's guidelines. Following a wash with wash buffer, DNA on the column is removed by treatment with RNase-free DNase (Qiagen) using the manufacturer's guidelines. RNA is washed and eluted in two steps using 30 µL and 40 µL elution buffer, and the eluates are combined.

HCV-specific RT-PCR

One half nmol of primer RJD-5 is combined with 0.5 µL of extracted RNA in a final volume of 6 µL. Samples are heated for 10 minutes at 70° C. and then cooled to 4° C. using a GeneAmp PCR system (Perkin Elmer). In a 10 µL reaction mixture, the pre-heated template is combined with 1× First Strand Buffer, 10 mM DTT, 5 mM deoxyribonucleoside triphosphates (dNTPs), and 7.5 U of ThermoScript (Invitrogen), incubated at 58° C. for 50 minutes, then at 85° C. for 5 minutes before cooling to 4° C. From this RT reaction, 5 µL is used as the template for PCR in a 50 µL reaction containing 1× High Fidelity PCR Buffer, 2 mM MgSO4, 2 mM dNTPs, 50 pmol primers RJD-1 and RJD-5, and 1.25 U Platinum Taq high fidelity DNA polymerase (Invitrogen). PCR amplification is accomplished using the method of Young et al. (Young KK, Resnick R M, Myers T W. Detection of hepatitis C virus RNA by a combined reverse transcription-polymerase chain reaction assay. J Clin Microbiol. 1993 April; 31(4):882–6).

Blotting of RT-PCR Products

Ten µL of each RT-PCR reaction is resolved on a 1% agarose gel containing a biotinylated DNA ladder (NEB). The gel is capillary blotted onto a Protran nitrocellulose membrane (type BA-85, Schleicher and Schull) following the Southern blot method described in Sambrook, Fritsch, and Maniatis (Sambrook, J. Frisch, E. F., and Maniatis, T., in Molecular Cloning: A Laboratory Manual. Cold Spring Harbor Laboratory Press, NY, Vol 1, 2, 3 (1989). The following day the DNA is crosslinked to the membrane at 2400 J/m2 using a StrataLinker (Stratagene) and then dried at room temperature for at least 1 hour.

Hybridization to Detect HCV

The blot is incubated for 4 hours at 63° C. in prehybridization solution. The prehybridization solution contains 5× Denhardt's [0.2% (w/v) fatty-acid free BSA (JRH Biosciences), 0.2% (w/v) polyvinylpyrrolidonpolyvinyl (PVP, Sigma), 0.2% (w/v) Ficoll-400 (Sigma)], 6×SSC (0.9M NaCl, 90 mM sodium citrate pH 7.4), 0.5% (w/v) sodium dodecylsulfate (SDS, Promega), and 0.1 mg/mL Hering Sperm DNA (Invitrogen). After the incubation, 1 pmol/mL of primer RJD-6 or RJD-7 is added to the prehybridization solution to make the hybridization solution, which is incubated overnight at 63° C. The following morning, the blot is washed twice for 5 minutes in wash buffer [2×SSC, 0.1% (w/v) SDS] at room temperature, twice for 15 minutes in wash buffer at 63° C., and once more in wash buffer at room temperature. The blot is then washed once for 5 minutes in PBST [Dulbecco's phosphate buffered saline without calcium and magnesium, 0.05% (v/v) Tween-20]. The blot is then incubated with streptavidin-HRP (Amersham) at 1/1500 in PBST for 45 minutes at room temperature. The blot is washed twice quickly then three times for 15 minutes in PBST. The blot is developed using Western Lightening (NEN/Perkin Elmer) and Kodak film. An HCV RNA positive signal is exemplified by a specific band of 243 base pairs. The intensity of the 243 base pair band is compared between identical samples in the cell binding (SIGN) assay, and the cell-free assay for quantitative and qualitative differences. The difference in signal intensities observed in the DC-SIGN and DC-SIGN-R assays provides information relevant to HCV receptor usage and tropism, and ultimately to clinical progression.

| Oligo name | | Sequence |
|---|---|---|
| RJD-1 | (KY80[1]) | 5'-GCA GAA AGC GTC TAG CCA TGG CGT-3' |
| RJD-5 | (KY78[1]) | 5'-CTC GCA AGC ACC CTA TCA GGC AGT-3' |
| RJD-6 | | 5' biotin-GGA GAG CCA TAG TGG TCT GCG GAA C-3 |
| RJD-7 | (KY88[1]) | 5' biotin-GTT GGG TCG CGA AAG CCT TGT GGT-3' |

Numerous other embodiments of the above assay can be envisaged. For example, HCV captured onto Hela-DC-SIGN and/or HeLa-DC-SIGN-R cells can be quantitated using other conventional readouts, such as by Western blot analysis of HCV proteins using antibodies to viral proteins. In another embodiment, purified DC-SIGN and/or DC-SIGN-R proteins can be immobilized onto a surface, such as a plate or bead using conventional technologies, and used to capture and concentrate HCV from patient specimens. The amount of HCV can be quantified using by measuring the number of viral genomes by RT-PCR methods as described, by Western blot analysis of viral proteins, by ELISA, or by other standard methodologies that are well known to those skilled in the art.

One skilled in the art will readily appreciate that the specific methods and results discussed herein are merely illustrative of the invention as described more fully in the claims that follow thereafter.

REFERENCES

1. Alter, H. J. and L. B. Seef. 1993. Transfusion—associated hepatitis. In "Viral Hepatitis" (Z. a. Thomas, Ed.). Churchill Livingstone, Edinburgh
2. Anonymous. 1999. Global surveillance and control of hepatitis C. Report of a WHO Consultation organized in collaboration with the Viral Hepatitis Prevention Board, Antwerp, Belgium. J. Viral. Hepat. 6:35–47.
3. Bashirova, A. A., T. B. Geijtenbeek, G. C. van Duijnhoven, S. J. van Vliet, J. B. Eilering, M. P. Martin, L. Wu, T. D. Martin, N. Viebig, P. A. Knolle, V. N. KewalRamani, Y. van Kooyk, and M. Carrington. 2001. A dendritic cell-specific intercellular adhesion molecule 3-grabbing nonintegrin (dc-sign)-related protein is highly expressed on human liver sinusoidal endothelial cells and promotes hiv-1 infection. J. Exp. Med. 193:671–678.
4. Bertolini, L., S. Iacovacci, A. Ponzetto, G. Gorini, M. Battaglia, and G. Carloni. 1993. The human bone-marrow-derived B-cell line CE, susceptible to hepatitis C virus infection. Res. Virol. 144:281–285.
5. Carloni, G., S. Iacovacci, M. Sargiacomo, G. Ravagnan, A. Ponzetto, C. Peschle, and M. Battaglia. 1993. Susceptibility of human liver cell cultures to hepatitis C virus infection. Arch. Virol. Suppl. 8:31–39.
6. Cocquerel, L., S. Duvet, J. C. Meunier, A. Pillez, R. Cacan, C. Wychowski, and J. Dubuisson. 1999. The transmembrane domain of hepatitis C virus glycoprotein E1 is a signal for static retention in the endoplasmic reticulum. J. Virol. 73:2641–2649.
7. Cocquerel, L., J. C. Meunier, A. Pillez, C. Wychowski, and J. Dubuisson. 1998. A retention signal necessary and sufficient for endoplasmic reticulum localization maps to the transmembrane domain of hepatitis C virus glycoprotein E2. J. Virol. 72:2183–2191.
8. Cocquerel, L., C. Wychowski, F. Minner, F. Penin, and J. Dubuisson. 2000. Charged residues in the transmembrane domains of hepatitis C virus glycoproteins play a major role in the processing, subcellular localization, and assembly of these envelope proteins. J. Virol. 74:3623–3633.
9. Dubuisson, J. 2000. Folding, assembly and subcellular localization of hepatitis C virus glycoproteins. Curr. Top. Microbiol. Immunol. 242:135–148.
10. Dubuisson, J., H. H. Hsu, R. C. Cheung, H. B. Greenberg, D. G. Russell, and C. M. Rice. 1994. Formation and intracellular localization of hepatitis C virus envelope glycoprotein complexes expressed by recombinant vaccinia and Sindbis viruses. J. Virol. 68:6147–6160.
11. Dubuisson, J. and C. M. Rice. 1996. Hepatitis C virus glycoprotein folding: disulfide bond formation and association with calnexin. J. Virol. 70:778–786.
12. Duvet, S., L. Cocquerel, A. Pillez, R. Cacan, A. Verbert, D. Moradpour, C. Wychowski, and J. Dubuisson. 1998. Hepatitis C virus glycoprotein complex localization in the endoplasmic reticulum involves a determinant for retention and not retrieval. J. Biol. Chem. 273:32088–32095.
13. Flint, M., J. Dubuisson, C. Maidens, R. Harrop, G. R. Guile, P. Borrow, and J. A. McKeating. 2000. Functional characterization of intracellular and secreted forms of a truncated hepatitis C virus E2 glycoprotein. J. Virol. 74:702–709.
14. Flint, M. and J. A. McKeating. 1999. The C-terminal region of the hepatitis C virus E1 glycoprotein confers localization within the endoplasmic reticulum. J. Gen. Virol. 80 (Pt 8):1943–1947.
15. Flint, M., J. M. Thomas, C. M. Maidens, C. Shotton, S. Levy, W. S. Barclay, and J. A. McKeating. 1999. Functional analysis of cell surface-expressed hepatitis C virus E2 glycoprotein. J. Virol. 73:6782–6790.
16. Fry, D. E. and L. M. Flint. 1997. Hepatitis: an overview of important issues. Bull. Am. Coll. Surg. 82:8–13.
17. Geijtenbeek, T. B., D. S. Kwon, R. Torensma, S. J. van Vliet, G. C. van Duijnhoven, J. Middel, I. L. Cornelissen, H. S. Nottet, V. N. KewalRamani, D. R. Littman, C. G. Figdor, and Y. van Kooyk. 2000. DC-SIGN, a dendritic cell-specific HIV-1-binding protein that enhances transinfection of T cells. Cell 100:587–597.
18. Gilljam, G. 1993. Envelope glycoproteins of HIV-1, HIV-2, and SIV purified with Galanthus nivalis agglutinin induce strong immune responses. AIDS Res. Hum. Retroviruses 9:431–438.
19. Grakoui, A., C. Wychowski, C. Lin, S. M. Feinstone, and C. M. Rice. 1993. Expression and identification of hepatitis C virus polyprotein cleavage products. J. Virol. 67:1385–1395.
20. Higginbottom, A., E. R. Quinn, C. C. Kuo, M. Flint, L. H. Wilson, E. Bianchi, A. Nicosia, P. N. Monk, J. A. McKeating, and S. Levy. 2000. Identification of amino acid residues in CD81 critical for interaction with hepatitis C virus envelope glycoprotein E2. J. Virol. 74:3642–3649.
21. Hijikata, M., N. Kato, Y. Ootsuyama, M. Nakagawa, and K. Shimotohno. 1991. Gene mapping of the putative structural region of the hepatitis C virus genome by in vitro processing analysis. Proc. Natl. Acad. Sci. U.S.A. 88:5547–5551.
22. Hong, Z., M. Beaudet-Miller, R. E. Lanford, B. Guerra, J. Wright-Minogue, A. Skelton, B. M. Baroudy, G. R. Reyes, and J. Y. Lau. 1999. Generation of transmissible hepatitis C virions from a molecular clone in chimpanzees. Virology 256:36–44.
23. Iacovacci, S., L. Bertolini, A. Manzin, M. B. Valli, M. Battaglia, A. Ponzetto, M. Clementi, and G. Carloni. 1997. Quantitation of hepatitis C virus RNA production in two human bone marrow-derived B-cell lines infected in vitro. Res. Virol. 148:147–151.
24. Iacovacci, S., A. Manzin, S. Barca, M. Sargiacomo, A. Serafino, M. B. Valli, G. Macioce, H. J. Hassan, A. Ponzetto, M. Clementi, C. Peschle, and G. Carloni. 1997. Molecular characterization and dynamics of hepatitis C virus replication in human fetal hepatocytes infected in vitro. Hepatology 26:1328–1337.

25. Jones, I. M., C. Chan-Fook, W. R. Jiang, and B. E. Clarke. 2000. Receptors for hepatitis C virus. J. Virol. 74:10860–10861.

26. Kato, N., T. Nakazawa, T. Mizutani, and K. Shimotohno. 1995. Susceptibility of human T-lymphotropic virus type I infected cell line MT-2 to hepatitis C virus infection. Biochem. Biophys. Res. Commun. 206:863–869.

27. Kolykhalov, A. A., E. V. Agapov, K. J. Blight, K. Mihalik, S. M. Feinstone, and C. M. Rice. 1997. Transmission of hepatitis C by intrahepatic inoculation with transcribed RNA. Science 277:570–574.

28. Lagging, L. M., K. Meyer, R. J. Owens, and R. Ray. 1998. Functional role of hepatitis C virus chimeric glycoproteins in the infectivity of pseudotyped virus. J. Virol. 72:3539–3546.

29. Lanford, R. E., C. Sureau, J. R. Jacob, R. White, and T. R. Fuerst. 1994. Demonstration of in vitro infection of chimpanzee hepatocytes with hepatitis C virus using strand-specific RT/PCR. Virology 202:606–614.

30. Lohmann, V., F. Korner, J. Koch, U. Herian, L. Theilmann, and R. Bartenschlager. 1999. Replication of subgenomic hepatitis C virus RNAs in a hepatoma cell line. Science 285:110–113.

31. Matsuura, Y., T. Suzuki, R. Suzuki, M. Sato, H. Aizaki, I. Saito, and T. Miyamura. 1994. Processing of E1 and E2 glycoproteins of hepatitis C virus expressed in mammalian and insect cells. Virology 205:141–150.

32. McHutchison, J. G., S. C. Gordon, E. R. Schiff, M. L. Shiffman, W. M. Lee, V. K. Rustgi, Z. D. Goodman, M. H. Ling, S. Cort, and J. K. Albrecht. 1998. Interferon alfa-2b alone or in combination with ribavirin as initial treatment for chronic hepatitis C. Hepatitis Interventional Therapy Group. N. Engl. J. Med. 339:1485–1492.

33. Meola, A., A. Sbardellati, E. B. Bruni, M. Cerretani, M. Pezzanera, A. Ceccacci, A. Vitelli, S. Levy, A. Nicosia, C. Traboni, J. McKeating, and E. Scarselli. 2000. Binding of hepatitis C virus E2 glycoprotein to CD81 does not correlate with species permissiveness to infection. J. Virol. 74:5933–5938.

34. Meunier, J. C., A. Fournillier, A. Choukhi, A. Cahour, L. Cocquerel, J. Dubuisson, and C. Wychowski. 1999. Analysis of the glycosylation sites of hepatitis C virus (HCV) glycoprotein E1 and the influence of E1 glycans on the formation of the HCV glycoprotein complex. J.Gen.Virol. 80 (Pt 4):887–896.

35. Michalak, J. P., C. Wychowski, A. Choukhi, J. C. Meunier, S. Ung, C. M. Rice, and J. Dubuisson. 1997. Characterization of truncated forms of hepatitis C virus glycoproteins. J. Gen. Virol. 78 (Pt 9):2299–2306.

36. Op De Beeck, A., R. Montserret, S. Duvet, L. Cocquerel, R. Cacan, B. Barberot, M. Le Maire, F. Penin, and J. Dubuisson. 2000. The transmembrane domains of hepatitis C virus envelope glycoproteins E1 and E2 play a major role in heterodimerization. J. Biol. Chem. 275: 31428–31437.

37. Patel, J., A. H. Patel, and J. McLauchlan. 1999. Covalent interactions are not required to permit or stabilize the non-covalent association of hepatitis C virus glycoproteins E1 and E2. J.Gen.Virol. 80 (Pt 7):1681–1690.

38. Petracca, R., F. Falugi, G. Galli, N. Norais, D. Rosa, S. Campagnoli, V. Burgio, E. Di Stasio, B. Giardina, M. Houghton, S. Abrignani, and G. Grandi. 2000. Structure-function analysis of hepatitis C virus envelope-CD81 binding. J. Virol. 74:4824–4830.

39. Pileri, P., Y. Uematsu, S. Campagnoli, G. Galli, F. Falugi, R. Petracca, A. J. Weiner, M. Houghton, D. Rosa, G. Grandi, and S. Abrignani. 1998. Binding of hepatitis C virus to CD81. Science 282:938–941.

40. Pohlmann, S., E. J. Soilleux, F. Baribaud, G. J. Leslie, L. S. Morris, J. Trowsdale, B. Lee, N. Coleman, and R. W. Doms. 2001. DC-SIGNR, a DC-SIGN homologue expressed in endothelial cells, binds to human and simian immunodeficiency viruses and activates infection in trans. Proc. Natl. Acad. Sci. U.S.A. 98:2670–2675.

41. Ralston, R., K. Thudium, K. Berger, C. Kuo, B. Gervase, J. Hall, M. Selby, G. Kuo, M. Houghton, and Q. L. Choo. 1993. Characterization of hepatitis C virus envelope glycoprotein complexes expressed by recombinant vaccinia viruses. J. Virol. 67:6753–6761.

42. Rice, C. M. 1996. Flaviviridiae: The viruses and their replication. 3rd ed. In "Fields Virology" (B. N. Fields, Ed.) pp. 931–1034. Lippincott-Raven Publishers, Philadelphia 43. Selby, M. J., E. Glazer, F. Masiarz, and M. Houghton. 1994. Complex processing and protein:protein interactions in the E2:NS2 region of HCV. Virology 204:114–122.

44. Shimizu, Y. K., A. Iwamoto, M. Hijikata, R. H. Purcell, and H. Yoshikura. 1992. Evidence for in vitro is replication of hepatitis C virus genome in a human T-cell line. Proc. Natl. Acad. Sci. U.S.A. 89:5477–5481.

45. Shimizu, Y. K., A. J. Weiner, J. Rosenblatt, D. C. Wong, M. Shapiro, T. Popkin, M. Houghton, H. J. Alter, and R. H. Purcell. 1990. Early events in hepatitis C virus infection of chimpanzees. Proc. Natl. Acad. Sci. U.S.A. 87:6441–6444.

46. Smith, D. B. and P. Simmonds. 1998. Hepatitis C virus: types, subtypes and beyond. In "Methods in molecular medicine" (Lau, Ed.), pp. 134–146. Humana Press, Totowa 47. Soilleux, E. J., R. Barten, and J. Trowsdale. 2000. DC-SIGN; a related gene, DC-SIGNR; and CD23 form a cluster on 19p13. J. Immunol. 165:2937–2942.

48. Spaete, R. R., D. Alexander, M. E. Rugroden, Q. L. Choo, K. Berger, K. Crawford, C. Kuo, S. Leng, C. Lee, and R. Ralston. 1992. Characterization of the hepatitis C virus E2/NS1 gene product expressed in mammalian cells. Virology 188:819–830.

49. Takikawa, S., K. Ishii, H. Aizaki, T. Suzuki, H. Asakura, Y. Matsuura, and T. Miyamura. 2000. Cell fusion activity of hepatitis C virus envelope proteins. J. Virol. 74:5066–5074.

50. Trkola, A., T. Dragic, J. Arthos, J. M. Binley, W. C. Olson, C. P. Allaway, C. Cheng-Mayer, J. Robinson, P. J. Maddon, and J. P. Moore. 1996. CD4-dependent, antibody-sensitive interactions between HIV-1 and its co-receptor CCR-5. Nature 384:184–187.

51. Valli, M. B., G. Carloni, A. Manzin, F. Nasorri, A. Ponzetto, and M. Clementi. 1997. Hepatitis C virus infection of a Vero cell clone displaying efficient virus-cell binding. Res. Virol. 148:181–186.

52. Wunschmann, S., J. D. Medh, D. Klinzmann, W. N. Schmidt, and J. T. Stapleton. 2000. Characterization of hepatitis C virus (HCV) and HCV E2 interactions with CD81 and the low-density lipoprotein receptor. J. Virol. 74:10055–10062.

53. Yanagi, M., R. H. Purcell, S. U. Emerson, and J. Bukh. 1999. Hepatitis C virus: an infectious molecular clone of a second major genotype (2a) and lack of viability of intertypic 1a and 2a chimeras. Virology 262:250–263.

54. Galun et al (1995) J. Inf Dis 172:25.

What is claimed:

1. A method of inhibiting in vivo Hepatitis C Virus (HCV) infection of a liver hepatocyte cell susceptible to HCV infection which comprises contacting a liver sinusoidal cell with an amount of an antibody or a portion thereof effective to inhibit binding of an HCV envelope glycoprotein to a DC-SIGNR protein present on the surface of the liver sinusoidal cell, so as to thereby inhibit HCV infection of the liver hepatocyte cell susceptible to HCV infection, wherein the antibody or portion thereof binds to the DC-SIGNR protein.

2. The method of claim 1, wherein the antibody or portion thereof is a monoclonal antibody or portion thereof.

3. The method of claim 1, wherein the antibody or portion thereof is a polyclonal antibody or portion thereof.

4. The method of claim 1, wherein the antibody or portion thereof is a humanized antibody or portion thereof.

5. The method of claim 1, wherein the antibody or portion thereof is a chimeric antibody or or portion thereof.

6. The method of claim 1, wherein the antibody or portion thereof comprises an antibody Fab portion.

7. The method of claim 1, wherein the antibody or portion thereof comprises an antibody F(ab')2 portion.

8. The method of claim 1, wherein the antibody or portion thereof comprises an antibody Fd portion.

9. The method of claim 1, wherein the antibody or portion thereof comprises an antibody Fv portion.

10. The method of claim 1, wherein the HCV envelope glycoprotein is an HCV E2 envelope glycoprotein.

11. The method of claim 1, wherein the liver hepatocyte cell is present in a subject and the contacting is effected by administering the antibody or portion thereof to the subject.

12. The method of claim 11, wherein the antibody or portion thereof is administered orally, intravenously, subcutaneously, intramuscularly, topically or by liposome-mediated delivery.

13. The method of claim 11, wherein the subject is a human being, a primate, an equine, an opine, an avian, a bovine, a porcine, a canine, a feline or a murine subject.

14. The method of claim 13, wherein the effective amount of the antibody or portion thereof is between 1 mg and 50 mg per kg body weight of the subject.

15. The method of claim 14, wherein the effective amount of the antibody or portion thereof is between 2 mg and 40 mg per kg body weight of the subject.

16. The method of claim 15, wherein the effective amount of the antibody or portion thereof is between 3 mg and 30 mg per kg body weight of the subject.

17. The method of claim 16, wherein the effective amount of the antibody or portion thereof is between 4 mg and 20 mg per kg body weight of the subject.

18. The method of claim 17, wherein the effective amount of the antibody or portion thereof is between 5 mg. and 10 mg per kg body weight of the subject.

19. The method of claim 11, wherein the antibody or portion thereof is administered at least once per day.

20. The method of claim 19, wherein the antibody or portion thereof is administered daily.

21. The method of claim 11, wherein the antibody or portion thereof is administered every other day.

22. The method of claim 11, wherein the antibody or portion thereof is administered every 6 to 8 days.

23. The method of claim 22, wherein the antibody or portion thereof is administered weekly.

* * * * *

SEQUENCE LISTING

<160> NUMBER OF SEQ ID NOS: 3

<210> SEQ ID NO 1
<211> LENGTH: 404
<212> TYPE: PRT
<213> ORGANISM: Homo sapiens

<400> SEQUENCE: 1

Met Ser Asp Ser Lys Glu Pro Arg Leu Gln Gln Leu Gly Leu Glu
1               5                   10                  15

Glu Glu Gln Leu Arg Gly Leu Gly Phe Arg Gln Thr Arg Gly Tyr Lys
            20                  25                  30

Ser Leu Ala Gly Cys Leu Gly His Gly Pro Leu Val Leu Gln Leu Leu
            35                  40                  45

Ser Phe Thr Leu Leu Ala Gly Leu Leu Val Gln Val Ser Lys Val Pro
        50                  55                  60

Ser Ser Ile Ser Gln Glu Gln Ser Arg Gln Asp Ala Ile Tyr Gln Asn
65              70                  75                  80

Leu Thr Gln Leu Lys Ala Ala Val Gly Glu Leu Ser Glu Lys Ser Lys
            85                  90                  95

Leu Gln Glu Ile Tyr Gln Glu Leu Thr Gln Leu Lys Ala Ala Val Gly
            100                 105                 110

Glu Leu Pro Glu Lys Ser Lys Leu Gln Glu Ile Tyr Gln Glu Leu Thr
        115                 120                 125

Arg Leu Lys Ala Ala Val Gly Glu Leu Pro Glu Lys Ser Lys Leu Gln
        130                 135                 140

Glu Ile Tyr Gln Glu Leu Thr Trp Leu Lys Ala Ala Val Gly Glu Leu
145                 150                 155                 160

Pro Glu Lys Ser Lys Met Gln Glu Ile Tyr Gln Glu Leu Thr Arg Leu
            165                 170                 175

Lys Ala Ala Val Gly Glu Leu Pro Glu Lys Ser Lys Gln Gln Glu Ile
            180                 185                 190

Tyr Gln Glu Leu Thr Arg Leu Lys Ala Ala Val Gly Glu Leu Pro Glu
        195                 200                 205

Lys Ser Lys Gln Gln Glu Ile Tyr Gln Glu Leu Thr Arg Leu Lys Ala
210                 215                 220

Ala Val Gly Glu Leu Pro Glu Lys Ser Lys Gln Gln Glu Ile Tyr Gln
225                 230                 235                 240

Glu Leu Thr Gln Leu Lys Ala Ala Val Glu Arg Leu Cys His Pro Cys
            245                 250                 255

Pro Trp Glu Trp Thr Phe Phe Gln Gly Asn Cys Tyr Phe Met Ser Asn
            260                 265                 270

Ser Gln Arg Asn Trp His Asp Ser Ile Thr Ala Cys Lys Glu Val Gly
        275                 280                 285

Ala Gln Leu Val Val Ile Lys Ser Ala Glu Glu Gln Asn Phe Leu Gln
        290                 295                 300

Leu Gln Ser Ser Arg Ser Asn Arg Phe Thr Trp Met Gly Leu Ser Asp
305                 310                 315                 320

Leu Asn Gln Glu Gly Thr Trp Gln Trp Val Asp Gly Ser Pro Leu Leu
            325                 330                 335

Pro Ser Phe Lys Gln Tyr Trp Asn Arg Gly Glu Pro Asn Asn Val Gly
            340                 345                 350

Glu Glu Asp Cys Ala Glu Phe Ser Gly Asn Gly Trp Asn Asp Asp Lys

-continued

```
                355                 360                 365
Cys Asn Leu Ala Lys Phe Trp Ile Cys Lys Lys Ser Ala Ala Ser Cys
    370                 375                 380

Ser Arg Asp Glu Glu Gln Phe Leu Ser Pro Ala Pro Ala Thr Pro Asn
385                 390                 395                 400

Pro Pro Pro Ala

<210> SEQ ID NO 2
<211> LENGTH: 399
<212> TYPE: PRT
<213> ORGANISM: Homo sapiens
<220> FEATURE:
<221> NAME/KEY: MISC_FEATURE
<222> LOCATION: (368)..(368)
<223> OTHER INFORMATION: Xaa = any amino acid

<400> SEQUENCE: 2

Met Ser Asp Ser Lys Glu Pro Arg Val Gln Gln Leu Gly Leu Leu Glu
1               5                   10                  15

Glu Asp Pro Thr Thr Ser Gly Ile Arg Leu Phe Pro Arg Asp Phe Gln
            20                  25                  30

Phe Gln Gln Ile His Gly His Lys Ser Ser Thr Gly Cys Leu Gly His
        35                  40                  45

Gly Ala Leu Val Leu Gln Leu Leu Ser Phe Met Leu Leu Ala Gly Val
    50                  55                  60

Leu Val Ala Ile Leu Val Gln Val Ser Lys Val Pro Ser Ser Leu Ser
65                  70                  75                  80

Gln Glu Gln Ser Glu Gln Asp Ala Ile Tyr Gln Asn Leu Thr Gln Leu
                85                  90                  95

Lys Ala Ala Val Gly Glu Leu Ser Glu Lys Ser Lys Leu Gln Glu Ile
            100                 105                 110

Tyr Gln Glu Leu Thr Gln Leu Lys Ala Ala Val Gly Glu Leu Pro Glu
        115                 120                 125

Lys Ser Lys Leu Gln Glu Ile Tyr Gln Glu Leu Thr Arg Leu Lys Ala
    130                 135                 140

Ala Val Gly Glu Leu Pro Glu Lys Ser Lys Leu Gln Glu Ile Tyr Gln
145                 150                 155                 160

Glu Leu Thr Arg Leu Lys Ala Ala Val Gly Glu Leu Pro Glu Lys Ser
                165                 170                 175

Lys Leu Gln Glu Ile Tyr Gln Glu Leu Thr Arg Leu Lys Ala Ala Val
            180                 185                 190

Gly Glu Leu Pro Glu Lys Ser Lys Leu Gln Glu Ile Tyr Gln Glu Leu
        195                 200                 205

Thr Glu Leu Lys Ala Ala Val Gly Glu Leu Pro Glu Lys Ser Lys Leu
    210                 215                 220

Gln Glu Ile Tyr Gln Glu Leu Thr Gln Leu Lys Ala Ala Val Gly Glu
225                 230                 235                 240

Leu Pro Asp Gln Ser Lys Gln Gln Ile Tyr Gln Glu Leu Thr Asp
                245                 250                 255

Leu Lys Thr Ala Phe Glu Arg Leu Cys Arg His Cys Pro Lys Asp Trp
            260                 265                 270

Thr Phe Phe Gln Gly Asn Cys Tyr Phe Met Ser Asn Ser Gln Arg Asn
        275                 280                 285

Trp His Asp Ser Val Thr Ala Cys Gln Glu Val Arg Ala Gln Leu Val
    290                 295                 300
```

```
Val Ile Lys Thr Ala Glu Glu Gln Asn Phe Leu Gln Leu Gln Thr Ser
305                 310                 315                 320

Arg Ser Asn Arg Phe Ser Trp Met Gly Leu Ser Asp Leu Asn Gln Glu
            325                 330                 335

Gly Thr Trp Gln Trp Val Asp Gly Ser Pro Leu Ser Pro Ser Phe Gln
            340                 345                 350

Arg Tyr Trp Asn Ser Gly Glu Pro Asn Asn Ser Gly Asn Glu Asp Xaa
            355                 360                 365

Ala Glu Phe Ser Gly Ser Gly Trp Asn Asp Asn Arg Cys Asp Val Asp
370                 375                 380

Asn Tyr Trp Ile Cys Lys Lys Pro Ala Ala Cys Phe Arg Asp Glu
385                 390                 395

<210> SEQ ID NO 3
<211> LENGTH: 3011
<212> TYPE: PRT
<213> ORGANISM: Hepatitis C virus

<400> SEQUENCE: 3

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285
```

-continued

```
Gln Leu Phe Thr Phe Ser Pro Arg Arg His Trp Thr Thr Gln Asp Cys
    290                 295                 300
Asn Cys Ser Ile Tyr Pro Gly His Ile Thr Gly His Arg Met Ala Trp
305                 310                 315                 320
Asp Met Met Met Asn Trp Ser Pro Thr Ala Ala Leu Val Val Ala Gln
                325                 330                 335
Leu Leu Arg Ile Pro Gln Ala Ile Met Asp Met Ile Ala Gly Ala His
            340                 345                 350
Trp Gly Val Leu Ala Gly Ile Ala Tyr Phe Ser Met Val Gly Asn Trp
        355                 360                 365
Ala Lys Val Leu Val Val Leu Leu Phe Ala Gly Val Asp Ala Glu
    370                 375                 380
Thr His Val Thr Gly Gly Ser Ala Gly Arg Thr Thr Ala Gly Leu Val
385                 390                 395                 400
Gly Leu Leu Thr Pro Gly Ala Lys Gln Asn Ile Gln Leu Ile Asn Thr
                405                 410                 415
Asn Gly Ser Trp His Ile Asn Ser Thr Ala Leu Asn Cys Asn Glu Ser
            420                 425                 430
Leu Asn Thr Gly Trp Leu Ala Gly Leu Phe Tyr Gln His Lys Phe Asn
        435                 440                 445
Ser Ser Gly Cys Pro Glu Arg Leu Ala Ser Cys Arg Arg Leu Thr Asp
    450                 455                 460
Phe Ala Gln Gly Trp Gly Pro Ile Ser Tyr Ala Asn Gly Ser Gly Leu
465                 470                 475                 480
Asp Glu Arg Pro Tyr Cys Trp His Tyr Pro Pro Arg Pro Cys Gly Ile
                485                 490                 495
Val Pro Ala Lys Ser Val Cys Gly Pro Val Tyr Cys Phe Thr Pro Ser
            500                 505                 510
Pro Val Val Val Gly Thr Thr Asp Arg Ser Gly Ala Pro Thr Tyr Ser
        515                 520                 525
Trp Gly Ala Asn Asp Thr Asp Val Phe Val Leu Asn Asn Thr Arg Pro
    530                 535                 540
Pro Leu Gly Asn Trp Phe Gly Cys Thr Trp Met Asn Ser Thr Gly Phe
545                 550                 555                 560
Thr Lys Val Cys Gly Ala Pro Pro Cys Val Ile Gly Gly Val Gly Asn
                565                 570                 575
Asn Thr Leu Leu Cys Pro Thr Asp Cys Phe Arg Lys His Pro Glu Ala
            580                 585                 590
Thr Tyr Ser Arg Cys Gly Ser Gly Pro Trp Ile Thr Pro Arg Cys Met
        595                 600                 605
Val Asp Tyr Pro Tyr Arg Leu Trp His Tyr Pro Cys Thr Ile Asn Tyr
    610                 615                 620
Thr Ile Phe Lys Val Arg Met Tyr Val Gly Gly Val Glu His Arg Leu
625                 630                 635                 640
Glu Ala Ala Cys Asn Trp Thr Arg Gly Glu Arg Cys Asp Leu Glu Asp
                645                 650                 655
Arg Asp Arg Ser Glu Leu Ser Pro Leu Leu Leu Ser Thr Thr Gln Trp
            660                 665                 670
Gln Val Leu Pro Cys Ser Phe Thr Thr Leu Pro Ala Leu Ser Thr Gly
        675                 680                 685
Leu Ile His Leu His Gln Asn Ile Val Asp Val Gln Tyr Leu Tyr Gly
    690                 695                 700
```

```
Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
        755                 760                 765

Leu Val Phe Phe Cys Phe Ala Trp Tyr Leu Lys Gly Arg Trp Val Pro
    770                 775                 780

Gly Ala Val Tyr Ala Phe Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Met Trp Trp Leu Gln Tyr
        835                 840                 845

Phe Leu Thr Arg Val Glu Ala Gln Leu His Val Trp Val Pro Pro Leu
    850                 855                 860

Asn Val Arg Gly Gly Arg Asp Ala Val Ile Leu Leu Met Cys Val Val
865                 870                 875                 880

His Pro Thr Leu Val Phe Asp Ile Thr Lys Leu Leu Leu Ala Ile Phe
                885                 890                 895

Gly Pro Leu Trp Ile Leu Gln Ala Ser Leu Leu Lys Val Pro Tyr Phe
            900                 905                 910

Val Arg Val Gln Gly Leu Leu Arg Ile Cys Ala Leu Ala Arg Lys Ile
        915                 920                 925

Ala Gly Gly His Tyr Val Gln Met Ala Ile Ile Lys Leu Gly Ala Leu
    930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Arg Met Glu Thr Lys Leu Ile Thr Trp Gly Ala Asp Thr Ala Ala
            980                 985                 990

Cys Gly Asp Ile Ile Asn Gly Leu Pro Val Ser Ala Arg Arg Gly Gln
        995                 1000                1005

Glu Ile Leu Leu Gly Pro Ala Asp Gly Met Val Ser Lys Gly Trp
    1010                1015                1020

Arg Leu Leu Ala Pro Ile Thr Ala Tyr Ala Gln Gln Thr Arg Gly
    1025                1030                1035

Leu Leu Gly Cys Ile Ile Thr Ser Leu Thr Gly Arg Asp Lys Asn
    1040                1045                1050

Gln Val Glu Gly Glu Val Gln Ile Val Ser Thr Ala Thr Gln Thr
    1055                1060                1065

Phe Leu Ala Thr Cys Ile Asn Gly Val Cys Trp Thr Val Tyr His
    1070                1075                1080

Gly Ala Gly Thr Arg Thr Ile Ala Ser Pro Lys Gly Pro Val Ile
    1085                1090                1095

Gln Met Tyr Thr Asn Val Asp Gln Asp Leu Val Gly Trp Pro Ala
    1100                1105                1110

Pro Gln Gly Ser Arg Ser Leu Thr Pro Cys Thr Cys Gly Ser Ser
```

```
                1115                1120                1125
Asp Leu Tyr Leu Val Thr Arg His Ala Asp Val Ile Pro Val Arg
    1130                1135                1140
Arg Arg Gly Asp Ser Arg Gly Ser Leu Leu Ser Pro Arg Pro Ile
    1145                1150                1155
Ser Tyr Leu Lys Gly Ser Ser Gly Gly Pro Leu Leu Cys Pro Ala
    1160                1165                1170
Gly His Ala Val Gly Leu Phe Arg Ala Ala Val Cys Thr Arg Gly
    1175                1180                1185
Val Ala Lys Ala Val Asp Phe Ile Pro Val Glu Asn Leu Glu Thr
    1190                1195                1200
Thr Met Arg Ser Pro Val Phe Thr Asp Asn Ser Pro Pro Ala
    1205                1210                1215
Val Pro Gln Ser Phe Gln Val Ala His Leu His Ala Pro Thr Gly
    1220                1225                1230
Ser Gly Lys Ser Thr Lys Val Pro Ala Ala Tyr Ala Ala Gln Gly
    1235                1240                1245
Tyr Lys Val Leu Val Leu Asn Pro Ser Val Ala Ala Thr Leu Gly
    1250                1255                1260
Phe Gly Ala Tyr Met Ser Lys Ala His Gly Val Asp Pro Asn Ile
    1265                1270                1275
Arg Thr Gly Val Arg Thr Ile Thr Thr Gly Ser Pro Ile Thr Tyr
    1280                1285                1290
Ser Thr Tyr Gly Lys Phe Leu Ala Asp Gly Gly Cys Ser Gly Gly
    1295                1300                1305
Ala Tyr Asp Ile Ile Ile Cys Asp Glu Cys His Ser Thr Asp Ala
    1310                1315                1320
Thr Ser Ile Leu Gly Ile Gly Thr Val Leu Asp Gln Ala Glu Thr
    1325                1330                1335
Ala Gly Ala Arg Leu Val Val Leu Ala Thr Ala Thr Pro Pro Gly
    1340                1345                1350
Ser Val Thr Val Ser His Pro Asn Ile Glu Glu Val Ala Leu Ser
    1355                1360                1365
Thr Thr Gly Glu Ile Pro Phe Tyr Gly Lys Ala Ile Pro Leu Glu
    1370                1375                1380
Val Ile Lys Gly Gly Arg His Leu Ile Phe Cys His Ser Lys Lys
    1385                1390                1395
Lys Cys Asp Glu Leu Ala Ala Lys Leu Val Ala Leu Gly Ile Asn
    1400                1405                1410
Ala Val Ala Tyr Tyr Arg Gly Leu Asp Val Ser Val Ile Pro Thr
    1415                1420                1425
Ser Gly Asp Val Val Val Ser Thr Asp Ala Leu Met Thr Gly
    1430                1435                1440
Phe Thr Gly Asp Phe Asp Ser Val Ile Asp Cys Asn Thr Cys Val
    1445                1450                1455
Thr Gln Thr Val Asp Phe Ser Leu Asp Pro Thr Phe Thr Ile Glu
    1460                1465                1470
Thr Thr Thr Leu Pro Gln Asp Ala Val Ser Arg Thr Gln Arg Arg
    1475                1480                1485
Gly Arg Thr Gly Arg Gly Lys Pro Gly Ile Tyr Arg Phe Val Ala
    1490                1495                1500
Pro Gly Glu Arg Pro Ser Gly Met Phe Asp Ser Ser Val Leu Cys
    1505                1510                1515
```

-continued

```
Glu Cys Tyr Asp Ala Gly Cys Ala Trp Tyr Glu Leu Thr Pro Ala
1520                1525                    1530

Glu Thr Thr Val Arg Leu Arg Ala Tyr Met Asn Thr Pro Gly Leu
1535                1540                    1545

Pro Val Cys Gln Asp His Leu Glu Phe Trp Glu Gly Val Phe Thr
1550                1555                    1560

Gly Leu Thr His Ile Asp Ala His Phe Leu Ser Gln Thr Lys Gln
1565                1570                    1575

Ser Gly Glu Asn Phe Pro Tyr Leu Val Ala Tyr Gln Ala Thr Val
1580                1585                    1590

Cys Ala Arg Ala Gln Ala Pro Pro Pro Ser Trp Asp Gln Met Trp
1595                1600                    1605

Lys Cys Leu Ile Arg Leu Lys Pro Thr Leu His Gly Pro Thr Pro
1610                1615                    1620

Leu Leu Tyr Arg Leu Gly Ala Val Gln Asn Glu Val Thr Leu Thr
1625                1630                    1635

His Pro Ile Thr Lys Tyr Ile Met Thr Cys Met Ser Ala Asp Leu
1640                1645                    1650

Glu Val Val Thr Ser Thr Trp Val Leu Val Gly Gly Val Leu Ala
1655                1660                    1665

Ala Leu Ala Ala Tyr Cys Leu Ser Thr Gly Cys Val Val Ile Val
1670                1675                    1680

Gly Arg Ile Val Leu Ser Gly Lys Pro Ala Ile Ile Pro Asp Arg
1685                1690                    1695

Glu Val Leu Tyr Gln Glu Phe Asp Glu Met Glu Glu Cys Ser Gln
1700                1705                    1710

His Leu Pro Tyr Ile Glu Gln Gly Met Met Leu Ala Glu Gln Phe
1715                1720                    1725

Lys Gln Lys Ala Leu Gly Leu Leu Gln Thr Ala Ser Arg Gln Ala
1730                1735                    1740

Glu Val Ile Thr Pro Ala Val Gln Thr Asn Trp Gln Lys Leu Glu
1745                1750                    1755

Val Phe Trp Ala Lys His Met Trp Asn Phe Ile Ser Gly Ile Gln
1760                1765                    1770

Tyr Leu Ala Gly Leu Ser Thr Leu Pro Gly Asn Pro Ala Ile Ala
1775                1780                    1785

Ser Leu Met Ala Phe Thr Ala Ala Val Thr Ser Pro Leu Thr Thr
1790                1795                    1800

Gly Gln Thr Leu Leu Phe Asn Ile Leu Gly Gly Trp Val Ala Ala
1805                1810                    1815

Gln Leu Ala Ala Pro Gly Ala Ala Thr Ala Phe Val Gly Ala Gly
1820                1825                    1830

Leu Ala Gly Ala Ala Ile Gly Ser Val Gly Leu Gly Lys Val Leu
1835                1840                    1845

Val Asp Ile Leu Ala Gly Tyr Gly Ala Gly Val Ala Gly Ala Leu
1850                1855                    1860

Val Ala Phe Lys Ile Met Ser Gly Glu Val Pro Ser Thr Glu Asp
1865                1870                    1875

Leu Val Asn Leu Leu Pro Ala Ile Leu Ser Pro Gly Ala Leu Val
1880                1885                    1890

Val Gly Val Val Cys Ala Ala Ile Leu Arg Arg His Val Gly Pro
1895                1900                    1905
```

-continued

```
Gly Glu Gly Ala Val Gln Trp Met Asn Arg Leu Ile Ala Phe Ala
    1910            1915                1920

Ser Arg Gly Asn His Val Ser Pro Thr His Tyr Val Pro Glu Ser
    1925            1930                1935

Asp Ala Ala Ala Arg Val Thr Ala Ile Leu Ser Ser Leu Thr Val
    1940            1945                1950

Thr Gln Leu Leu Arg Arg Leu His Gln Trp Ile Ser Ser Glu Cys
    1955            1960                1965

Thr Thr Pro Cys Ser Gly Ser Trp Leu Arg Asp Ile Trp Asp Trp
    1970            1975                1980

Ile Cys Glu Val Leu Ser Asp Phe Lys Thr Trp Leu Lys Ala Lys
    1985            1990                1995

Leu Met Pro Gln Leu Pro Gly Ile Pro Phe Val Ser Cys Gln Arg
    2000            2005                2010

Gly Tyr Arg Gly Val Trp Arg Gly Asp Gly Ile Met His Thr Arg
    2015            2020                2025

Cys His Cys Gly Ala Glu Ile Thr Gly His Val Lys Asn Gly Thr
    2030            2035                2040

Met Arg Ile Val Gly Pro Arg Thr Cys Arg Asn Met Trp Ser Gly
    2045            2050                2055

Thr Phe Pro Ile Asn Ala Tyr Thr Thr Gly Pro Cys Thr Pro Leu
    2060            2065                2070

Pro Ala Pro Asn Tyr Lys Phe Ala Leu Trp Arg Val Ser Ala Glu
    2075            2080                2085

Glu Tyr Val Glu Ile Arg Arg Val Gly Asp Phe His Tyr Val Ser
    2090            2095                2100

Gly Met Thr Thr Asp Asn Leu Lys Cys Pro Cys Gln Ile Pro Ser
    2105            2110                2115

Pro Glu Phe Phe Thr Glu Leu Asp Gly Val Arg Leu His Arg Phe
    2120            2125                2130

Ala Pro Pro Cys Lys Pro Leu Leu Arg Glu Glu Val Ser Phe Arg
    2135            2140                2145

Val Gly Leu His Glu Tyr Pro Val Gly Ser Gln Leu Pro Cys Glu
    2150            2155                2160

Pro Glu Pro Asp Val Ala Val Leu Thr Ser Met Leu Thr Asp Pro
    2165            2170                2175

Ser His Ile Thr Ala Glu Ala Ala Gly Arg Arg Leu Ala Arg Gly
    2180            2185                2190

Ser Pro Pro Ser Met Ala Ser Ser Ser Ala Ser Gln Leu Ser Ala
    2195            2200                2205

Pro Ser Leu Lys Ala Thr Cys Thr Ala Asn His Asp Ser Pro Asp
    2210            2215                2220

Ala Glu Leu Ile Glu Ala Asn Leu Leu Trp Arg Gln Glu Met Gly
    2225            2230                2235

Gly Asn Ile Thr Arg Val Glu Ser Glu Asn Lys Val Val Ile Leu
    2240            2245                2250

Asp Ser Phe Asp Pro Leu Val Ala Glu Glu Asp Glu Arg Glu Val
    2255            2260                2265

Ser Val Pro Ala Glu Ile Leu Arg Lys Ser Arg Arg Phe Ala Arg
    2270            2275                2280

Ala Leu Pro Val Trp Ala Arg Pro Asp Tyr Asn Pro Pro Leu Val
    2285            2290                2295

Glu Thr Trp Lys Lys Pro Asp Tyr Glu Pro Pro Val Val His Gly
```

-continued

```
            2300            2305            2310
Cys Pro Leu Pro Pro Pro Arg Ser Pro Val Pro Pro Pro Arg
    2315            2320            2325
Lys Lys Arg Thr Val Val Leu Thr Glu Ser Thr Leu Ser Thr Ala
    2330            2335            2340
Leu Ala Glu Leu Ala Thr Lys Ser Phe Gly Ser Ser Ser Thr Ser
    2345            2350            2355
Gly Ile Thr Gly Asp Asn Thr Thr Thr Ser Ser Glu Pro Ala Pro
    2360            2365            2370
Ser Gly Cys Pro Pro Asp Ser Asp Val Glu Ser Tyr Ser Ser Met
    2375            2380            2385
Pro Pro Leu Glu Gly Glu Pro Gly Asp Pro Asp Leu Ser Asp Gly
    2390            2395            2400
Ser Trp Ser Thr Val Ser Ser Gly Ala Asp Thr Glu Asp Val Val
    2405            2410            2415
Cys Cys Ser Met Ser Tyr Ser Trp Thr Gly Ala Leu Val Thr Pro
    2420            2425            2430
Cys Ala Ala Glu Glu Gln Lys Leu Pro Ile Asn Ala Leu Ser Asn
    2435            2440            2445
Ser Leu Leu Arg His His Asn Leu Val Tyr Ser Thr Thr Ser Arg
    2450            2455            2460
Ser Ala Cys Gln Arg Gln Lys Lys Val Thr Phe Asp Arg Leu Gln
    2465            2470            2475
Val Leu Asp Ser His Tyr Gln Asp Val Leu Lys Glu Val Lys Ala
    2480            2485            2490
Ala Ala Ser Lys Val Lys Ala Asn Leu Leu Ser Val Glu Glu Ala
    2495            2500            2505
Cys Ser Leu Thr Pro Pro His Ser Ala Lys Ser Lys Phe Gly Tyr
    2510            2515            2520
Gly Ala Lys Asp Val Arg Cys His Ala Arg Lys Ala Val Ala His
    2525            2530            2535
Ile Asn Ser Val Trp Lys Asp Leu Leu Glu Asp Ser Val Thr Pro
    2540            2545            2550
Ile Asp Thr Thr Ile Met Ala Lys Asn Glu Val Phe Cys Val Gln
    2555            2560            2565
Pro Glu Lys Gly Gly Arg Lys Pro Ala Arg Leu Ile Val Phe Pro
    2570            2575            2580
Asp Leu Gly Val Arg Val Cys Glu Lys Met Ala Leu Tyr Asp Val
    2585            2590            2595
Val Ser Lys Leu Pro Leu Ala Val Met Gly Ser Ser Tyr Gly Phe
    2600            2605            2610
Gln Tyr Ser Pro Gly Gln Arg Val Glu Phe Leu Val Gln Ala Trp
    2615            2620            2625
Lys Ser Lys Lys Thr Pro Met Gly Phe Ser Tyr Asp Thr Arg Cys
    2630            2635            2640
Phe Asp Ser Thr Val Thr Glu Ser Asp Ile Arg Thr Glu Glu Ala
    2645            2650            2655
Ile Tyr Gln Cys Cys Asp Leu Asp Pro Gln Ala Arg Val Ala Ile
    2660            2665            2670
Lys Ser Leu Thr Glu Arg Leu Tyr Val Gly Gly Pro Leu Thr Asn
    2675            2680            2685
Ser Arg Gly Glu Asn Cys Gly Tyr Arg Arg Cys Arg Ala Ser Gly
    2690            2695            2700
```

-continued

```
Val Leu Thr Thr Ser Cys Gly Asn Thr Leu Thr Cys Tyr Ile Lys
    2705            2710                2715

Ala Arg Ala Ala Cys Arg Ala Ala Gly Leu Gln Asp Cys Thr Met
    2720            2725                2730

Leu Val Cys Gly Asp Asp Leu Val Val Ile Cys Glu Ser Ala Gly
    2735            2740                2745

Val Gln Glu Asp Ala Ala Ser Leu Arg Ala Phe Thr Glu Ala Met
    2750            2755                2760

Thr Arg Tyr Ser Ala Pro Pro Gly Asp Pro Pro Gln Pro Glu Tyr
    2765            2770                2775

Asp Leu Glu Leu Ile Thr Ser Cys Ser Ser Asn Val Ser Val Ala
    2780            2785                2790

His Asp Gly Ala Gly Lys Arg Val Tyr Tyr Leu Thr Arg Asp Pro
    2795            2800                2805

Thr Thr Pro Leu Ala Arg Ala Ala Trp Glu Thr Ala Arg His Thr
    2810            2815                2820

Pro Val Asn Ser Trp Leu Gly Asn Ile Ile Met Phe Ala Pro Thr
    2825            2830                2835

Leu Trp Ala Arg Met Ile Leu Met Thr His Phe Phe Ser Val Leu
    2840            2845                2850

Ile Ala Arg Asp Gln Leu Glu Gln Ala Leu Asn Cys Glu Ile Tyr
    2855            2860                2865

Gly Ala Cys Tyr Ser Ile Glu Pro Leu Asp Leu Pro Pro Ile Ile
    2870            2875                2880

Gln Arg Leu His Gly Leu Ser Ala Phe Ser Leu His Ser Tyr Ser
    2885            2890                2895

Pro Gly Glu Ile Asn Arg Val Ala Ala Cys Leu Arg Lys Leu Gly
    2900            2905                2910

Val Pro Pro Leu Arg Ala Trp Arg His Arg Ala Arg Ser Val Arg
    2915            2920                2925

Ala Arg Leu Leu Ser Arg Gly Gly Arg Ala Ala Ile Cys Gly Lys
    2930            2935                2940

Tyr Leu Phe Asn Trp Ala Val Arg Thr Lys Leu Lys Leu Thr Pro
    2945            2950                2955

Ile Ala Ala Ala Gly Arg Leu Asp Leu Ser Gly Trp Phe Thr Ala
    2960            2965                2970

Gly Tyr Ser Gly Gly Asp Ile Tyr His Ser Val Ser His Ala Arg
    2975            2980                2985

Pro Arg Trp Phe Trp Phe Cys Leu Leu Leu Leu Ala Ala Gly Val
    2990            2995                3000

Gly Ile Tyr Leu Leu Pro Asn Arg
    3005            3010
```